(12) United States Patent
Reid et al.

(10) Patent No.: US 6,264,824 B1
(45) Date of Patent: Jul. 24, 2001

(54) ASSESSMENT OF CORROSION

(75) Inventors: Stephen Anthony Reid, Lymm; David Anthony Eden, Aberdeenshire, both of (GB)

(73) Assignee: Integriti Investments Ltd., Aberdeen (GB)

( * ) Notice: Subject to any disclaimer, the term of this patent is extended or adjusted under 35 U.S.C. 154(b) by 0 days.

(21) Appl. No.: 09/201,293

(22) Filed: Nov. 30, 1998

(30) Foreign Application Priority Data

Feb. 20, 1998 (GB) .................................................. 9803550
Aug. 14, 1998 (GB) .................................................. 9817600

(51) Int. Cl.[7] .................................................... G01N 27/26
(52) U.S. Cl. ...................... 205/775.5; 204/404; 205/777
(58) Field of Search .................. 204/404; 205/775.5, 205/776, 776.5, 777

(56) References Cited

U.S. PATENT DOCUMENTS

| 3,492,860 | | 2/1970 | Bailey . | |
| 4,575,678 | * | 3/1986 | Hladky | 204/404 |
| 5,051,922 | | 9/1991 | Toral et al. . | |
| 5,139,627 | * | 8/1992 | Eden et al. | 204/404 |
| 5,323,429 | | 6/1994 | Roarty et al. . | |
| 5,888,374 | * | 3/1999 | Pope et al. | 204/404 |
| 6,015,484 | * | 1/2000 | Martinchek et al. | 205/775.5 |

FOREIGN PATENT DOCUMENTS

| 22 352 A1 | 5/1985 | (DD) . |
| 94/12862 | 6/1994 | (WO) . |

OTHER PUBLICATIONS

Leslie W. Flott, "Nonnormal Frequency Distributions", Metal Finishing, May 1995, pp. 52–57.

* cited by examiner

Primary Examiner—T. Tung
(74) Attorney, Agent, or Firm—Ratner & Prestia

(57) ABSTRACT

A method and apparatus for the indentification of corrosion in a metal object is disclosed. The method comprises analyzing the statistical distribution of signals generated between two electrodes, typically exposed to the same corrosion conditions as the metal object, and preferably analyzes the skewness and kurtosis of the signals. Neural nets are preferably used in the analysis.

27 Claims, 58 Drawing Sheets

|  | 0.000 | 0.000 | 0.000 | 0.000 | 1.000 |
|---|---|---|---|---|---|
| ACT. 1.0000 | 0.000 | 0.000 | 0.000 | 1.000 | 0.000 |
|  | 0.000 | 0.000 | 1.000 | 0.000 | 0.000 |
|  | 0.000 | 1.000 | 0.000 | 0.000 | 0.000 |
|  | 1.000 | 0.000 | 0.000 | 0.000 | 0.000 |

DESIRED

CLASSIFICATION RATE

NO SKEW  NEGATIVE SKEW  POSITIVE SKEW

ASSESSMENT OF CORROSION

The present invention relates to the assessment of corrosion.

Electrochemical noise measurements have been used as a means of monitoring corrosion for a number of years, a utilising potential and current measurements. Conventional techniques generally rely on a visual examination of the raw time record data, requiring expertise in the interpretation of the nature of the signals and the calculated values as described.

According to a first aspect of the present invention, there is provided a method for identification of corrosion of a metal object, comprising the steps of providing electrode means capable of generating electrochemical noise signals, and analyzing the statistical distribution of the signals to provide an indication of parameters of the corrosion, said parameters being selected from the group consisting of the extent and the nature of the corrosion.

Preferably at least two electrodes are provided and are exposed to the same corrosion conditions as the metal object, and at least one of the electrodes (preferably two) are fabricated from the same material as the metal object. The signals analyzed from the electrode means can be current or voltage noise, and it is preferred to measure the current between two electrodes and optionally to measure the potential between one of said two electrodes and at least one other electrode.

Typically, analyzing the statistical distribution of the measured values includes the steps of removing the mean value of the measurements, followed by normalisation of the measurements. Typically, the measurements are normalised to one standard deviation. This allows for direct comparison of data sets comprising the measured values from different sources.

Typically, analyzing the statistical distribution of the measured values further comprises the stop of calculating the kurtosis and/or skewness of the measured values. The kurtosis and/or skewness values can be used to indicate the type of corrosion.

Where the potential or current measurements drift significantly, analyzing the statistical distribution typically includes a further step of trend removal.

Typically, a neural network may be used to facilitate interpretation of the statistical distribution. Alternatively, an expert systems approach or alternative pattern recognition techniques may be used. This allows for the data to be analyzed without the requirement for personnel who are experts in the visual interpretation of the data.

According to a second aspect of the present invention, there is provided apparatus for assessing corrosion of a metal object, comprising electrode means capable of generating electrochemical noise signals, and means for calculating the statistical distribution of the signals to indicate parameters selected from the group consisting of the extent and the nature of the corrosion.

Preferably the electrodes are exposed to the same corrosion conditions as the metal object, and at least two of the electrodes are fabricated from the same material as the metal object. Current measuring means is preferably electrically connected between the said two electrodes and potential measuring means is optionally electrically connected between one of said two electrodes and at least one other electrode.

Typically, the processing means for calculating the statistical distribution includes a computer. Typically, the processing means reads the measured values of current and/or potential and processes these to provide the statistical distribution. In preferred embodiments the skewness and kurtosis is assessed. The processing means may store the measured values of current and potential and may also output them to a recording means. The recording means may be a plotter, printer or the like. Alternatively, the measured values may be stored in a memory device, such as on hard disk.

The output of the processing means is typically a statistical distribution of the measured values. The output may be displayed on a monitor and/or stored in the memory device. The output may also be recorded on the recording means.

Typically, the processing means includes an expert system or an alternative pattern recognition system. Such systems may be a neural network, for example, and are used to analyze the output of the processing means to determine the corrosion mechanism.

An embodiment of the present invention will now be described, by way of example only, with reference to the accompanying drawings in which.

Figure 1:
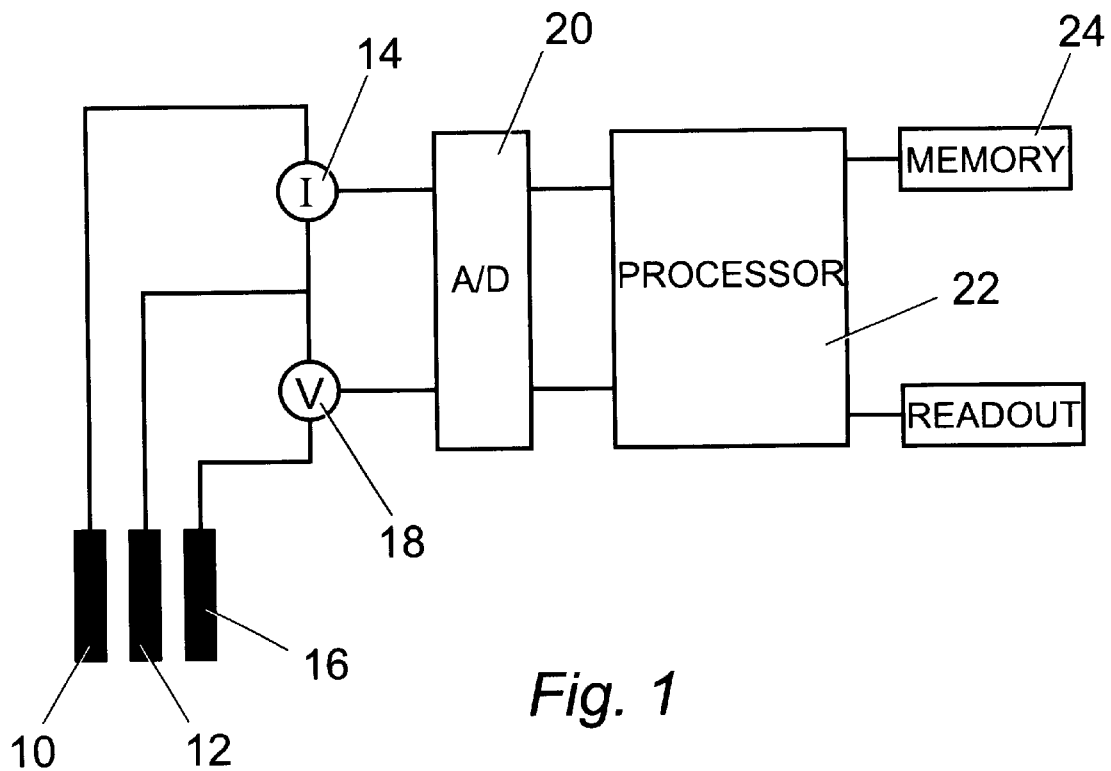
FIG. 1 is a schematic representation of a typical apparatus which may be used in accordance with the second aspect of the present invention.

Referring firstly to FIG. 1, there is shown an example of the apparatus for use with the present invention. The current is measured between two nominally identical electrodes 10, 12 using a zero resistance ammeter (ZRA) 14. The purpose of the ZRA 14 is to effectively create a short circuit between the two electrodes 10, 12 and thus maintain them at substantially the same potential. It will be appreciated that in practice, the potential will not be exactly the same on each electrode 10, 12 due to electrochemical noise generated by corrosion.

The potential between one of the electrode pair 10, 12 (in this case electrode 12) and a third electrode 16 is also measured using a high-input impedance voltmeter 18. The third electrode may be of the same material as the electrode pair 10, 12 or may be fabricated from a substantially inert material. The high-input impedance voltmeter 18 is used to electrically isolate the electrode pair from the third electrode 16, by providing a high impedance between them. The electrodes 10, 12, 16 are submerged in an electrolyte and are allowed to corrode.

Due to the slight differences in the corrosion current and potential of the first and second electrodes 10, 12 at any time, fluctuations will be observed in both the current and potential signals. These fluctuations are measured by the ZRA 14 and the voltmeter 18.

The measured values are then transformed into digital format using, for example, an analogue-to-digital convertor (A/D) 20. The output of the A/D 20 becomes the input to a processor 22. The processor may be, for example, a computer.

Figure 5:
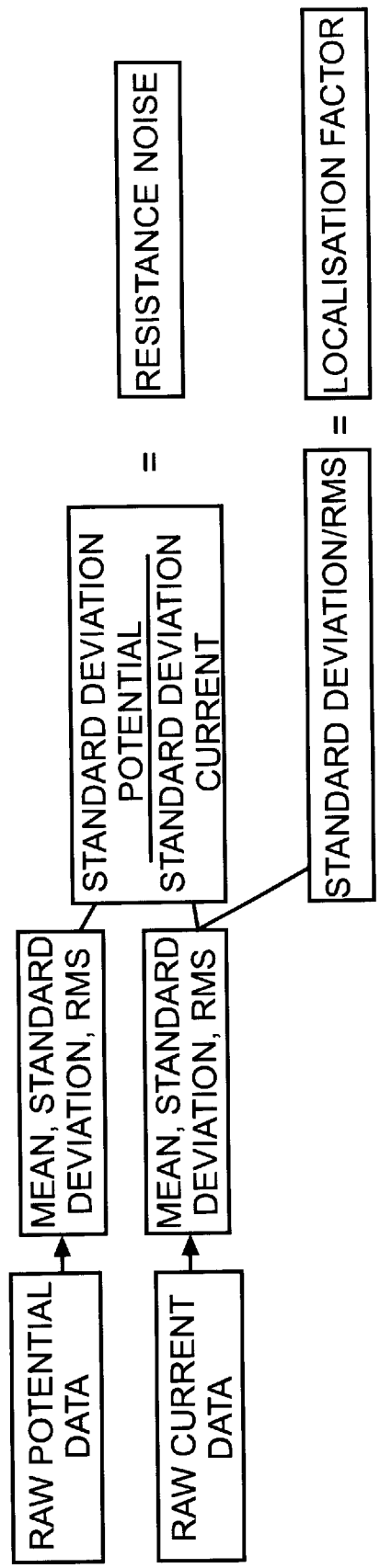
FIG. 5 is a schematic representation of the steps taken to calculate resistance noise values.

FIG. 5 shows schematically the steps taken to calculate the resistance noise value. This is inversely proportional to the corrosion current thus the general corrosion rate. The localization factor is used to give an indication of the stability of the corrosion process and may also be used to identify if localized corrosion is likely.

The processor 22 may be pre-loaded with a programme which will periodically read the values of potential and current from the A/D 20 and store them as a data file, for example, in memory 24. The same programme may be used to calculate the values of resistance noise and localization factor as described above, with reference to FIG. 5.

The data may be analyzed on-line using batch analysis, moving window or discounted filtering techniques.

Batch Analysis.

Raw time record data is obtained as digitised signals which represent the potential and current signals from the freely corroding specimens; the raw data is typically collected at intervals of one second. The mean, standard deviation, and higher moments of the digitised signals are computed for time record lengths of typically between 30 to 2048 points. Nomalization of the raw signals may also be carried out, involving removal of the mean and normalization to one standard deviation, this routine allows direct comparison of data sots from a variety of electrochemical noise from different sources. In addition the calculation of the Skew and Kurtosis of the signals can be undertaken for comparison with known patterns of behaviour from different corrosion mechanisms.

Moving Window.

Alternatively the data can be treated using a moving window, of between 30 to 2048 points, and recalculating the statistics with each new data point.

Discounted Filtering

Discounted filtering techniques are probably the most efficient in terms of use computing power. The raw data is read in periodically and typically at rates of every 1 or 2 seconds and a series of calculations are carried out to calculate the moments of the data, and hence the skew and kurtosis values.

For example, the following steps may be used:

1. Raw data
2. Calculate running mean from $V_m = \lambda V_{m-1} + (1-\lambda)V_t$, where $\lambda$ is the discounted filtering coefficient, with values between 0 and 1, depending on the relative weighting required for the past and present values. $V_m$ is the new value of the running mean, $V_m-1$ is the previous value of the running mean, and $V_t$ is the new raw data value.
3. Calculate $(V_m-V_t)$, no discounted filtering
4. Calculate $(V_m-V_t)^2$, with discounted filtering—equivalent to calculating M2 variance
5. Calculate $(V_m-V_t)^3$, with discounted filtering—calculates M3
6. Calculate $(V_m-V_t)^4$, with discounted filtering—calculates M4
7. Calculate $M3/M2^{1.5}$ skewness
8. Calculate $M4/M2^2$ kurtosis M1—the first moment is the average or mean value of the data, and is the equivalent to dividing the sum of all sample values by the number of samples in the data.

The variation of the data around the mean is usually described in terms of M2—the second moment, also called the variance. The standard deviation is the square root of the variance. The variance may be calculated by taking the mean value (M1) away from each value, squaring the result, adding all values obtained and dividing by the number of samples in the data.

The third moment, M3, and fourth moment, M4, are calculated in a similar manner to M2, but instead of squaring the results of taking the mean value away from each value, they are instead raised to the powers 3 and 4 respectively, adding all values obtained and dividing by the number of samples in the data. The third and fourth moments are subsequently used to evaluate the data in terms of how the data distribution relates to, or deviates from, a normal distribution, usually by calculating a) the Skewness from $M3/(M2^{1.5})$—which indicates the positive or negative bias of the data; and
b) the Kurtosis from $M4/(M2^2)$—which indicates the "peakedness" of the distribution.

The values of the moments, etc., can be calculated using discounted filtering techniques as shown in steps 2 to 8 above.

Figure 2:
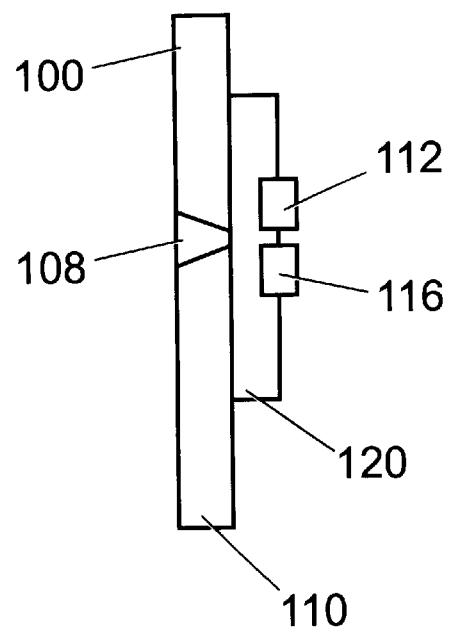
FIG. 2 is a schematic representation of how the electrodes of FIG. 1 may be configured in a typical application of the present invention.

FIG. 2 shows schematically how a typical corrosion system may be configured. In this case, a vessel wall 100 may be monitored for corrosion at, for example a weld joint 108. The vessel wall 100 constitutes the first electrode 110. The other electrode 112 of the pair is situated in close proximity to the weld 108 and is generally of the same material as the first electrode 110 (the vessel wall 100). The third electrode 116 is positioned in close proximity to the first and second electrode 110, 112. The electrodes 110, 112, 116 are all submerged in, or exposed to, an electrolyte 120.

A ZRA (not shown) and a voltmeter (not shown) are electrically connected to the electrodes 110, 112 and 116 as shown in FIG. 1. The system, as will be described hereafter, may be used to identify the corrosion mechanism which may be affecting the weld 108.

Under certain conditions the use of two electrodes which are not totally identical has been used for the electrode pair 10, 12. For example, in the case of stress corrosion cracking studies it is common to adopt an approach which involves stressing only one of the working electrodes such that the electrochemical signals which are generated may be correlated with a mechanism which indicates that the stress has an influence on the corrosion process.

Figure 3:
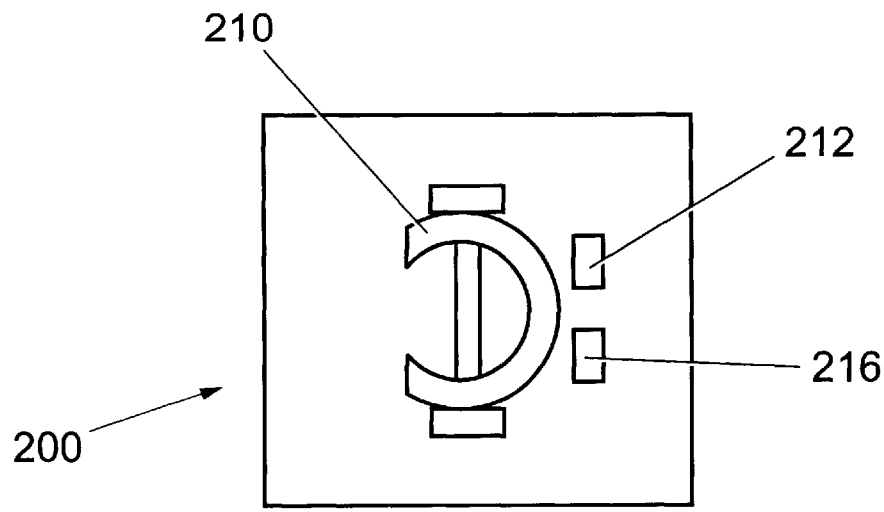
FIG. 3 is a schematic representation of an alternative electrode configuration of FIG. 2.

FIG. 3 shows a typical arrangement 200 which may be used to assess the effects of stressing one electrode 210. As with the previous configurations, a ZRA (not shown) is electrically connected between the first electrode 210 and the second electrode 212, and a high-input impedance voltmeter is electrically connected between the second electrode 212 and the third electrode 216. The system 200 is immersed in an electrolyte and the current and potential generated by the corrosion mechanism is monitored as will be described hereafter.

A similar approach may be used to assess the susceptibility of a material to crevice corrosion, using one creviced and one non-creviced sample for the working electrodes.

Figure 4:
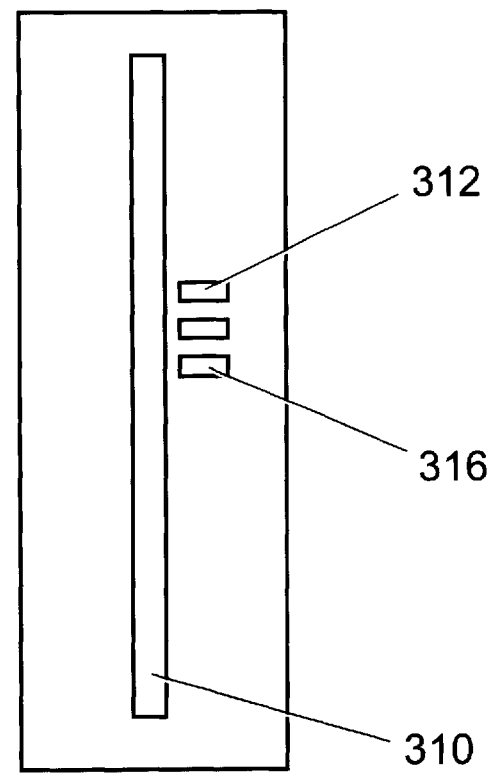
FIG. 4 is a schematic representation of a further alternative electrode configuration of FIG. 2.

FIG. 4 shows an alternative arrangement where a reinforcing bar in concrete constitutes the first electrode 310 and the second and third electrodes 312, 316 are used to provide the current and potential values of the electrochemical noise. This system may be used to measure the corrosion rate and mechanism which the reinforcing bar is subject to.

However, in order to identify the corrosion mechanism, further processing of the values stored in the memory 24 is required. The electrochemical potential and voltage signals, stored as a data file in the memory, arise from a wide variety of corrosion mechanisms and thus cover a large dynamic range. It is therefore difficult to compare data files from different sources, such as electrodes of different metals, directly. To compare the data from different sources, normalization routines have been used to allow such comparisons to be made.

Initially, the mean value of the potential and current is subtracted from the measured value, and this is then divided by one standard deviation of the current or potential. The mathematical formulae for this is given below:

$$V_N = \frac{(V_t - \overline{V})}{\sigma_v}$$

where:

$V_N$ is the normalised potential $V_t$ is the potential at time t $\overline{V}$ is the mean potential $\sigma_V$ is the standard deviation of the potential $$I_N = \frac{(I_t - \overline{I})}{\sigma_I}$$

where:

$I_N$ is the normalised current $I_t$ is the current at time t $\overline{I}$ is the mean current $\sigma_I$ is the standard deviation of the current Further data treatment may involve the use of trend removal if the current and potential signals drift significantly during the monitoring period, as will be appreciated by those skilled in the art.

Figure 6:
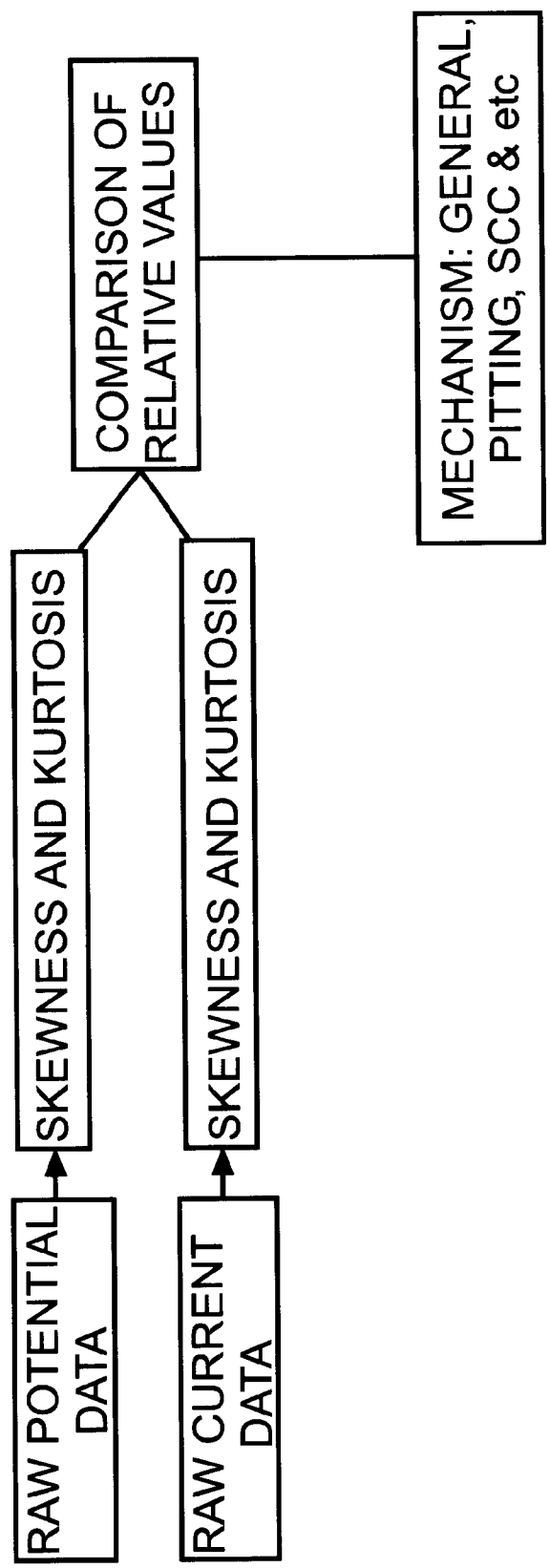
FIG. 6 is a schematic representation of the steps required to calculate the skewness and kurtosis of raw potential and current data to identify the corrosion mechanism.

The next stage is to calculate the kurtosis and skewness of the statistical distribution of the potential and current values. A simplified schematic illustration of this is shown in FIG. 6. Calculation of these statistical values allows the data files from different sources to be directly compared and the values can be used to identify the corrosion mechanism as will be described.

The kurtosis values calculated by the processor 22 may be used to identity if there is a high probability of localized corrosion. For localized corrosion, the Kurtosis values would be large, positive values for both the current and potential signals, as shown in the table below. For general corrosion however, these values would be small or negative numbers. The skewness values of the potential and current distribution may be used as a cross-check to the above.

|  | Potential | | Current | |
|---|---|---|---|---|
| Mechanism | Skewness | Kurtosis | Skewness | Kurtosis |
| General | <±1 | <3 | <±1 | <3 |
| Pitting | <−2 | >>3 | >±2 | >>3 |
| Transgranular SCC | +4 | 20 | −4 | 20 |
| Intergranular SCC (#1) | −6.6 | 18 to 114 | +1.5 to +3.2 | 6.4 to 15.6 |
| Intergranular SCC (#2) | −2 to −6 | 5 to 45 | +3 to +6 | 10 to 60 |

For localized, or pitting corrosion, it can be seen from the table above that the value of the potential kurtosis is typically very much greater than 3 and the potential skewness is greater than −2. The signs and quantity of the current skewness and/or kurtosis may be used as a cross-check to ensure that localized corrosion is present.

Furthermore, the value of the current or potential Kurtosis may be used to derive a notional probability of localized attack using the following formula:

$$\text{Localisation} \cong \exp\left(\frac{-3}{\text{abs(Kurtosis)}}\right)$$

Having evaluated the skewness and kurtosis values for a particular system using the procedure outlined above, the data can then be compared against known outputs from various corrosion mechanisms. This will provide an output which relates to the probable corrosion mechanism. The comparison may be made using an expert systems approach, or alternatively, a pattern recognition technique. These techniques allow the data to be analyzed consistently, without having to rely on the expertise of personnel who have many years experience in interpreting such data. A typical technique which may be used is neural networks.

Existing corrosion monitoring process takes the form of on-line processing of free floating Current and Potential raw data signals. Statistical analysis is performed on these results along with the "eyeballing" (visual determination) of the trends in the data with a view to determining:

a) Corrosion Mechanism; and b) Corrosion Rate.

The object of the Neural Net will be to take the expertise out of and give a higher confidence in the determination of (a), with a view to improving estimates of (b). The end result would ideally signal an alarm or barchart on-line, particular to one of the corrosion processes.

Data Collection

The main bulk of data used for training the net was created with the use of a three electrode test cell (similar to that shown in FIG. 1). The electrodes were made out of various metals, each of which has a higher probability of inducing a particular mechanism in conjunction with specific corrosion activators.

Files were obtained at one second resolution for representative corrosion systems:

General corrosion (GC)

Pit initiation (PI)

Pit propagation (PP)

Transgranular stress corrosion cracking (TGSCC)

Intergranular stress corrosion cracking (IGSCC)

Statistical Pre-Processing

The second method selected for data pre-processing was Skewness and Kurtosis.

The Kurtosis categorizes the relative peakedness or flatness of the distribution of the dataset compared to that of the normal distribution. Positive Kurtosis is indicative of a relatively peaked distribution while a zero or negative Kurtosis indicates a relatively flat distribution. This will indicate the number and frequency of transients contained within the dataset.

The Skewness characterizes the degrees of symmetry of the distribution of the dataset around the mean.

No Skew equates to an even distribution of the dataset around the mean. Negative skew indicates that the data is more negative in relation to the mean (more of the data is below zero in the normalized form). Positive skew indicated that the data has a more positive distribution around the mean.

This function will give an indication as to the direction and width of the transients in the dataset. If the transients are abrupt but non frequent then the data will be skewed in the direction opposite to direction of the transients; the skew will however be relatively small because of the sharpness of the transients. If the transients are sharp but longer lived, the skew will give a higher value in the opposite direction of the transients. This is because the broader transients force the mean to go higher, resulting in the baseline data being more negative in relation to the mean.

These statistics in conjunction with each other give a good indication of the mechanism present in the dataset. The statistics are performed on relatively small sections of the raw data file to ensure that all mechanisms within the file are accounted for.

The memory of a neural network is unlike that of conventional computer programmes; it takes the form of a threshold value for each of the neurons, along with a weight for each of the inputs to that neuron.

Figure 7:
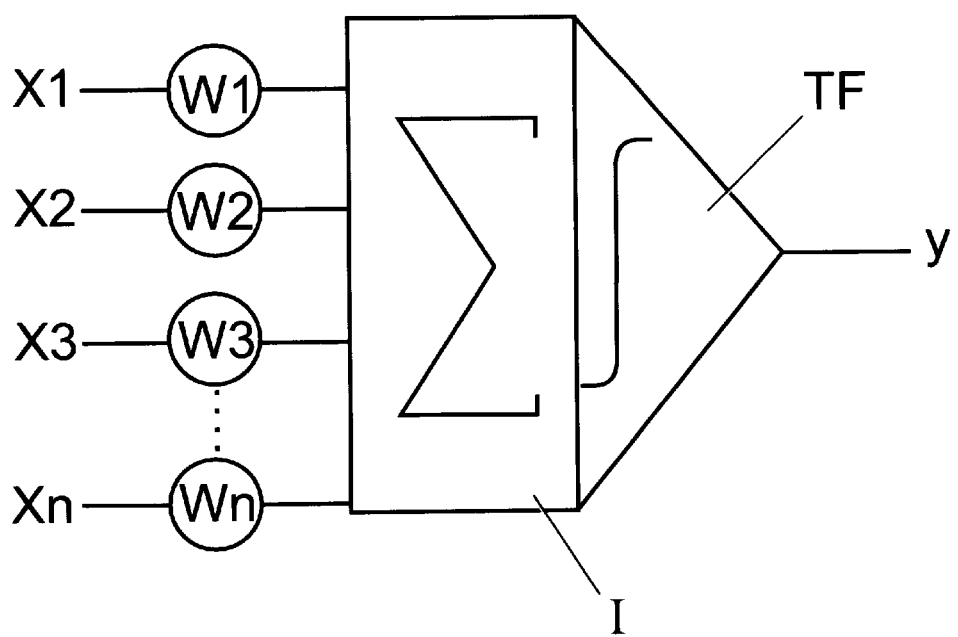
FIG. 7 is a schematic representation of the basic principle of neuron firing.

Referring to FIG. 7, the basic principle of the neuron is that the input value $X_n$ is multiplied by the weight value for that input $W_n$. In the most common network architectures, the input signals $X_n$ are combined by a simple summation $I=\Sigma(W_n X_n)$. The result of the summation is the activity level of the neuron. This activation is then tested against a threshold value T. If the summation input value I exceeds the threshold value T, this will force the neuron to accept the input and fire. The transfer function TF will modify this activation to calculate an output for the neuron (such as Sigmoid, TanH etc.). The firing neuron then outputs a value y to all connected neurons in the next layer or as a final output. These processing elements or neurons are grouped together into layers as required. The layers are then grouped together to solve more complex problems.

Training the net is the procedure to modify the weight/threshold combinations of certain neurons to fire for certain input patterns. This procedure will force different neurons to fire for different input patterns, giving the net an internal representation of the inputs. The network can then be trained to fire in certain combinations for specific differences in the input data $x_n$, thus for this example firing different neurons in the output layer with more emphasis (higher output value) for specific patterns than it would if the pattern(s) were not present at input.

Learning Rules

The network is not programmed as in conventional computing but trained. The training is a method of altering the weight/threshold combinations to give the network an internal representation of the input pattern presented to it during training.

The two most fundamentally different types of Neural Network learning methodologies are that of Supervised and Unsupervised learning. The former is a method of learning whereby the results of classification of the data are already known and given to the network at training time. This data is then taken into consideration in the training of the net. The input data $X_n$ is tested for the most predominant features present for the output of one category that are not present in the data used to train for the remaining output categories. Unsupervised learning does not know the desired results at training time. With Unsupervised learning and the classification problem to which this description applies, the net would search through the training data and find n (n=no of outputs) features or combinations of features that are present in the input data $X_n$ for one output and not present or different for all other outputs. This description will focus on the supervised learning method as this is believed to be of greater relevance to the problem at hand. The outputs are known and the problem is one of categorization of the known signatures in the input data.

Within the field of Neural Networks the main requirement is to allow the network to learn so as not to forget what it has previously been taught or learnt. This function is called convergence; all network learning rules must comply with this prerequisite. There are several algorithms for training neural networks each depending upon the network architecture and the application required. Once a learning rule has been chosen, functions may be applied to the transfer function of the neuron to give a certain amount of customization depending upon the application to which you are applying the network. In this particular application a derivative of the Widrow Hoff or "Delta" learning rule will be used. This rule is a method of reducing the error of the network proportional to an arbitrary error correction value.

101.1 Delta Rule with the MCP Network

In this example the McCulloch & Pitt's network (MCP) will be used. This is a feed-forward network in which for any given input, the output must be known to allow the reduction of error inequality between any given input and its associated output.

In simplified terms the Delta rule works by following the steps listed below.

1. Select a column within the truth table.
2. if this column is erroneous, calculate the distance between the actual summation of the MCP node to that required to satisfy the desired firing rule.
3. Adjust the weights that are live (have firing inputs) along with their associated threshold values to remove a portion "e" of the error.
4. Repeat steps 1 to 3 until the firing rules have been satisfied and the output of the truth table is as required.

To use this method a truth table must be selected, along with a randomly initialized MCP (McCulloch & Pitts) node. The truth table is simply an example, although as will be discussed later, certain truth tables cannot be satisfied with the MCP network because they are not linearly separable.

Initial randomly chosen neuron state:

$W_1=+0.2$ $W_2=-0.5$ $T=+0.1$ where $W_1$=Weight associated with the input $X_1$ to the neuron (node).

$W_2$=Weight associated with the input $X_2$ to the neuron (node).

T=Threshold associated with the node.

Table 3.1 below is a truth table which is implied by the current weight/threshold values, where F represents the firing of a neuron.

TABLE 3.1

Truth table implied by current weight/threshold values.

| X1 | 0 | 0 | 1 | 1 |
|---|---|---|---|---|
| X2 | 0 | 1 | 0 | 1 |
| F  | 0 | 0 | 1 | 0 |

Table 3.1 Truth table implied by current weight/threshold values.

Table 3.2 below is the truth table required as the final output from the net, where F is as before.

TABLE 3.2

Truth table required as the final output from the net.

| X1 | 0 | 0 | 1 | 1 |
|---|---|---|---|---|
| X2 | 0 | 1 | 0 | 1 |
| F  | 1 | 1 | 0 | 0 |

Table 3.2 Truth table required as final output from net.

The inequality rule, or firing rule associated with the MCP net is:

$\Sigma W_i X_i > T$ where $W_i$=Weight associated with input i $X_i$=Value of input i T=Threshold value This means that in this example $W_1 X_1 + W_2 X_2$ must be greater than T for the node to fire (become 1). Referring to Table 3.1 above, it can be seen that the first column is erroneous i.e. (0*0.2)+(0*(−0.5)<T. Thus, step one of the Delta rule is invoked to establish the distance between the output of the summation and the required output. In order to do this a set of variables is introduced, which are defined as follows:

E=The error between the output of the summation and the Threshold value of the node.

e=The amount by which E must be surpassed before the node is allowed to fire.

δ=The portion of the error that we wish to remove.

Both e and δ are chosen arbitrarily and altered as a matter of experimentation.

For this example arbitrary values of δ and e are chosen at 0.5 and 0.1 respectively. With all of the variables for the Delta rule set up and the required truth table established, along with an associated randomly initialized node, the weights and thresholds associated with this node may be optimized to satisfy the truth table (table 3.2 above). This is done by following the iteration steps previously laid out. Table 3.3 below shows the Delta rule calculations made.

TABLE 3.3

Delta rule calculations made.

| Column in error | Error E | Correction factor (E + e)/2 | New W1 | New W2 | New T |
|---|---|---|---|---|---|
| 0.0 | 0.1 | 0.1 | — | — | 0 |
| 0.1 | 0.5 | 0.3 | — | −0.2 | −0.3 |
| 1.1 | 0.3 | 0.2 | 0 | −0.4 | −0.1 |
| 1.0 | 0.1 | 0.1 | −0.1 | — | 0 |
| 0.1 | 0.4 | 0.25 | — | −0.15 | −0.25 |
| 1.0 | 0.15 | 0.125 | −0.225 | — | −0.125 |
| 0.1 | 0.025 | 0.0625 | — | −0.0875 | −0.1875 |

Table 3.3 Delta Rule Calculations

Note that the correction factor is continuously reducing in size. This is called convergence. The reason for the small steps in reduction is to reduce the possibility that a change in the vectors for one output force an error in the calculation for another output. The weight/threshold combinations are being adjusted continuously until a set of values is reached that satisfies all criterion.

101.2 Linear Separability

Figure 8:
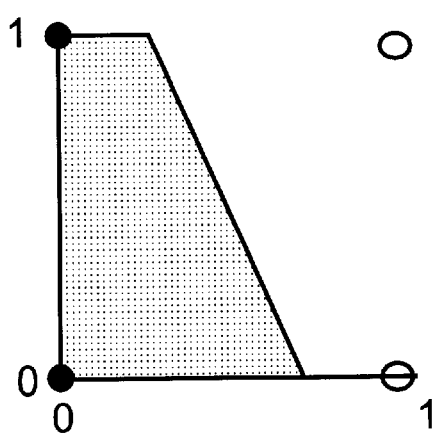
FIG. 8 is a linear separability diagram for the truth table shown in Table 3.2.

The MCP net does have the prerequisite that the required truth table be linearly separable. That is, a if the truth table were drawn geometrically the results of the net when the neuron is required to fire must be separable from those in a non-firing state by one line in the geometric two or three-dimensional space. That is, for table 3.2 above, the linear separability diagram would be as shown in FIG. 8.

For more than two inputs, the same applies in Euclidean space. That is, table 3.4 below is the truth table for a three input neural net.

TABLE 3.4

Three input truth table example

| X1 | 0 | 0 | 0 | 0 | 1 | 1 | 1 | 1 |
| X2 | 0 | 0 | 1 | 1 | 0 | 0 | 1 | 1 |
| X3 | 0 | 1 | 0 | 1 | 0 | 1 | 0 | 1 |
| F | 0 | 0 | 1 | 0 | 0 | 0 | 1 | 0 |

Table 3.4 Three Input Truth Table Example

Figure 9:
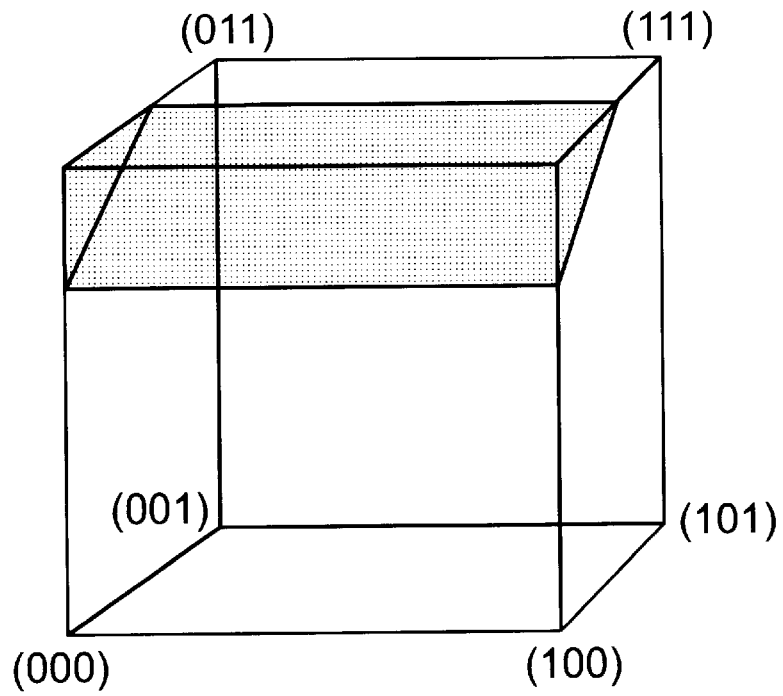
FIG. 9 is a three-dimensional separability diagram for the truth table shown in Table 3.4.

This results in a three-dimensional linear separability diagram as shown in FIG. 9.

There are ways around the problem of linear separability with the introduction of a hidden layer which will be discussed later.

101.3 The Hard Learning Problem

Networks such as the MCP network and other networks suffer from a problem called "hard learning". The networks find it impossible to distinguish between specific types of shape in the input pattern. These shapes are:

Parity;

Connectivity; and

Symmetry.

The exclusive-or (XOR) problem as discussed earlier is a case of a parity problem. FIG. 8 shows that the XOR is not linearly separable. This problem may be solved with the introduction of extra neurons. The Parity function is attempting to get the network to fire if the number of inputs in the input image or truth table is odd.

Connectivity is when the network is attempting to fire if all of the inputs are linked together i.e. there are no isolated inputs.

Symmetry is a problem in which the input image is symmetrical around the centre point.

Network Architectures 101.4 The HOPFIELD Model

The HOPFIELD model is concerned with content addressable memory, i.e. addressing a variable by its contents (A="Steve Reid"; addressed by "Steve Reid"). As with the MCP Model a neuron has two states; that is a 1 or 0, where $V_i=1$ if firing and 0 if not. The HOPFIELD model can be described as more appropriate to pattern completion than pattern recognition. With this model, the inputs are used for both inputs and outputs; therefore it is possible to complete partial inputs. This type of network could be used for creating spell checkers or other such applications, whereby partial or incorrect information may be given and an interpretation/correction of the input is required. It is included in this description as an introduction to temperature with simulated annealing and hidden nodes (discussed later).

Figure 10:
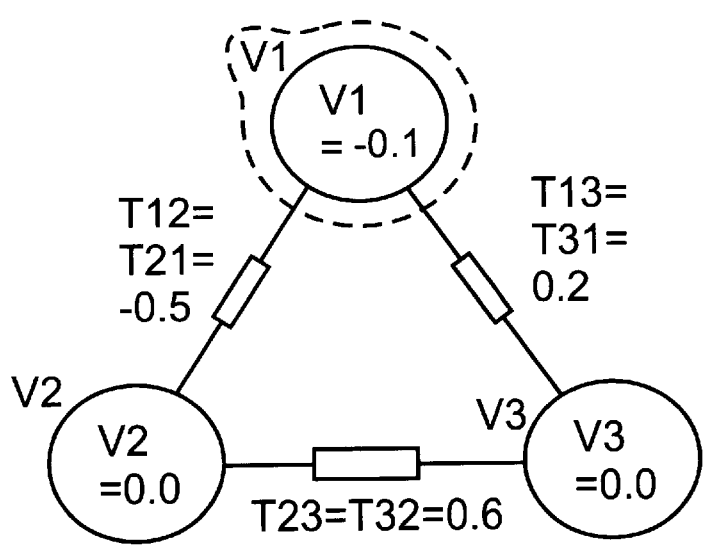
FIG. 10 is an example of a randomly initialized Hopfield network.

FIG. 10 shows an example of a randomly initialized HOPFIELD network. With the HOPFIELD network there is no set pattern as to which neuron will fire or attempt to fire first. Each neuron has an equal probability of being next in the firing list. The important function of this network is the bi-directionality of the connection strengths i.e. T12 is used as a weight in the previous net examples for calculating V2's input into V1 as well as V1's input into V2. The activation function (function that tests if the neuron should fire or not) for this network is displayed below:

$V_i$ fires (becomes 1) if $$\sum_{j>i} T_{ij} V_j > U_i$$

The object of this network is to try and get the input to settle in one of the trained settled states. Therefore, if the network of three neurons were trained with two settling states 001 and 011, the network would attempt to settle in a state with the smallest hamming distance from the initial input state i.e. if 111 were input, the network would tend to settle in the state 011. Hamming distance is the distance between two states of input i.e. 110 is closer to 111 than it is to 001, therefore the hamming distance would be smaller.

The network has associated with it an energy value E.

Every time the network changes state this energy value can only either stay the same or get smaller (ΔE must be negative). When there are no more lower energy states that the network can reach from its present state, then the network becomes stable in its present state. This reduction trend with the network energy is enforced by the activation function. This rule ensures that the network alters state in an irreversible manner (energy calculations mean that it does not revert back to a previously experienced state).

102.2 Energy Wells

The settled state(s) of a HOPFIELD network are referred to as Energy Wells (the network has settled in a state out of which it cannot get because ΔE would be positive with all possible changes in $V_i$). These energy wells are created either by design or erroneously. It is possible that the network would create a series of energy wells which did not correspond to desired settling states (false minima). These wells are however used to design settled states within the network and created purposely by either calculation or training. If for example both the states 010 and 111 were required to be stable, the solution below satisfies the inequalities and results in the wells 010 and 111 (see FIG. 10).

| T12 = 0.2 | T13 = 0.5 | T23 = 0.2 |
| U1 = 0.3  | U2 = =0.1 | U3 = 0.3  |

This solution does however produce a false well of 100. Therefore states 000 and 110 all have equal probability of falling into either state 010 (required) or 100 (false well). This is something that can be overcome with the introduction of simulated annealing as discovered by Hinton which will be discussed later.

Values have to be found for the six unknowns (weight/threshold combinations) that satisfy the restrictions implied by all required states. These can be found by either training or calculation. The Delta rule can be applied to the HOPFIELD model to gradually adjust the strengths and weights until the required wells are created.

This type of network does however still suffer from the Hard learning problems identified earlier. A network architecture called the BOLTZMANN machine overcomes these problems along with the problem of false wells.

102.3 The BOLTZMANN Solution

Figure 11:
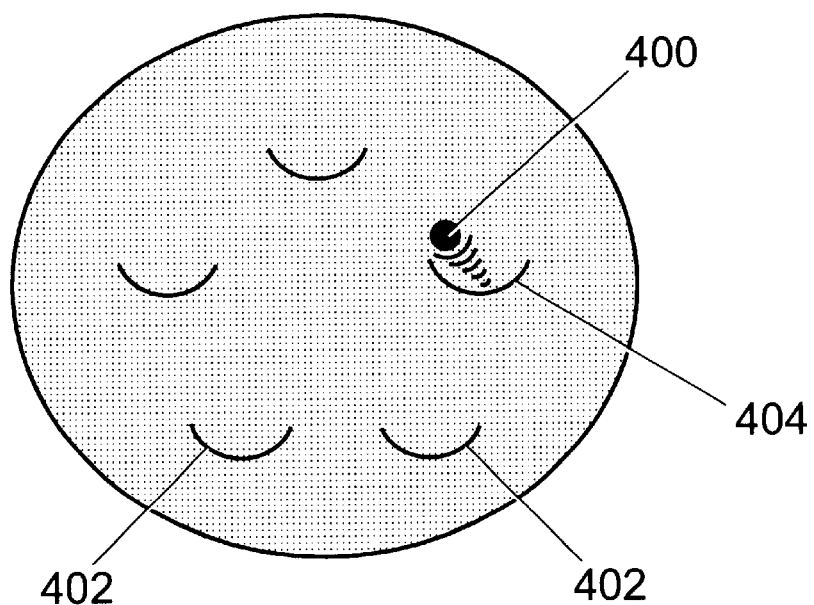
FIG. 11 is an analogy of noise in a Hopfield network.

Hinton and his colleagues in 1986 added noise to the HOPFIELD network and called it the Boltzmann Machine. This lead to better control of energy minima (false wells) and provided a solution to the hard learning problem. Noise is a method whereby a degree of uncertainty is added to the energy of a state, thus allowing the network to re-consider its position and in essence jump out of a false settled state. FIG. 11 is an analogy of noise in the HOPFIELD network.

The analogy in FIG. 11 is analogous to games whereby a ball 400 has to land in one of the lower loops 402. If the ball 400 lands in an upper loop 404, giving the game a slight "jog", thereby exciting the ball 400 allows it to jump out of the position in which it had settled.

Ludwig Boltzmann discovered in the 19th Century that the introduction of temperature into electronic circuitry which carries current caused a transformation of the smooth waveforms into rough ones. This is why the network is called the Boltzmann machine as Hinton introduced a temperature variable into the argument.

The energy of the net at any state is given a degree of uncertainty above and below that which may be calculated. This uncertainty is called the "temperature" of the net. At a temperature of zero, the net would behave exactly as the HOPFIELD model. At higher temperatures, an uncertainty proportional to the temperature value is introduced. The method of controlling this temperature and its value is called "simulated annealing".

In a metallurgical sense, annealing is a process to take the stresses out of the metal. A sample of metal is heated until near melting point and then gently brought back down to ambient temperatures to allow the molecules to relax. If the metal is cooled too quickly, then the outer surfaces of the sample is cooled, whilst the inner material remains hot, causing the metal to crack due to the temperature differences in the material.

In a neural network the temperature must also be brought down gently. This allows the net to learn to avoid false wells at a higher temperature when it is able to get back out of them when encountered. If the temperature is brought down too quickly then the net may be settled in false minima at the point when the temperature is abruptly brought down. It will therefore be locked in this state for future iterations of the same input data. This method has been practically used to compute problems with many variables (many variables is proportional to more possible states of false minima). The higher the temperature, the greater the effect on the firing rule as shown in FIG. 12, which shows the effects of temperature on the firing probability.

Hinton proposed a now learning rule to create absolute minima, as well as being capable of dealing with "hidden" nodes. This net is capable of solving the Hard Learning problems.

Figure 12:
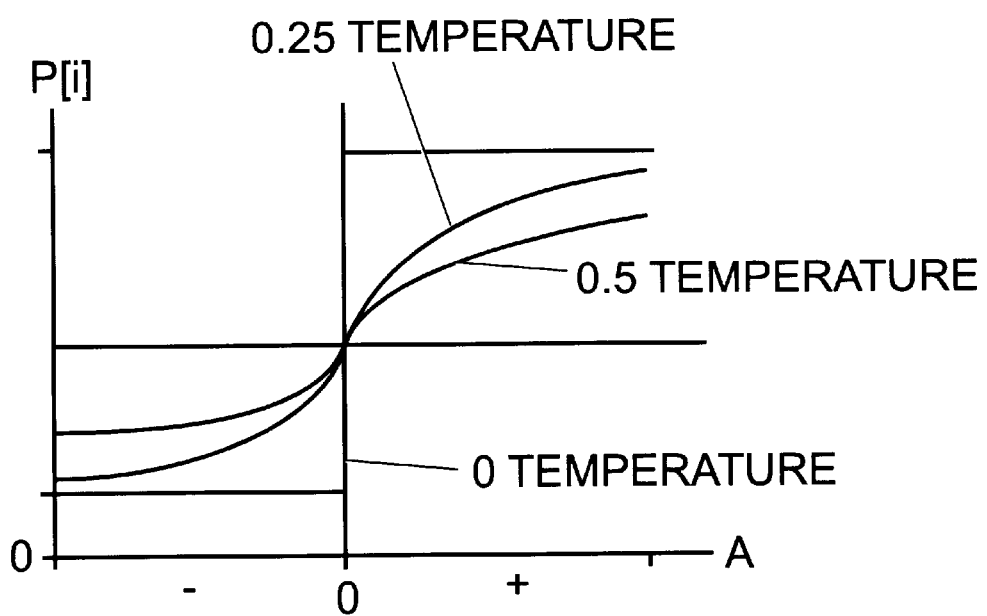
FIG. 12 is a diagram showing the effects of temperature on the firing probability of a neuron.

In FIG. 12,

P(1)=1=certain firing

P(1)=0=no chance of firing

So with a temperature of 0.5, if a node has a positive activation (A>0), it does not necessarily mean that this node will fire.

The Boltzmann Firing Probability Function (BFPF) is:

$$P(1)=1/(1+e^{-(A/T)}) \quad \text{Equation 3.2}$$

where:

P(1)=probability of firing.

P(0)=probability of not firing, that is (1−P(1))

A=Activation

T=Temperature 102.4 Hidden Units and the Boltzmann Machine

For the Boltzmann machine to be able to cope with the parity function there needs to be a hidden unit added to the network. An example of the parity function is shown in table 3.5 below. This table contains the stable states required of the network. As can be seen in table 3.5, for one of the nodes to fire, the other two inputs must be odd.

TABLE 3.5

| Parity function table | | |
| --- | --- | --- |
| V1 | V2 | V3 |
| 1 | 1 | 0 |
| 1 | 0 | 1 |
| 0 | 1 | 1 |
| 0 | 0 | 0 |

Table 3.5 Parity Function Table

Figure 13:
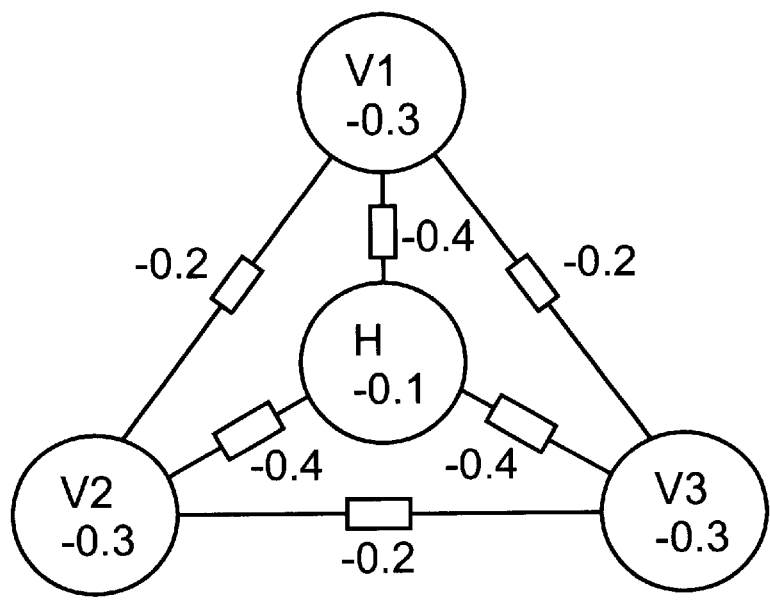
FIG. 13 is further example of a Hopfield network with a hidden layer.

Both the MCP and Boltzmann networks cannot do this hard learning problem. The introduction of a hidden unit H shown in table 3.6 (which is the parity function table of table 3.5 with a hidden unit H to resolve the hard learning problem) and FIG. 13 show how this can be resolved by removing the need to fire only on odd inputs.

TABLE 3.6

Parity function table including a hidden unit to resolve the hard learning problem

| V1 | V2 | V3 | H |
|----|----|----|---|
| 1  | 1  | 0  | 0 |
| 1  | 0  | 1  | 0 |
| 0  | 1  | 1  | 0 |
| 0  | 0  | 0  | 1 |

Table 3.6 Parity function table including a hidden unit to resolve the hard learning problem.

This network will work for all of the requirements in table 3.6. Below is an example of the row with requirement of 1100 including the hidden layer to get around the parity problem.

A1=(1*(−0.2))−(−0.3)=0.1 (therefore next value of V1 will be 1)

A2=(1*(−0.2))−(−0.3)=0.1 (therefore next value of V2 will be 1)

A3=(1*(−0.2))+(1*(−0.2))−(−0.3)=−0.1 (therefore next value of V3 will be 0)

A4=(1*(−0.4)+(1*(−0.4))−(−0.1)=−0.7 (therefore next value of V4 will be 0)

The problem during training is that only the desired values for the visible nodes are known. The training must somehow ensure that hidden units develop the correct weights and thresholds. None of the previous techniques would perform this function. Hinton and Sejnowski developed a function to do this.

Error Back Propagation

Figure 14:
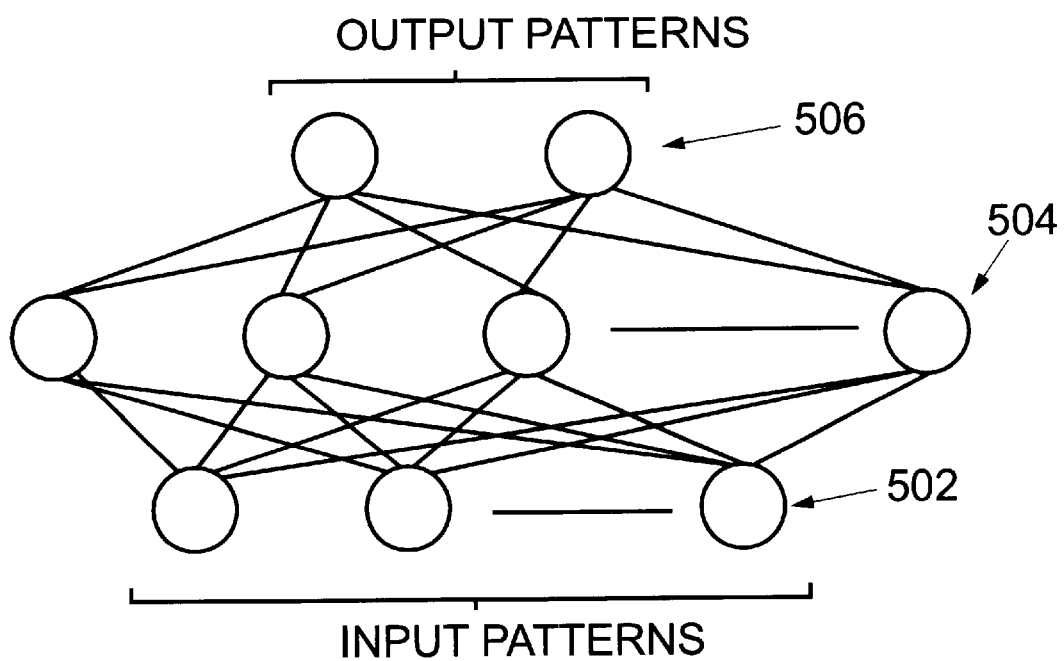
FIG. 14 is an example of a feed forward network.

The problem of hard learning can be solved with the introduction of hidden units; error back propagation is a method of training these units. Back propagation is one of the most widely used neural network architectures and is ideal for the problem of pattern classification. Unlike the networks described earlier with this type of network there is no prerequisite that all nodes be interconnected. Back propagation is a simpler way of establishing a relationship between a definite input and a definite output. FIG. 14 shows a feed forward net comprising an input layer 502, a hidden layer 504 and an output layer 506. All outputs from the input layer 502 are coupled to the hidden layer 504, and all outputs from the hidden layer 504 are coupled to the output layer 506. The net shown in FIG. 14 is a feed forward net which works by controlling the training of the hidden units in the hidden layer 504 by a process of propagation of measured errors from the given output to the required output in the output layer 506. The hidden layer(s) 504 is a place in the network where the data is partially labelled or categorized before the output layer 506 comes to the final decision. This layer is described as storing "internal representations" of the training set that are not provided by the trainer.

The network shown in FIG. 14 uses a generalized version of the Delta training rule:

$$-\overline{O_{pj}} = \overline{f_j(\alpha_{pj})}$$

where:

$$\overline{\alpha_{pf}} = \sum_i \overline{W_{ji}O_{yi}} + \overline{U_j} = \text{activation of the } j\text{th node for the } P\text{th training example}$$

$\overline{f}$=As yet unspecified function of the activation
$\overline{W_{ji}}$=Weight connecting nodes j and i
$O_{pi}$=Output of the ith node connected to the jth node
$\overline{U_j}$=Threshold for the jth node The error, measured by $O_{pj}$ compared to the desired output value, is used to determine the weight changes proportional to taking a percentage of the error away on each training cycle. This procedure is started at the output layer and propagated through the layers to the input layer.

Corrosion

The data used to analyze corrosion and its mechanism is gathered in real time, usually by using a three electrode probe (such as that shown in FIG. 1) made from metals obtained from a pipeline or on site. In the case of the data monitored for the purpose of this description, a three electrode cell was used. The electrodes used were customized to instigate the corrosion mechanisms required to train the network.

Mechanisms

There are four main categories of corrosion mechanism:

General

Pitting

Trans Granular Stress Corrosion Cracking (TGSCC)

Inter Granular Stress Corrosion Cracking (IGSCC)

Both Pitting Corrosion and SCC corrosion (both Trans Granular and Inter Granular) have the subsets:

Initiation

Propagation 110.1 General

With general corrosion it is possible to apply a set of rules as the process is not random. There are several methods within the field of Electrochemistry for determining the characteristics and severity of General Corrosion These methods are:

Stern Geary

This relates Polarisation resistance ($R_p$) to the Corrosion Current ($I_{corr}$)

Impedance

This also takes into account the Stern Geary constant

Linear Polarisation Resistance (LPR)

Harmonics

Polarization curves

This uses the Tafel technique to work out the $I_{corr}$

Electrochemical Noise

Microscopic's

The corrosion current is normalized to 1 cm² as electrodes of several cm² for general corrosion are typically used. For other mechanisms it would be advantageous to use a larger electrode as the other processes are not generally as easy to capture as they are more localised, and the probability of localized attack occurring on the electrode as opposed to the bulk material is relatively low. General corrosion is actually micropitting in a relatively uniform manner.

POISSON Process

Figure 15:
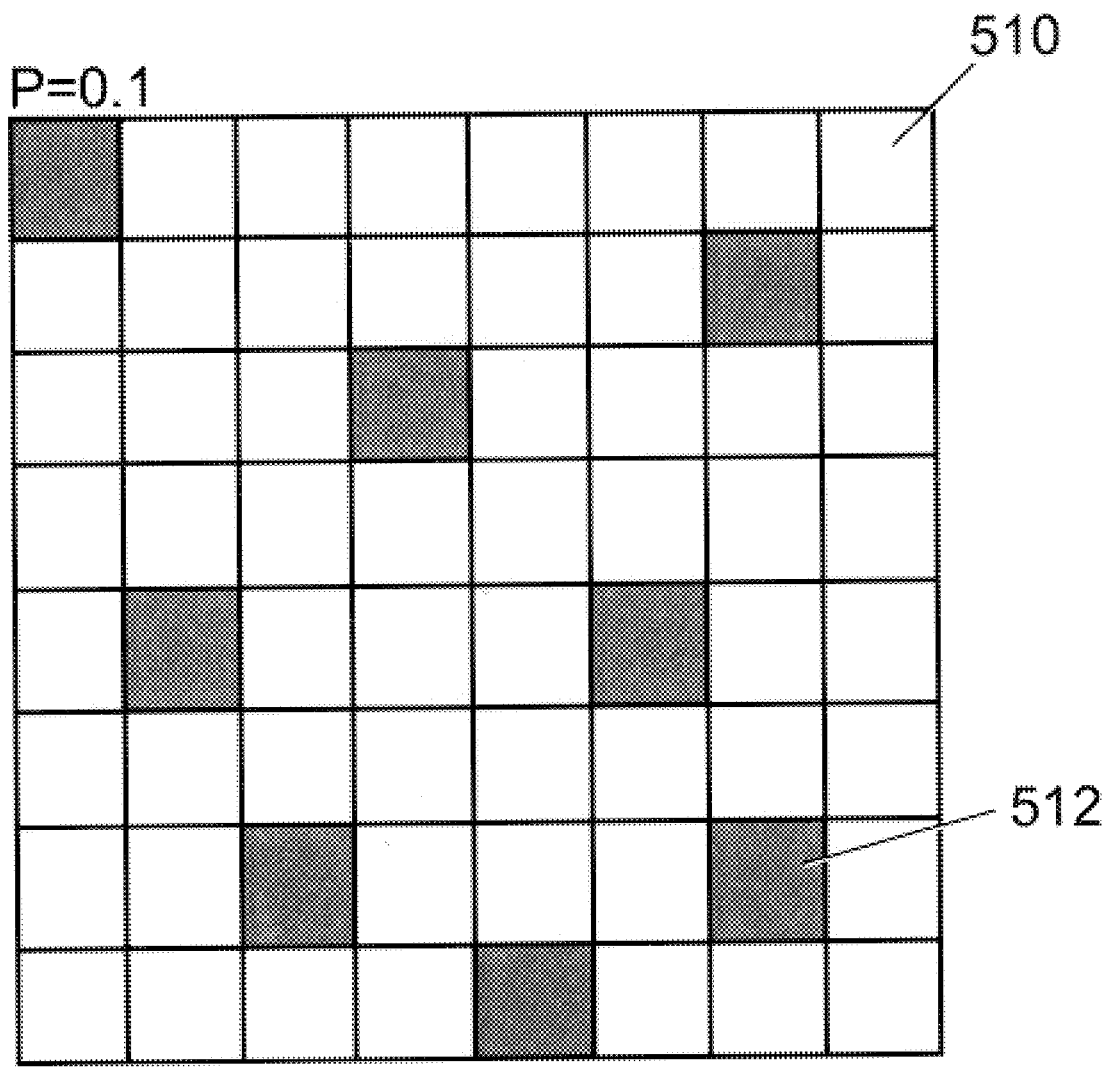
FIG. 15 is an example of a Poisson process.

FIG. 15 is an example of a Poisson process. Each of the squares 510 represents an ion, with the shaded squares 512 representing an oxidized ion. Some function of corrosion current is measured in a time period (t=1 sec), where p represents the probability that each of the above ions will be oxidized (corroded). In the next time period a number of metal atoms proportional to p will also become oxidized, thus doubling the effect of corrosion on the electrode.

The example in FIG. 15 has p=0.1 which relates to an average of 1 in 10 atoms oxidizing. In the next period t another 10 ions will oxidize according to p=0.1. This probability cannot exceed 1, and shows a random dissolution at a very fast rate.

Generally, groups of 1024 one second sample points are measured at a time, which establishes a trend to work with.

The measurement of general corrosion is normally done by using three identical electrodes wired to a logging base unit (see FIG. 1).

110.2 Characteristics

General corrosion is detectable in the time domain by both the current and potential traces containing positive and negative going current transients, similar to that of white noise. The potential transients are generally negative signifying systems that are in a passive or partially passive state, such that the overall general corrosion rate is low. The potential baseline will be higher with higher rates of corrosion.

Figure 16:
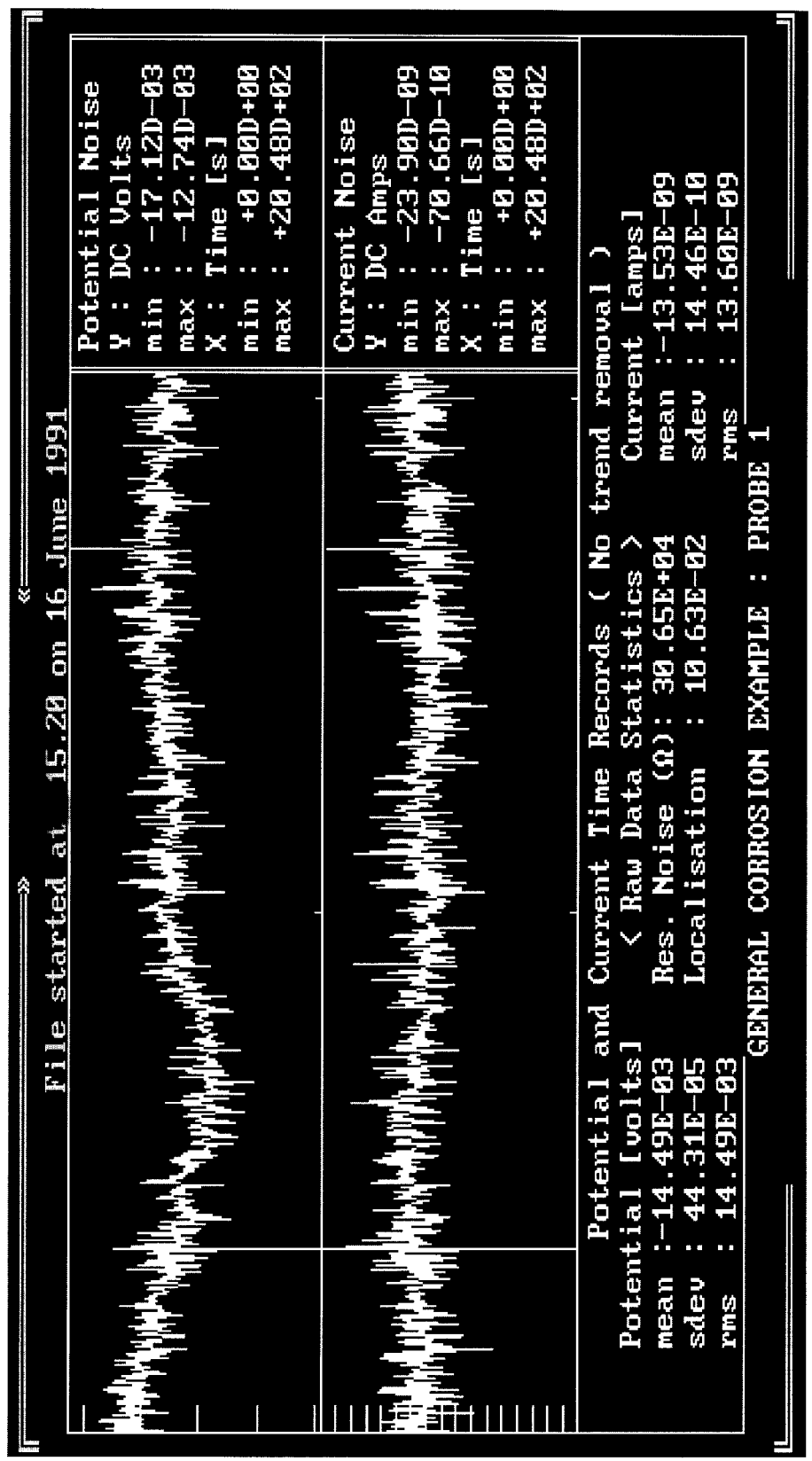
FIG. 16 is a typical electrochemical noise response for a system undergoing general corrosion.

FIG. 16 is an example of a general corrosion time trace which shows the bi-polar transients typical of general corrosion. The trace shown in FIG. 16 is typical of a noisy system.

110.3 Pitting

Figure 17:
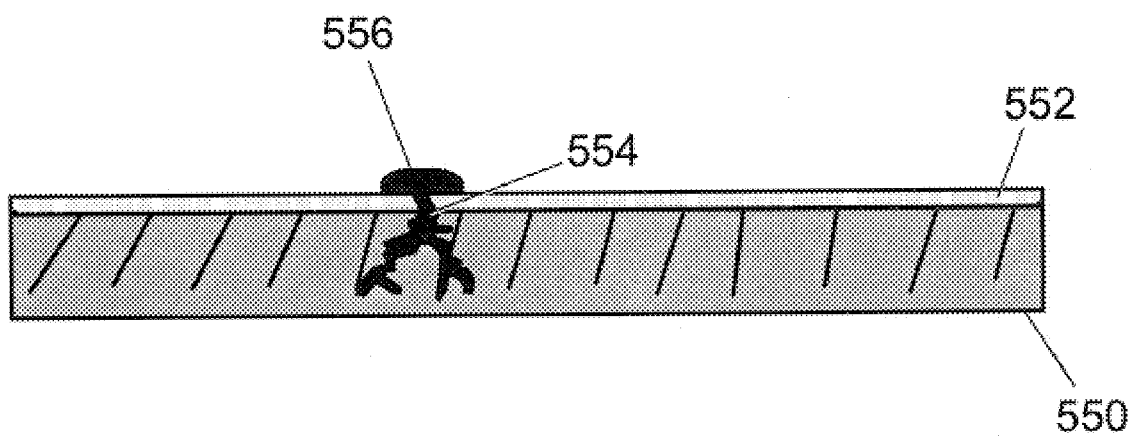
FIG. 17 is a schematic representation of an oxygen limiting process.

Pitting is more likely to occur in Stainless steel and other high alloy steels, as well as in inhibited carbon steels. With stainless and high alloy materials the passive film would be attacked, whereas with inhibited carbon steels the inhibited film is attacked. This is exemplified in FIG. 17 which shows schematically the oxygen limiting process. Referring to FIG. 17 there is shown a metal sample 550 which has an oxidized layer (or passive film) 552 on its surface.

Ruptures in the passive film 552 occur continuously (such as rupture 554) which re-passivates the film 552. However, starvation of oxygen due to a deposit 556 on the film 552 prevents it from re-passivating. In pitting it is important to notice the transition from initiation to propagation of the pits.

110.4 Characteristics

Pit Initiation

Figure 18:
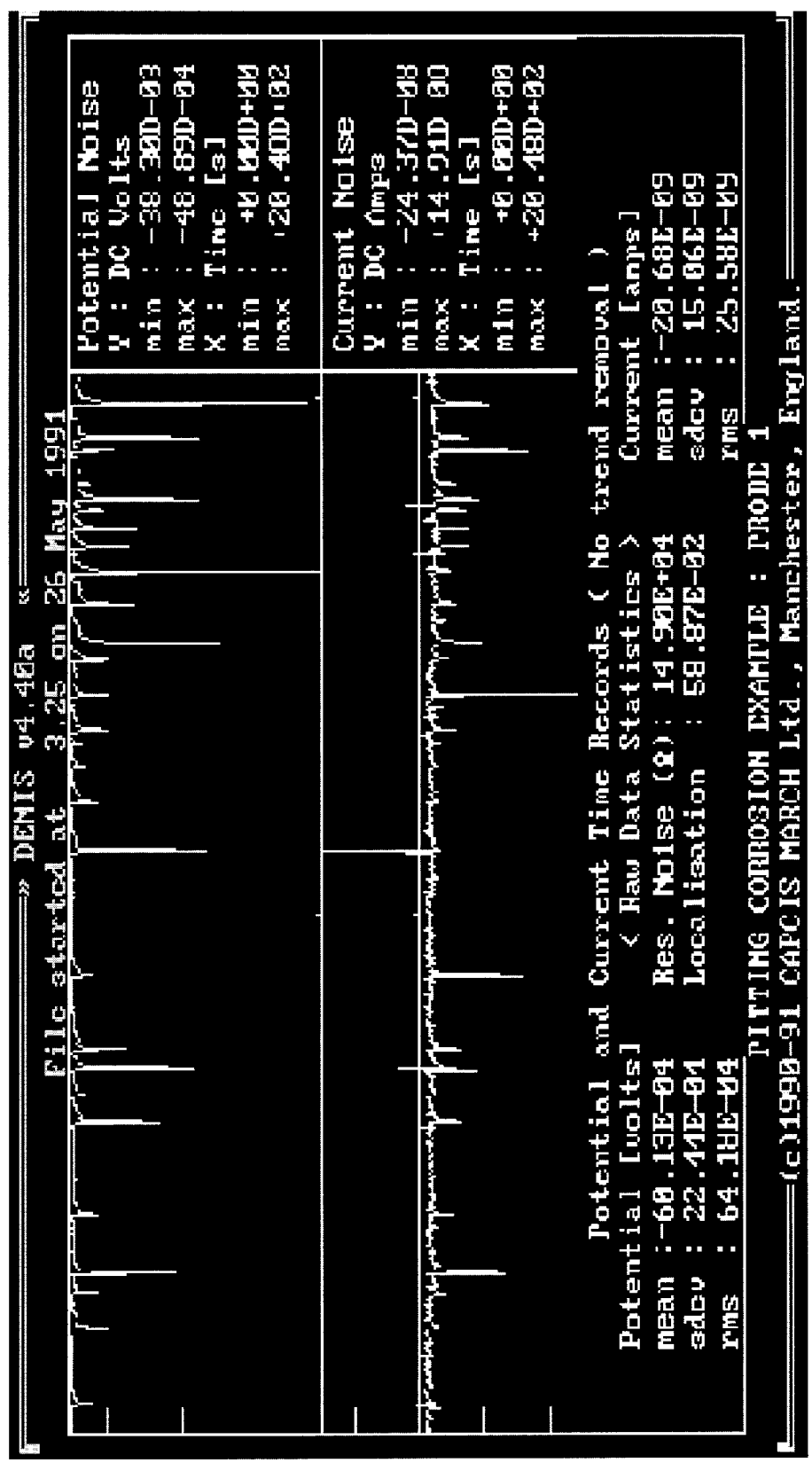
FIG. 18 is a typical electrochemical noise response for a system undergoing a pit initiation process.

FIG. 18 illustrates a typical electrochemical noise response for a system undergoing a pit initiation process. These types of process are characterized in the time domain by bi-directional current transients with corresponding negative going potential transients. Systems undergoing this type of process are usually in a passive or semi-passive state wherein the overall corrosion rate is low. Depending upon the wiring of the electrodes, the potential would be cathodic (downward) if pitting occurs on the working electrode, and anodic (upward) if pitting occurs on the reference electrode. Localized breakdown in the passive film results in a spontaneous anodic oxidation process which is referred to as Pit Initiation. This process is normally only very short lived, with spontaneous re-passivation occurring within seconds of the event, i.e. the current returns spontaneously to a lower baseline level. The potential transient which occurs associated with the current pulse has a fast negative going pulse, usually followed by a slower exponential recovery.

The intensity of the pit initiation process may be derived from the frequency and amplitude of the current signals.

Pit Propagation

Figure 19:
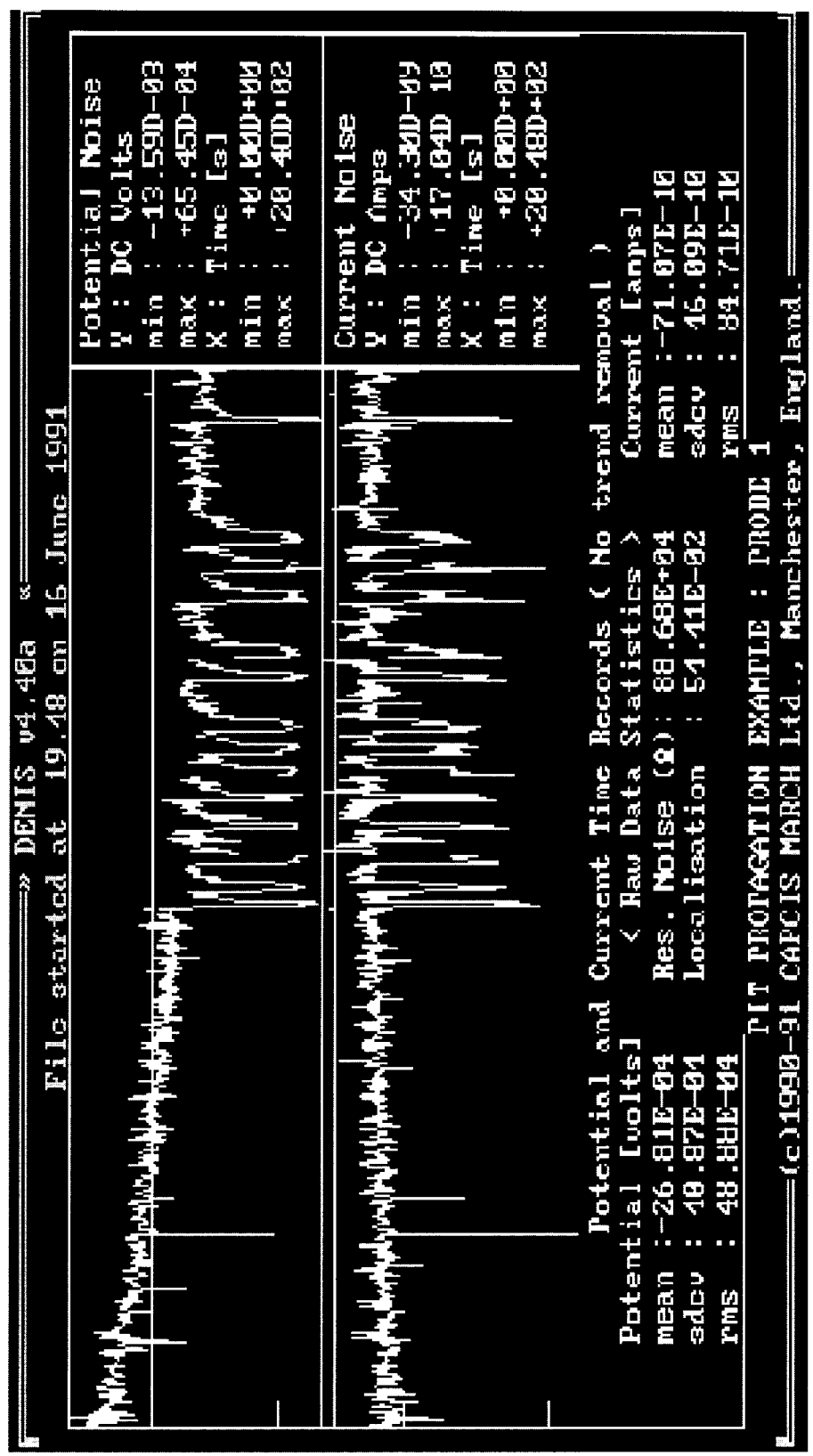
FIG. 19 is a typical electrochemical noise response for a system undergoing a pit propagation process.

Pit Propagation is similar to pit initiation but the current transients are sustained for prolonged periods, resulting in more material being lost. Low level pit propagation processes are illustrated in FIG. 19. The pit propagation process is associated with a widening of the current and potential transients, consistent with sustained depassivation (attack of the passive film). The low levels of current in this example indicate a low propagation rate.

Very low levels of current associated with passive systems may exhibit a white noise spectrum, with a large number of small transients being observed. This is considered to be associated with maintenance of the passive film rather than due to pitting phenomena.

110.5 Stress Corrosion Cracking (SCC)

Figure 20:
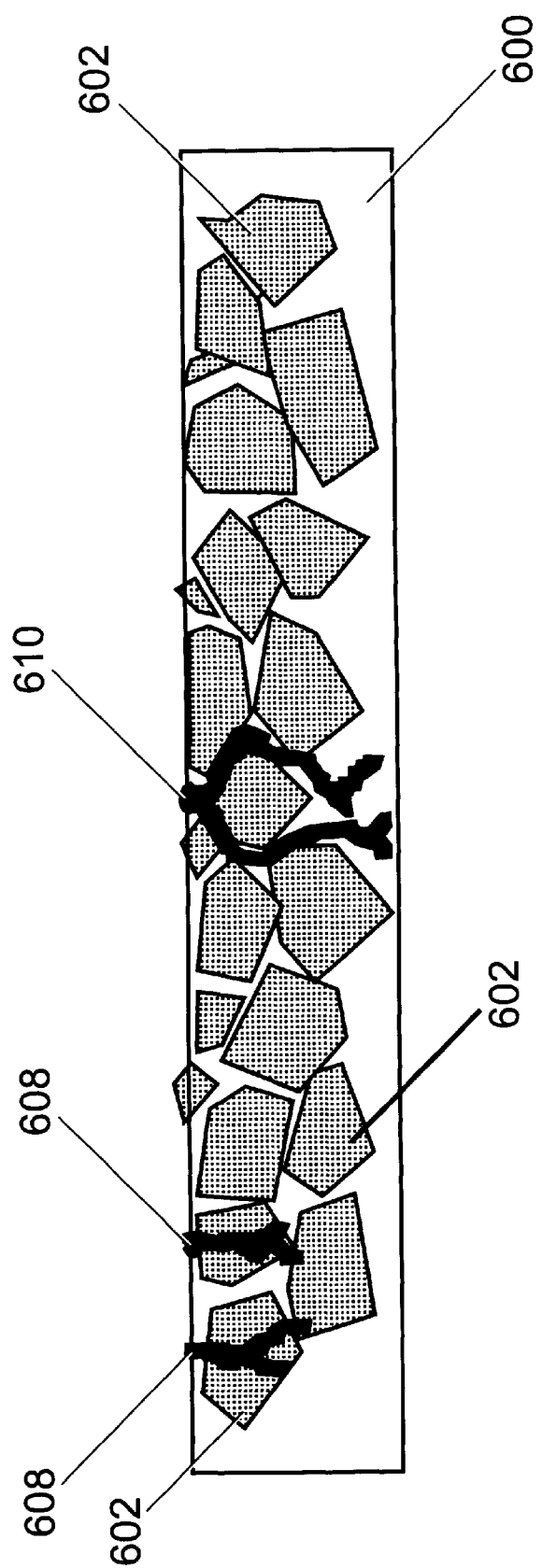
FIG. 20 is a microscopic view of a metal sample illustrating both modes of stress corrosion cracking (SCC)

There are basically two types of SCC; Transgranular and Intergranular. FIG. 20 shows a microscopic view of a metal sample 600 which illustrates both SCC modes. A plurality of grains 602 are contained within the metal sample 600. The basic concept is that the material 600 under stress is forced to crack. The difference between the mechanisms is in the microscopic structure of the material 600. The Intergranular cracking 610 will crack the material between the grains 602, whereas Transgranular cracking 608 will actually crack through grains 602 in the material.

110.6 Characteristics 110.7 Trans Granular Stress Corrosion Cracking (TGSCC)

Figure 21:
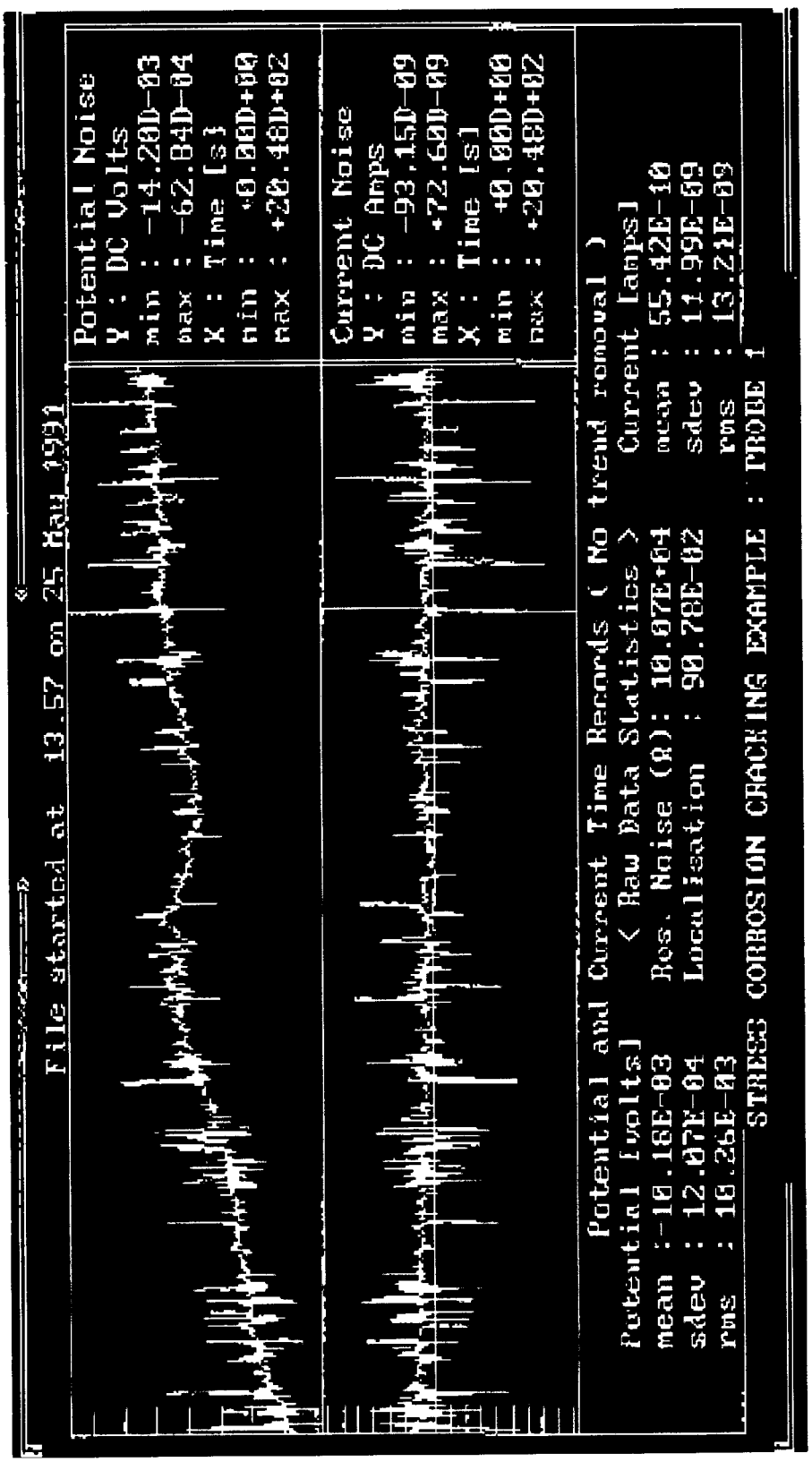
FIG. 21 is a typical electrochemical noise response for a system undergoing a transgranular stress corrosion cracking process.

Distinct differences in the time record are apparent in FIG. 21 compared to the previous general corrosion example in FIG. 18. The time record data traces show evidence of a large number of short sharp events. The current transients are characterized by negative and positive going transients. The negative going transients are highly correlated with positive potential excursions, and the positive going transients are correlated with negative potential excursions. The negative-current/positive-potential transients are typical of Trans Granular SCC, where the process occurring as the crack propagates is associated with some cathodic process. The cathodic process is probably the reduction of water along the propagation crack, producing hydrogen atoms within the crack. The anodic process that is seen to immediately follow this step is associated with an oxidation process. The generation of hydrogen atoms within the crack may lead to a localized high concentration of hydrogen atoms within the steel, promoting further embrittlement and crack extension. There would appear to be at least two processes present in this sample. Low level general corrosion and cathodic/anodic processes associated with TGSCC.

110.8 Inter Granular Stress Corrosion Cracking (IGSCC)

Figure 22:
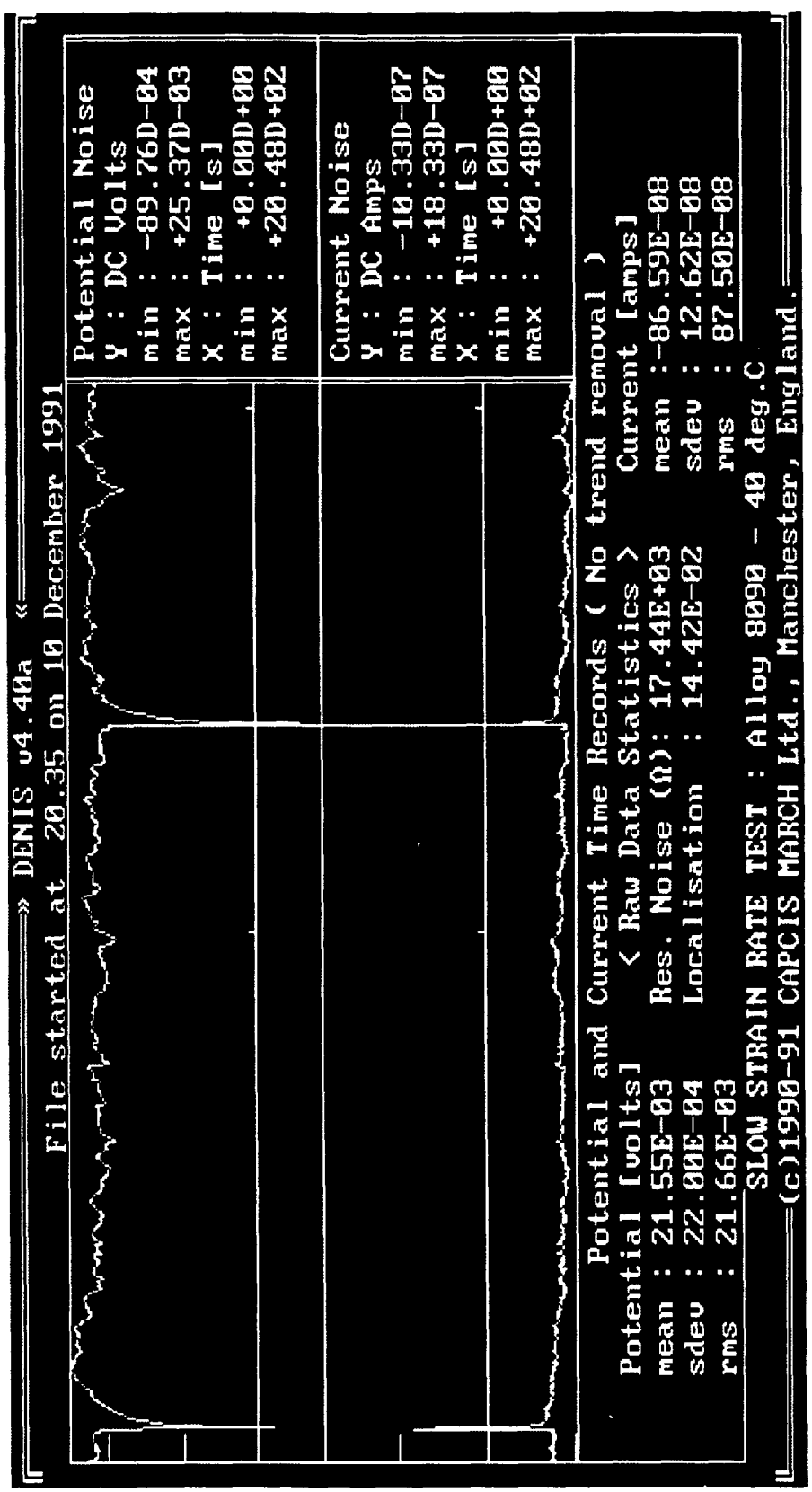
FIG. 22 is a typical electrochemical noise response for a system undergoing an intergranular stress corrosion cracking process.

The data shown in FIG. 22 indicates that the transients in the current and potential traces are typical of Inter Granular SCC. The potential transients are negative going while the current transients are positive. This implies an anodic metal oxidation process as the crack propagates.

Experimental Procedure

The software used to develop, train and test the networks in this description was Neural Works Professional II Plus™ by Neuralware Inc. This software is a neural network development tool containing all of the network architectures and training rules described earlier. The method used to display the classifications of the output layer in real time whilst learning was a classification rate. This classification rate will be referenced later and an example is shown in FIG. 23.

Figures 23, 24:
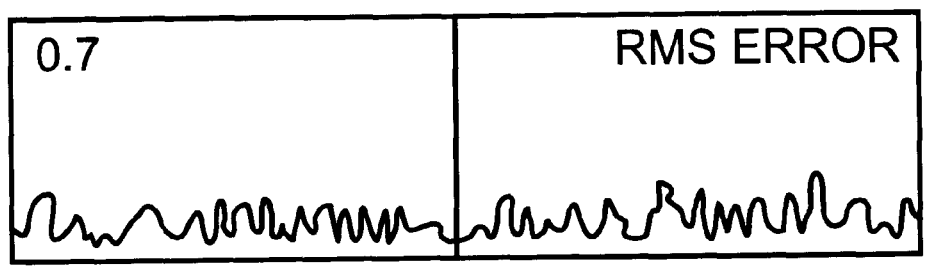
FIG. 23 is an example of a classification rate.
FIG. 24 is an example of an RMS error.

The object of the classification rate in FIG. 23 is to match the actual and desired values as displayed in this diagram. Along with the classification, the RMS error of the overall network may be displayed and can be seen to settle down to a lower value toward zero as the network becomes more competent in its training (see FIG. 24).

Network Architecture

The method of learning which was used to train the neural nets was Supervised Learning. With this method of learning the results for a particular input are known by the net at the time of training. The net is a classification network as required to determine the corrosion mechanism from a yet to be determined input made from a series of both potential and current datafiles. After analyzing all of the possible Neural Network architectures that have been studied, it was decided that most appropriate network architecture would be an Error Back Propagation network. The main reason for this choice is that all of the outputs are known for all input pattern combinations.

Data Generation

The main bulk of data used for training the net was created with the use of a three electrode test cell (similar to that shown in FIG. 1). The electrodes were made of various metals which had a different probability of inducing a particular mechanism in conjunction with specific corrosion activators.

Plots of the raw data used throughout the experimental procedure can be seen in appendix A.

Pre-Processing

Raw Data Method

The first step in the design of a neural network application is to formulate a method of pre-processing the data wherein the only main characteristics left in the data to be analyzed are the characteristics that determine the output categories required. With the application of Electrochemical Noise for determining corrosion mechanism the characteristics that are presently known to be of importance are:

The transients within the data, both potential and current.

Transient Amplitude.

Repassivation Period

Frequency.

Transient Direction (Anodic/Cathodic)

Transient Correlation (Potential to Current)

These are the only known characteristics, although there are probably a series of discreet characteristics that have not been discovered that also contribute to the mechanism determination. This is something that may be found by the network during training. The first method of pre-processing that may be used on the raw data signals removes the effects of the varying amplitude of the signals by normalizing the data. The data would then be comparable. This may be done as the amplitude relates to the severity of attack as opposed to the mechanism, thus having little effect on the mechanistic prediciton. The normalization method for this data is given by:

$$i_n = (i_t - \bar{i}) \times \left(\frac{1}{\sigma_{i(ri-im)}}\right) \quad \text{equation 5.1}$$

where:

$i_n$ is the normalized value of the current/potential signal $i_t$ is the input value at time t $\bar{i}$ is the mean value of the data set σ is the standard deviation of the data set The above treatment will result in modified data sets of zero mean, and scaled to the standard deviation values. This should then result in directly comparable modified time records which can then be examined for generic differences arising from the operative corrosion mechanism(s), irrespective of the data source or other scaling differences such as area, material constants, amplitude etc. There may be occasions when the signal is dominated by drift, and the possibility of drift (first order trend) removal will be considered later.

Figure 25:
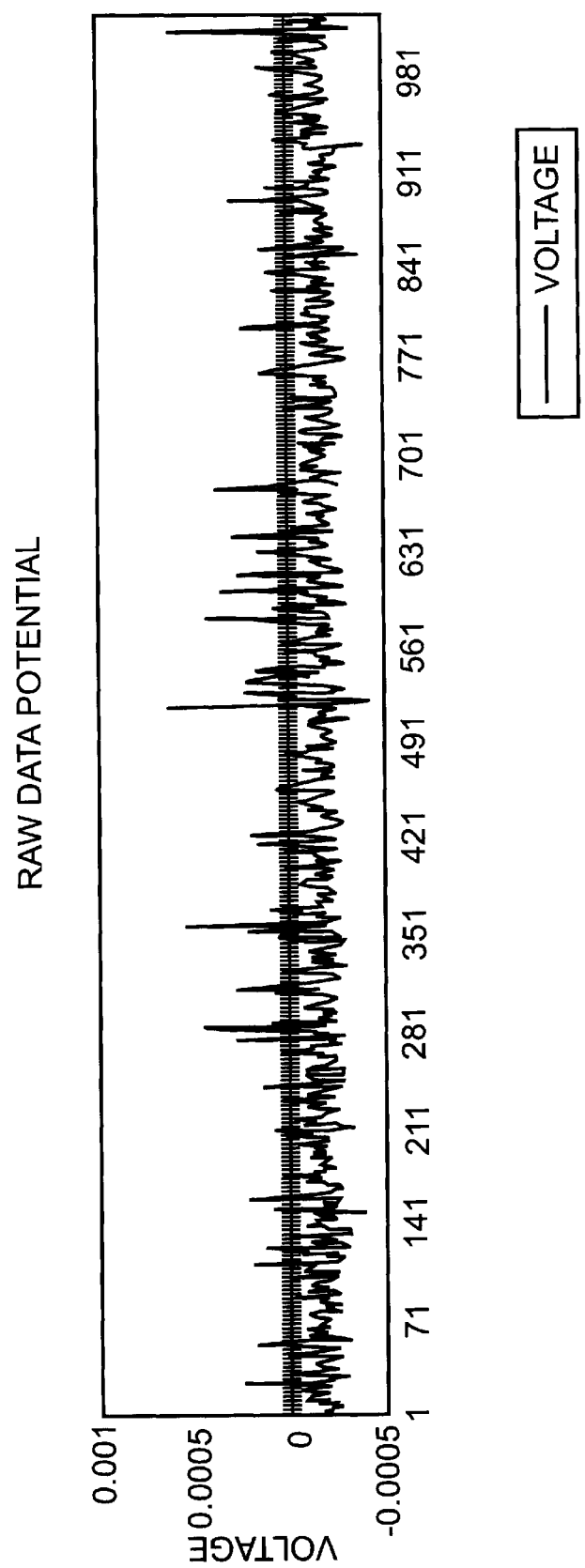
FIG. 25 is a plot of raw potential data against time used in the training of a neural net.
Figure 26:
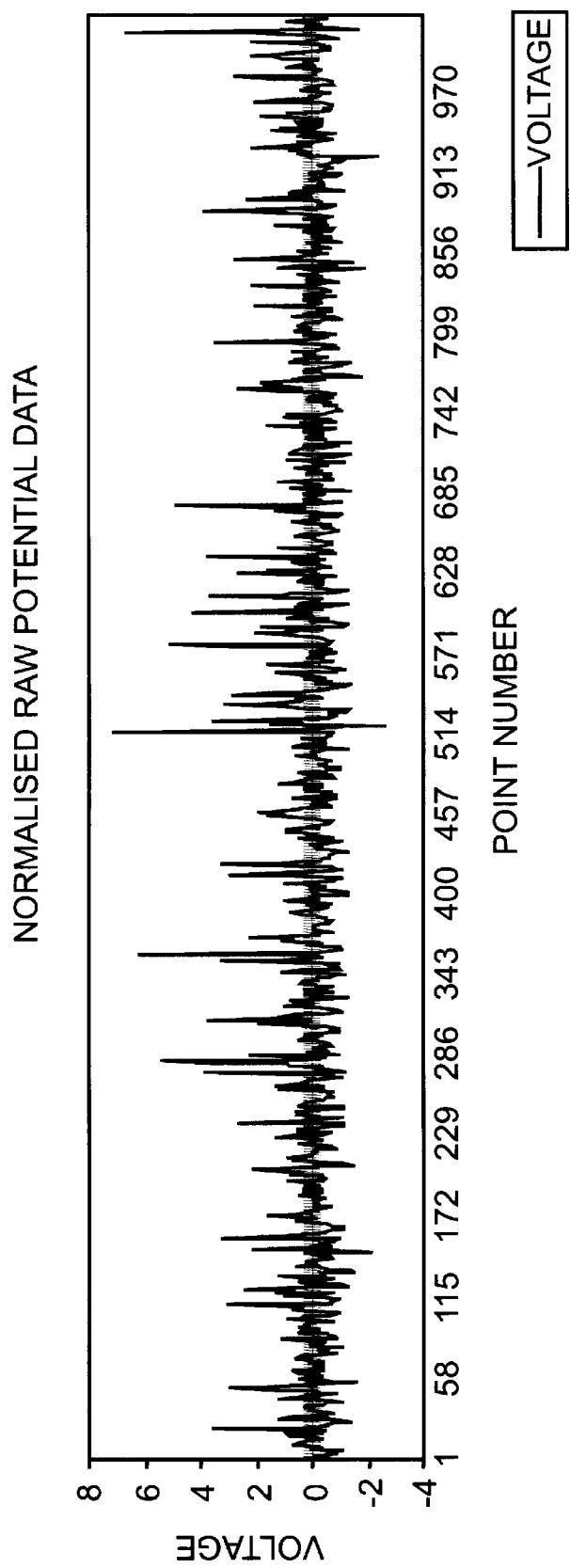
FIG. 26 is a plot of the data of FIG. 25 which has been normalized.

FIG. 25 is a plot of the raw potential data against the point number (that is the number of the sample taken), and FIG. 26 is a plot of the normalized data derived from the data in FIG. 25, the data being normalized using equation 5.1 above.

If the constants and amplitude were not taken out of the signal, the net would take this into consideration and the training data would have to cover every possible amplitude for it to be effective. This is not practical.

The network that was initially attempted will not use the full dataset as a whole input. The dataset will be divided into sections by using a scrolling window method (described previously), moving along the dataset one point at a time. The reason for the window moving one point at a time is to reduce the amount of data required for training. If the net establishes that a particular peak/transient in the data is determinant of one of the mechanisms, then this peak will be scrolled along the input layer one node at a time covering all possible positions of the peak, thus removing the possibility that the network takes into consideration the position of the peak on the X axis as being of significance. The mean and standard deviation should therefore be relative to the number of datapoints contained within this input window. This will mean that equation 5.1 will be performed on sections of the raw data the size of the input window being considered. The window that was chosen for the first attempt contained twenty datapoints (20 second window).

Statistical Method

The second method selected for data pre-processing was Skewness and Kurtosis.

$$\text{Variance} = m_{2,n} = \frac{1}{n}\sum_{i=1}^{n}(x_1\overline{x_n})^2$$

$$\text{Third Moment} = m_{3,n} = \frac{1}{n}\sum_{i=1}^{n}(x_i - \overline{x_n})^3$$

$$\text{Skewness} = g_1 = \frac{m_{3,n}}{(m_{2,n})^{\frac{3}{2}}}$$

$$\text{Fourth Moment} = m_{4,n} = \frac{1}{n}\sum_{i=1}^{n}(x_1 - \overline{x_n})^4$$

$$\text{Kurtosis} = g_2 = \frac{m_{4,n}}{(m_{2,n})^2}$$

The Kurtosis categorizes the relative peakedness or flatness of the distribution of the dataset compared to that of the normal distribution. Positive Kurtosis is indicative of a relatively peaked distribution while a zero or negative Kurtosis indicates a relatively flat distribution. This will indicate the number and frequency of transients contained within the dataset.

Figure 27:
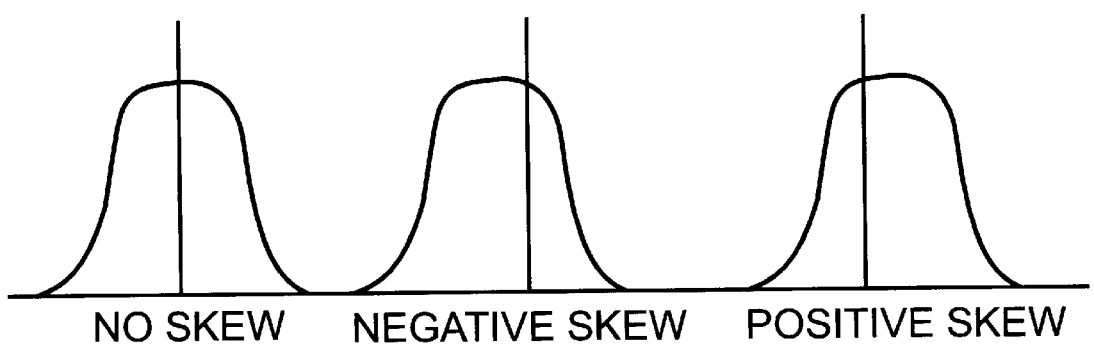
FIG. 27 illustrates the degree of asymmetry of the Skew function.

The Skewness characterizes the degree of asymmetry of the distribution of the dataset around the mean (see FIG. 27).

No Skew (FIG. 27a) equates to an even distribution of the dataset around the mean. Negative skew (FIG. 27b) indicates that the data is more negative in relation to the mean (more of the data is below zero in the normalized form). Positive skew (FIG. 27c) indicates that the data has a sore positive distribution around the mean. This function will give an indication as to the direction and width of the transients in the dataset. If the transients are abrupt but non frequent then the data will be skewed in the direction opposite to direction of the transients; the skew will however be relatively small because of the sharpness of the transients. If the transients are sharp but longer lived, the skew will give a higher value in the opposite direction of the transients. This is because the broader transients force the mean to go higher, resulting in the baseline data being more negative in relation to the mean.

Figure 28:
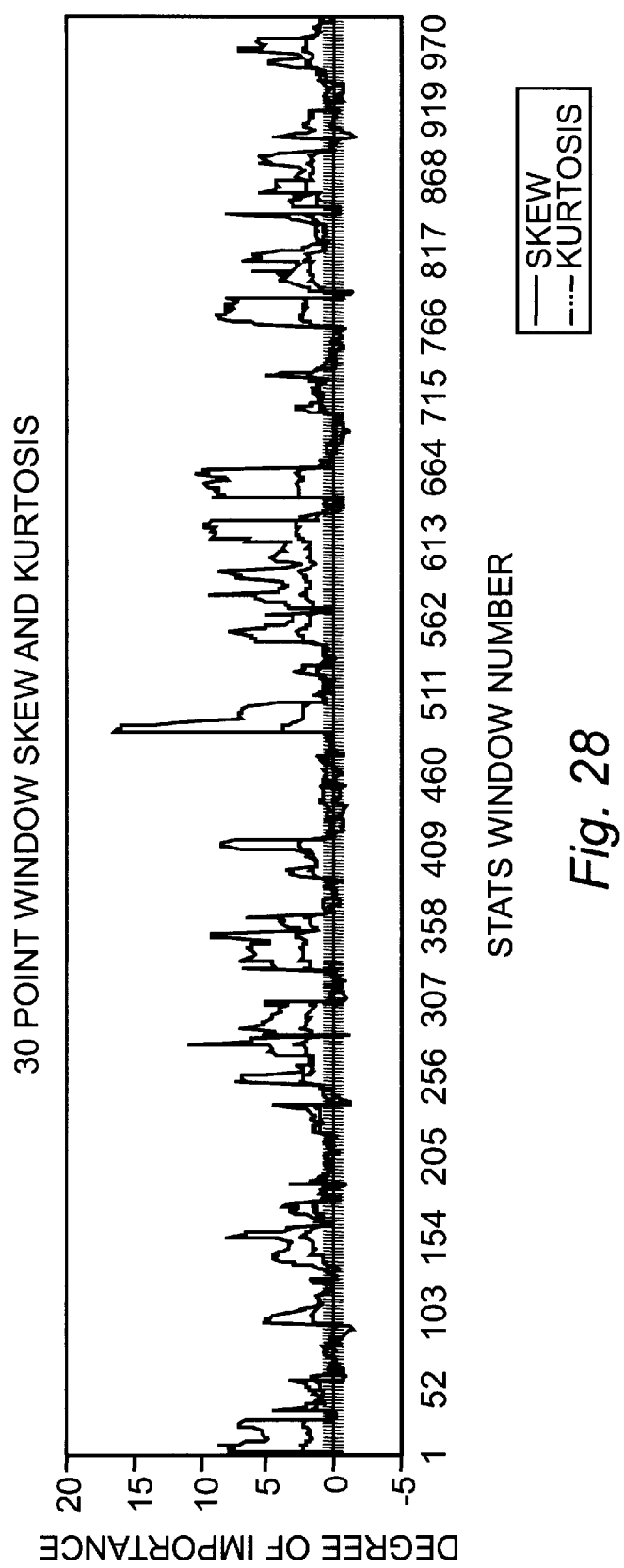
FIG. 28 is a plot of the skew and kurtosis analysis of the raw data contained in FIG. 25.

These statistics in conjunction with each other should give a good indication of the mechanism present in the dataset. The statistics will have to be performed on relatively small sections of the raw data file to ensure that all mechanisms within the file are accounted for, possibly with a moving window mechanism so that less peaked areas of the file are not swamped out by the more active areas. FIG. 28 is a sample of the statistical output when this method was performed on the raw data displayed in FIG. 25.

The plot in FIG. 28 clearly shows that the statistical analysis of the raw data values does not lose any resolution of the raw data. This gives a way of putting a lot of raw data values into the neural net with significantly fewer actual inputs, thus reducing the number of inputs required to give the network a wider picture of what is going on with the potential and current data.

As can be seen in appendix B, there are distinct differences in the scatter of the data in a skew vs. kurtosis relationship, depending upon the type of corrosion mechanism.

Two Output Network Using Raw Data Inputs

Figure 29:
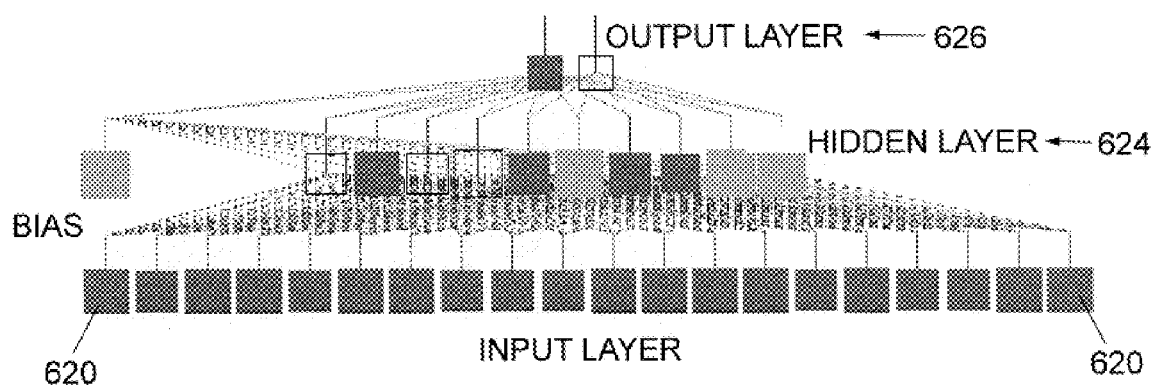
FIG. 29 is an example of a two output network configuration.

Having decided upon a network architecture to use for the Electrochemical Noise application, the next step was to design both the net and its associated inputs. FIG. 29 shows an example of a two output network configuration. An arbitrary number of inputs in an input layer 620 were chosen (in this example twenty) with a ten node hidden layer 622 and a two node output layer 624. The number of neurons (nodes) that are used at first was chosen arbitrarily and modified depending upon the degree of success or failure. The network design is all about "tweaking" the neurons and learning schedules etc. whilst in experimental mode, depending upon results gained during testing.

For the network shown in FIG. 29, the global Learn/Recall learning schedule was left with default values of Learn count=10,000, Learn Rate=1 and Temperature=0. All of the nodes were configured with Normal Summation Sum Functions, TanH Transfer functions to give higher priorities to higher values, and Standard Error calculation using the Delta Rule.

The test data used to train the net (see appendix A,1) was normalized using equation 5.1 above.

Three Output Network Using Raw Data Inputs

After the initial success of the Error Back-Propagation network in FIG. 29 with the classification of general and localized corrosion mechanisms, the next step was to design a network architecture capable of distinguishing between the two localized events of pitting and stress corrosion cracking. Due to the early success of the architecture chosen in the previous example, a network of the same design was used (see FIG. 30), the basic modification required being to change the number of outputs from two to three. The three outputs were classified as shown in Table 5.1 below.:

TABLE 5.1

Three Neutron Output Schema

| Output | 1 | 2 | 3 |
|---|---|---|---|
| Mechanism | General | Pitting | SCC |

Table. 5.1 Three Neuron Output Schema

The network shown in FIG. 30 again has a softmax output, spreading the probability over the three outputs, the ideal scenario being a prediction of one in any one category. The net consists of a twenty node input layer 630, a ten node hidden layer 632 and a three node output layer 634. The test data used to train the net (see appendix A,2) was normalized by the same formula as the previous experiment (ie equation 5.1 above).

The training set contains five 1024 point datafiles, one file of general corrosion data, one pit initiation, one pit propagation, one SCC initiation and one SCC propagation. The network is not concerned with the sub modes of initiation or propagation; they were included in the data set because the main characteristics of transient direction are the same irrespective of initiation or propagation. The network was trained for 100,000 cycles.

Three Output Network Using Statistical Inputs

Having determined that both the Skew and Kurtosis functions on the potential and current data sets are needed, it was necessary to decide upon a sufficiently large number of datapoints with which to use the functions to give approximately 10inputs (arbitrary), for each of the data sets (both potential and current), resulting in forty inputs to the network. A moving window of approximately 20 datapoints of raw data input into the statistical functions through the whole data set plotted over time was sufficient to visually analyze the data to determine exactly which corrosion mechanisms (if any) were attacking the sample. The short length of the input window ensures that pitting data characteristics would be detected, along with SCC data characteristics.

The size of the input window (approximately 20 points) is a first estimation of the appropriate value. It was discovered that this technique recognized discrete yet mechanistically important transients that a plot of 1024 raw datapoints could hide due to the amplitude scale of the data over such a large number of points. With this information taken into consideration it was decided that calculating the Skew and Kurtosis values for a twenty point window did not lose any of the characteristics of the data. Therefore, pre-processing with a twenty point moving window through the raw data for ten iterations (in effect widening the raw datapoint window coverage to thirty points), points 1–20, 2–21 . . . 11–30, should suffice.

Figure 30:
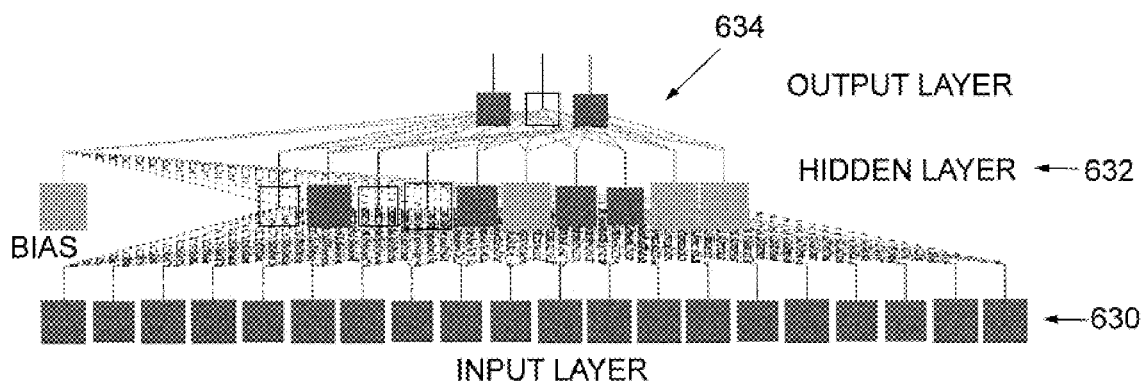
FIG. 30 is an example of a three output network configuration.
Figure 31:
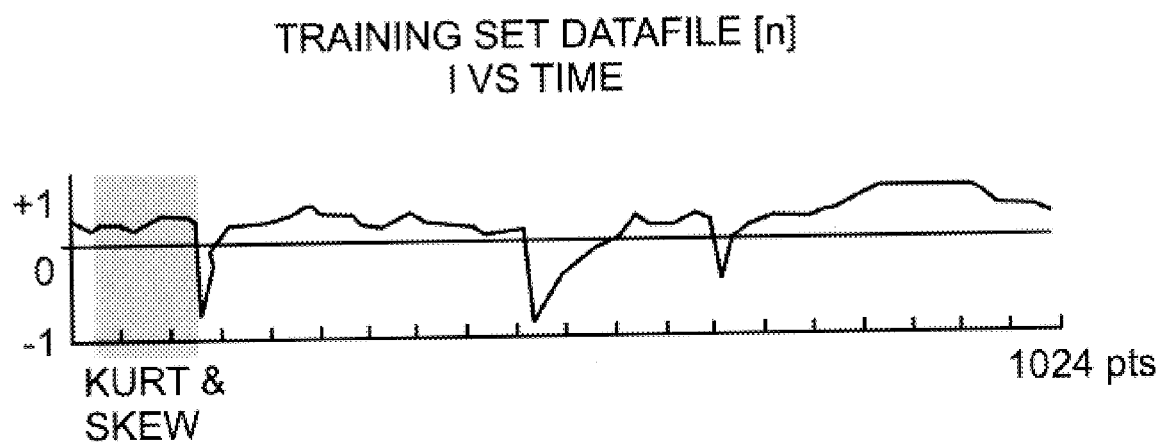
FIG. 31 is a plot of current against time for the training set datafiles in appendices A,1 and A,2.

FIG. 31 shows a plot of current against time for the training set in Appendices A,1 and A,2 (normalized) using the net shown in FIG. 30.

The result of this was to widen the raw data input window whilst keeping the number of inputs to the network down and not losing any resolution or characteristics in the resulting data.

Figure 32:
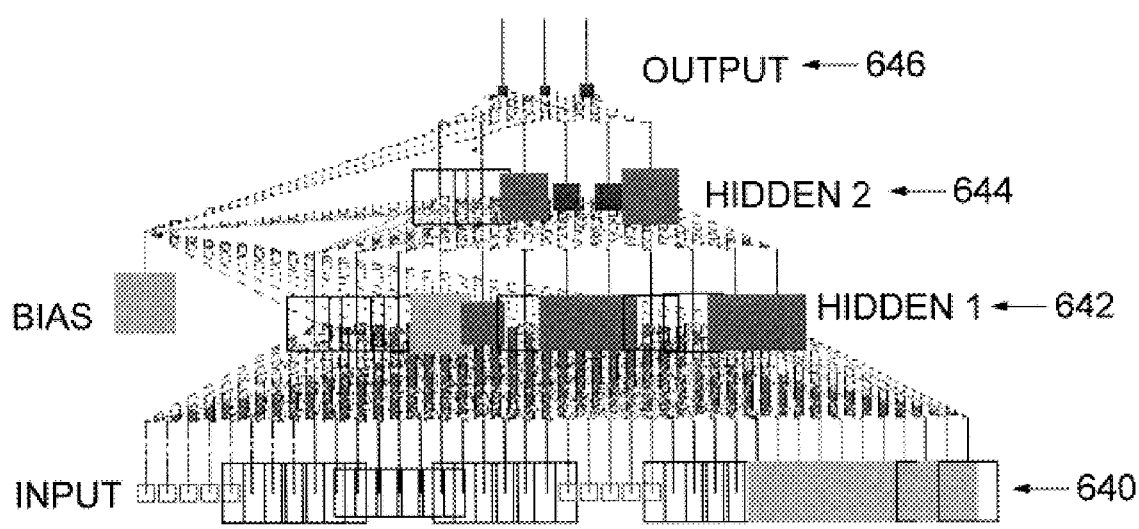
FIG. 32 is an example of a three output network configuration with a second hidden layer.

The introduction of potential however did result in a restructuring of both the hidden and input layers within the network infrastructure. It was discovered that the net would have difficulty trying to resolve the input output combinations with just one hidden layer. The introduction of a second hidden layer gives the net more of a chance to learn and less to do with one batch of weight-threshold combinations. FIG. 32 shows an example of a three output network configuration with a second hidden layer added.

The network in FIG. 32 again has a softmax output, spreading the probability over the three outputs, the ideal scenario being a prediction of one in any category. The net consists of a forty node input layer 640 (10 Potential Kurtosis, 10 Potential Skew, 10 Current Kurtosis, 10 Current Skew); a twenty node hidden layer 642; a ten node hidden layer 644; and a three node output layer 646. The test data used to train the net was exactly the same as that used in the previous experiment (see appendices A,1 and A,2)

Table 5.2 below shows the relationship between the outputs and the corrosion mechanism which they indicate for the three neuron output schema of FIG. 32.

TABLE 5.2

| | Three neutron output schema | | |
|---|---|---|---|
| Output | 1 | 2 | 3 |
| Mechanism | General | Pitting | SCC |

Table 5.2 Three Neuron Output Schema

Five Output Network Using Statistical Inputs

Figure 33:
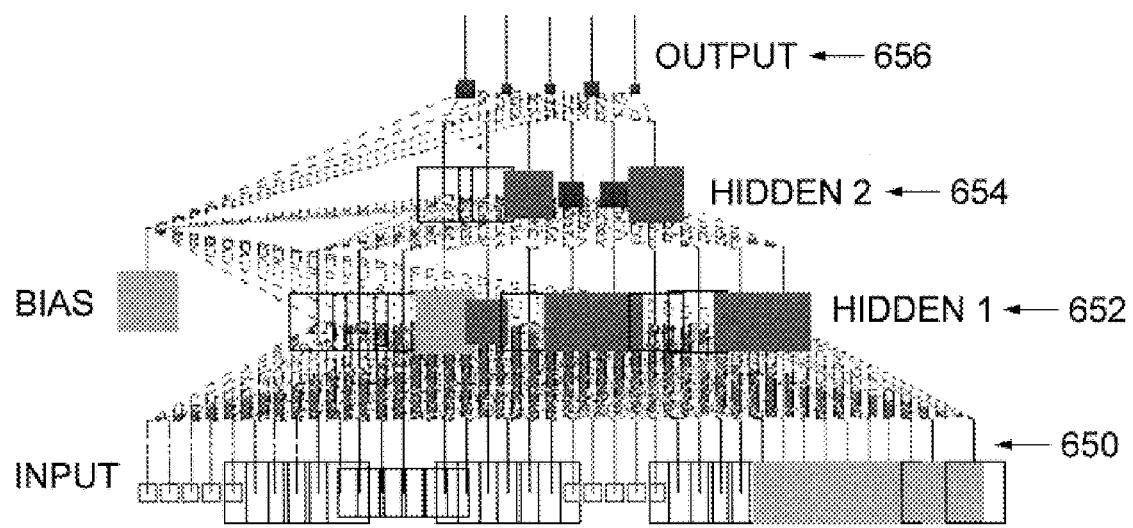
FIG. 33 is an example of a five output network configuration.

FIG. 33 shows an example of a five output network configuration. As in the previous examples the network output is a softmax distribution, spreading the probability over the five outputs. The net consists of a forty node input layer 650 (10 Potential Kurtosis, 10 Potential Skew, 10 Current Kurtosis, 10 Current Skew); a twenty node hidden layer 652; a ten node hidden layer 654; and a five node output layer 656. The test data used to train the net was exactly the same as that used in the previous experiment (see appendices A,1 and A,2).

Table 5.3 below shows the relationship between the outputs of the network in FIG. 33 and the particular corrosion mechanism which they indicate.

TABLE 5.3

| | Five neuron output shema | | | | |
|---|---|---|---|---|---|
| Output | 1 | 2 | 3 | 4 | 5 |
| Mechanism | General | Pit Initiation | Pit Propagation | SCC Initiation | SCC Propagation |

Table 5.3 Five Neuron Output Schema

Due to the introduction of temperature and the relatively poor performance of the settling of the RMS Error along with the introduction of two new outputs, it was evident that the Learning Rate and Momentum of the training should be reduced. The reduction in the learn rate and momentum would give the net more time to settle in an optimum position with a higher momentum before gradually bringing the learning momentum down to 0.001, rather than rapidly reducing the momentum of the net and not allowing it to settle. This is because as low an RMS Error value as possible is required if the output distribution is to be softmax and one technique is to have a significantly higher output than the rest. The training regime was lengthened from 100,000 cycles to 310,000 cycles and the momentum and learning rate reduced accordingly. These values were adjusted according to the settling rate of the RMS error in conjunction with the performance of the classification rate.

The Network learning schedule was altered to reflect the settings shown in Table 5.4 below.

TABLE 5.4

| | Network configuration | | | | |
|---|---|---|---|---|---|
| Learn Count | 500 | 1,000 | 70,000 | 150,000 | 310,000 |
| Temperature | 0.80 | 0.60 | 0.45 | 0.30 | 0.20 |
| Learning Rate | 0.20000 | 0.10000 | 0.018750 | 0.00117 | 0.00000 |
| Momentum | 0.20000 | 0.1000 | 0.05000 | 0.00312 | 0.00001 |
| Error Tolerance | 0.1000 | 0.1000 | 0.1000 | 0.1000 | 0.1000 |

Table 5.4 Network Configuration

The same training data as previously used was selected to give an indication of the differences in classification compared to the nets shown in FIGS. 29, 30 and 32 (see appendices A,1 and A,2). The network was configured and left to train for approximately 2.00 hours before the training schedule had been completed.

Five Output Network Using Statistical Inputs

Figure 34:
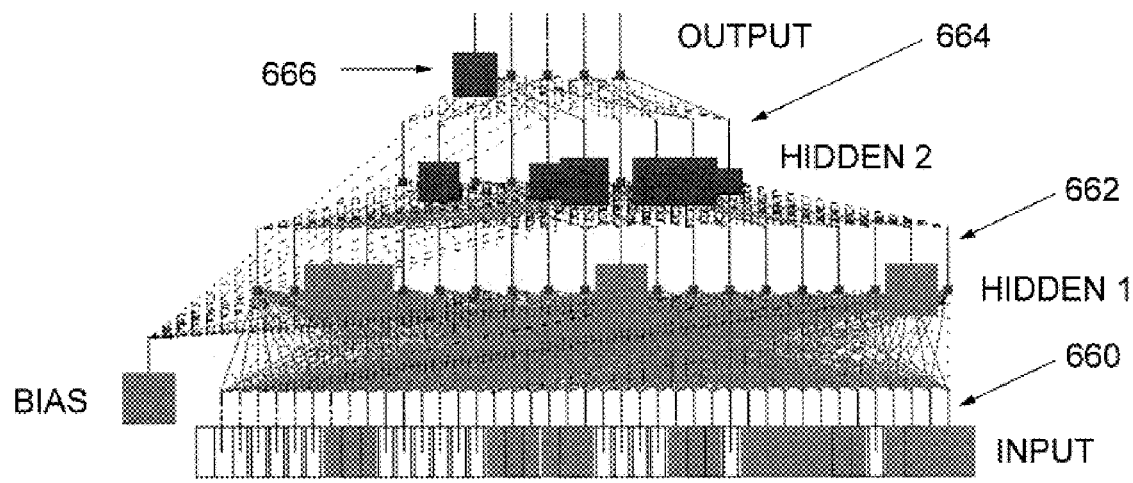
FIG. 34 shows the network of FIG. 33 with an additional input in the input layer.

FIG. 34 shows an example of a five output network configuration which is similar to that shown in FIG. 33 but with the addition of an "environmental input". The network of FIG. 33 consists of a forty-one node input layer 660 (10 Potential Kurtosis, 10 Potential Skew, 10 Current Kurtosis, 10 Current Skew, 1 environment); a twenty node hidden layer 662; a ten node hidden layer 664; and a five node output layer 666. The test data used to train the net was the same data used in the previous experiment (see appendices A,1 and A,2), with the addition of Inter Granular samples of Initiation and Propagation (appendix A,3) and a noisy general corrosion datafile (appendix A,4). The sub mechanisms of initiation and propagation of IGSCC and TGSCC were grouped together in the global classes of IGSCC and TGSCC.

The highlighted nodes (ie the larger squares in FIG. 34) show the path of firing neurons to obtain a certain output; in this case node 1 in the output layer (general corrosion), as indicated by table 5.5 below.

TABLE 5.5

| | Five neuron output schema | | | | |
|---|---|---|---|---|---|
| Output | 1 | 2 | 3 | 4 | 5 |
| Mechanism | General | Pit Initiation | Pit Propagation | TGSCC | IGSCC |

Table 5.5 Five Neuron Output Schema

The output categories shown in table 5.5 may be expanded to incorporate SCC initiation and propagation.

With the error in distinguishing between pit and SCC propagation in the previous example the environment variable was introduced as an additional input. This variable will be set to 1 if the sample is stressed or 0 if the sample is free from stress. The introduction of this variable will enable the net to clearly distinguish between the pitting and stress corrosion cracking mechanisms.

The theorized problem to be overcome with this environment variable in that it is possible that the net will not be able to identify a pitting mechanism with a stressed sample. It is also possible that the network may not know how to determine general corrosion that may occur in both stressed and un-stressed samples.

To overcome these possible problems the general corrosion sample datafiles were introduced and duplicated wherein the exact same data was used as two training datafiles. The general corrosion files were used both with the environment variable set as 1 and he environment variable set as 0. This attempted to overcome the problems that the network may encounter in attempting to distinguish general corrosion depending upon the setting of the environment variable (ie a 0 or 1). To overcome the problem that the network may have in classifying the possibility that the sample may contain a pitting mechanism whilst under stress, a small example of a pitting corrosion file was introduced with the environment variable set as stressed (ie 1). This was done to ensure that the environment variable is not the single constant that would distinguish between the pitting and stress corrosion cracking mechanisms, as if this were not introduced, the net may take this variable as a de-facto determinant factor.

The pit propagation datafile was changed to remove the dual mode mechanisms during training.

Five Output Network Using Statistical Inputs

Figure 35:
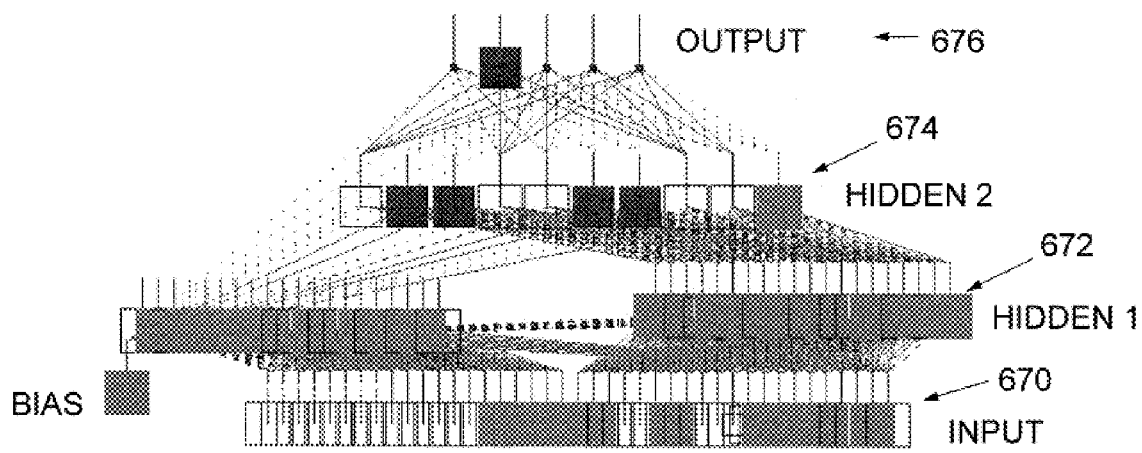
FIG. 35 is a five output network configuration, similar to that of FIG. 34 with additional nodes in the hidden layers.

FIG. 35 shows a five output neural network similar to that shown in FIG. 33. The net of FIG. 35 consists of a forty-one node input Layer 670 (10 Potential Kurtosis, 10 Potential Skew, 10 Current Kurtosis, 10 Current Skew, 1 environment); a forty node hidden layer 672 (twenty connected to the potential values, twenty connected to the current values and an environment variable connected to all); a ten node hidden layer 674; and a five node output layer 676. The test data used to train the net contained the same data used in the previous example.

As can be seen from the network shown in FIG. 35, the first hidden layer 672 connections were customized to force the network to consider the correlation between skew and kurtosis for both the current and potential. This was done as a result of the examination of the results of the previous network shown in FIG. 34.

The output configuration for this network was exactly the same as the previous example (see Table 5.5 above). The network was allowed to train for its full cycle, settling down to a net-wide RMS error value approximating the previous example.

Results & Interpretation

The following is an analysis of the results observed from the procedure undertaken above. The interpretation of the results of the earlier networks lead to changes in the following networks to overcome problems and anomalies encountered.

Two Output Network Using Raw Data Inputs

Figure 36:
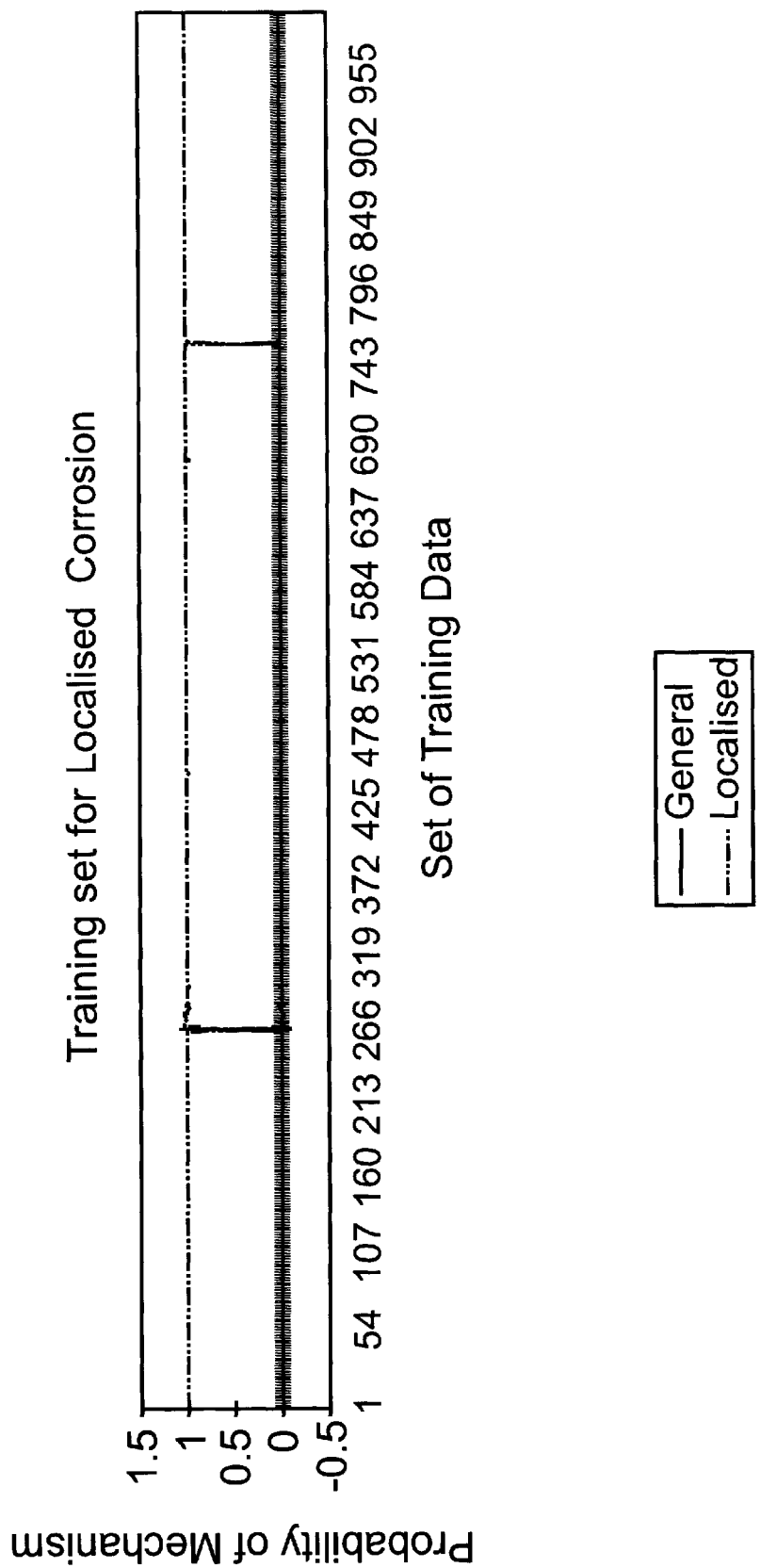
FIG. 36 is the training schedule results for the two output network of FIG. 29 predicting localized corrosion.
Figure 37:
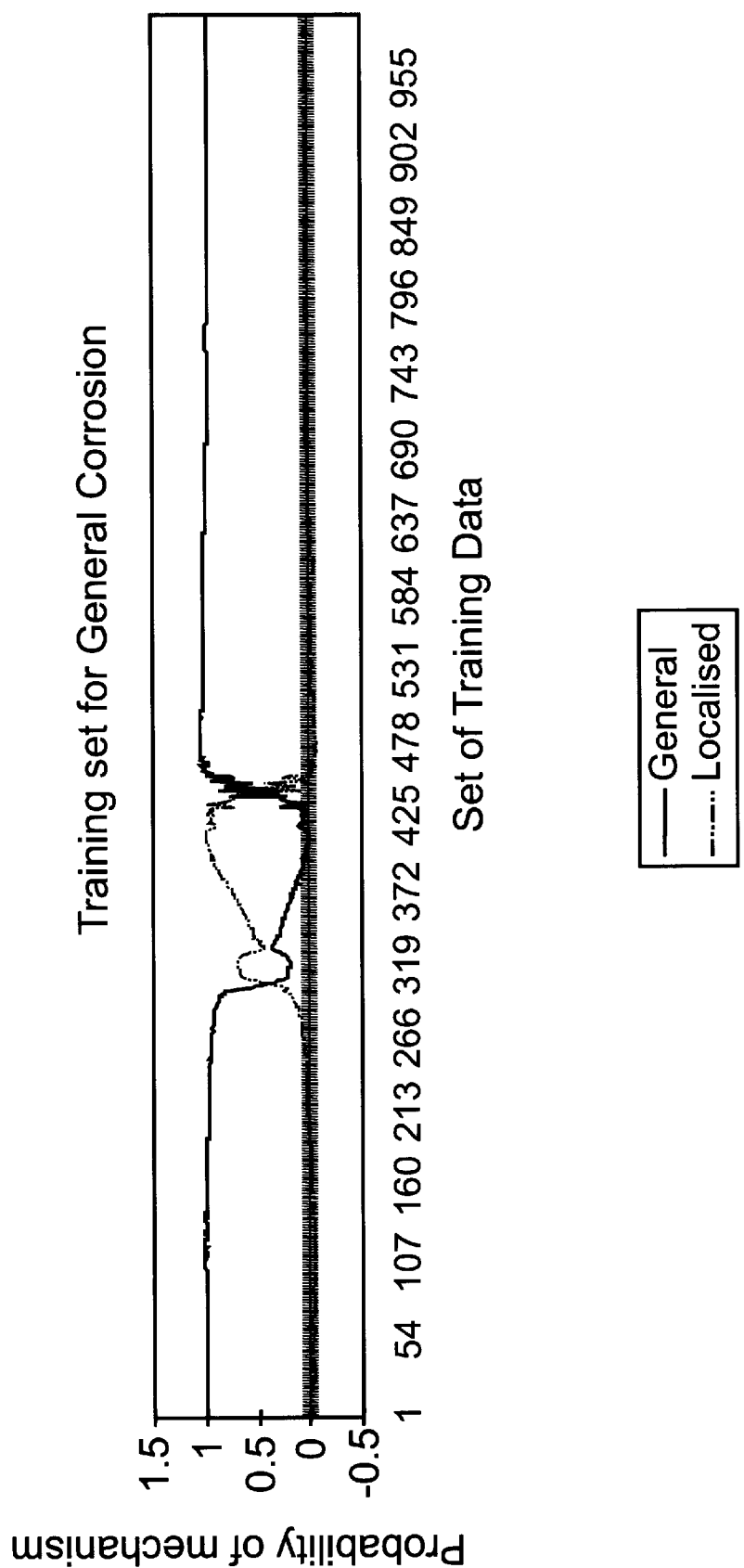
FIG. 37 is the training schedule results for the two output network of FIG. 29 predicting general corrosion.

After training the network shown in FIG. 29 for approximately 15,000 cycles, the net settled down giving a net wide RMS error of approximately 0.05 and a highly correlating Actual versus Desired classification rate (approximately 0.88 for General corrosion and 0.99 for Localized corrosion). The end result was that the net could categorize the two mechanisms with a very high degree of probability. The plots shown in FIGS. 36 and 37 are of the training data run under test after the network had completed its training. The network was trained on the Current versus time datasets. Only the current was used for this test as a localization mechanism can be detected from these values alone.

FIG. 36 shows that the network of FIG. 29 has learnt to categorize the localization mechanism with an extremely high probability.

FIG. 37 shows that the network of FIG. 29 has learnt to categorize the general corrosion mechanism with an extremely high probability, although there is the presence of localized attack. Analysis of the raw data shows that there was actually the presence of some localized activity. This can be seen by the transients near the start of the datafile.

Three Output Network Using Raw Data Inputs

The initial results of the test using the network shown in FIG. 30 gave results which were not very promising. Although the net predicted the mechanism with a reasonable probability of success, the results were in no way conclusive. Further analysis of the training data to try to determine the reasons for the lack of success using the network of FIG. 30 uncovered a fundamental flaw in the input data. The characteristics identified in determining the mechanism have shown that in order to categorise the mechanism, the Potential must be used in conjunction with the current as the transients and their respective direction (Anodic/Cathodic) must be used with a degree of correlation. These bi-directional characteristics along with peak width are fundamental in determining the mechanism.

It would seen that in the absence of the required and more obvious differences in the input data in correlation with the required output, the network isolated the more opaque features (that is the amplitude, direction and frequency of the transients in the current). The reason for this creation of false characteristics is due to insufficient feature difference in the input in relation to the required output. The results of this test have shown that there is a need to include the potential values in the input data to obtain the relationships necessary to categorize the mechanisms.

Three Output Network Using Statistical Inputs

Figure 38:
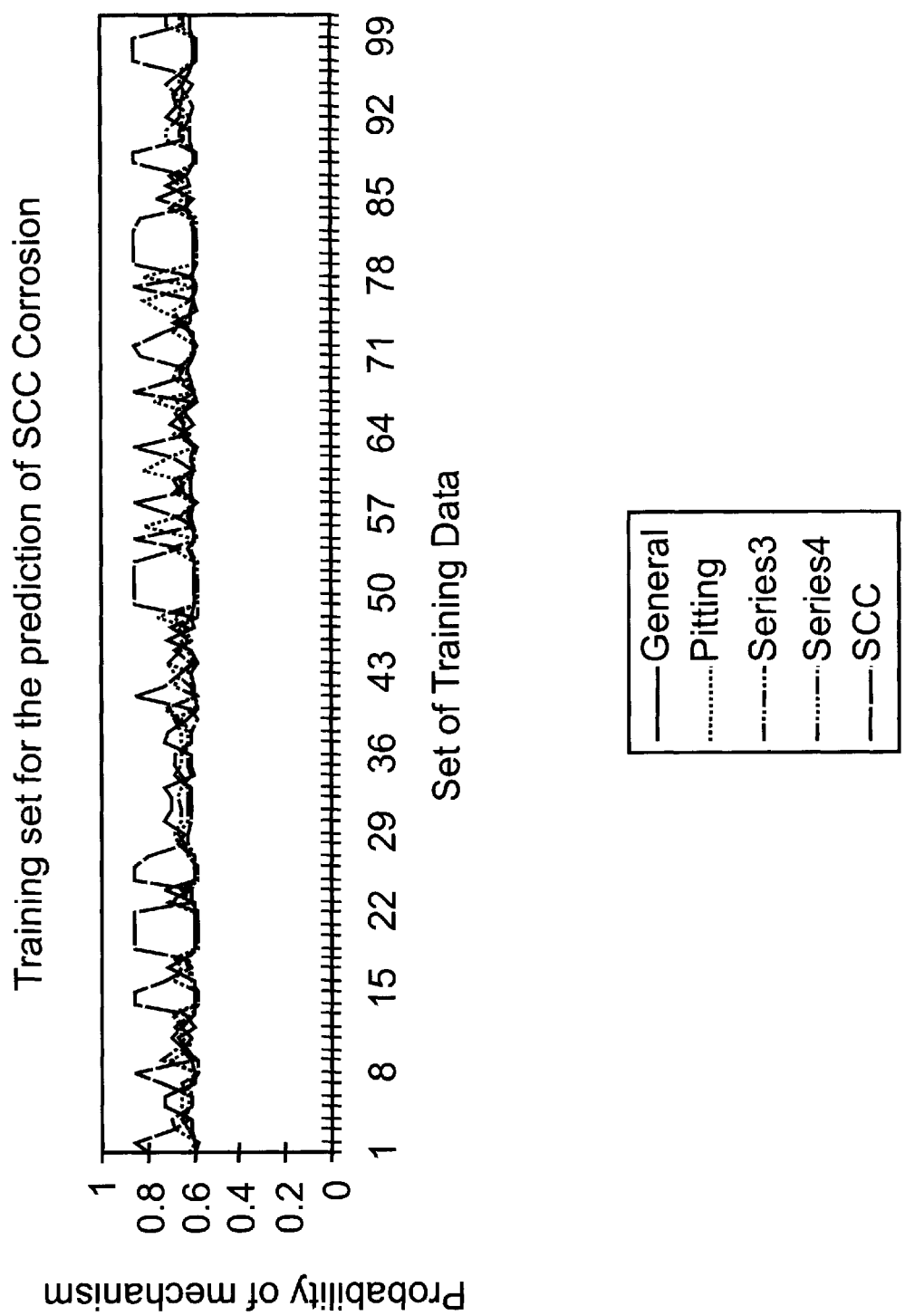
FIG. 38 is the SCC training plot results for the three output network of FIG. 30.
Figure 39:
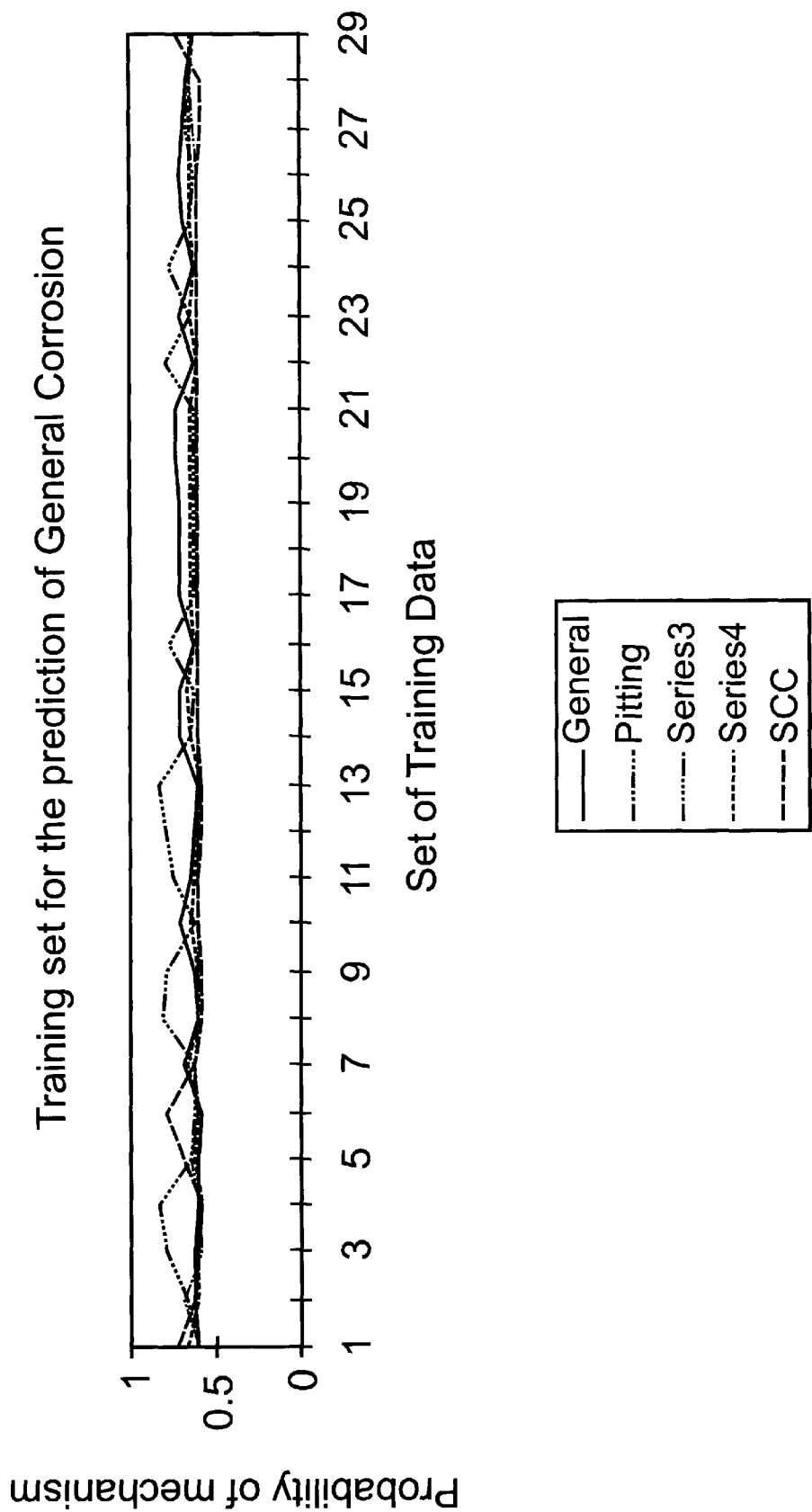
FIG. 39 is the general training results plot for the network of FIG. 30.
Figure 40:
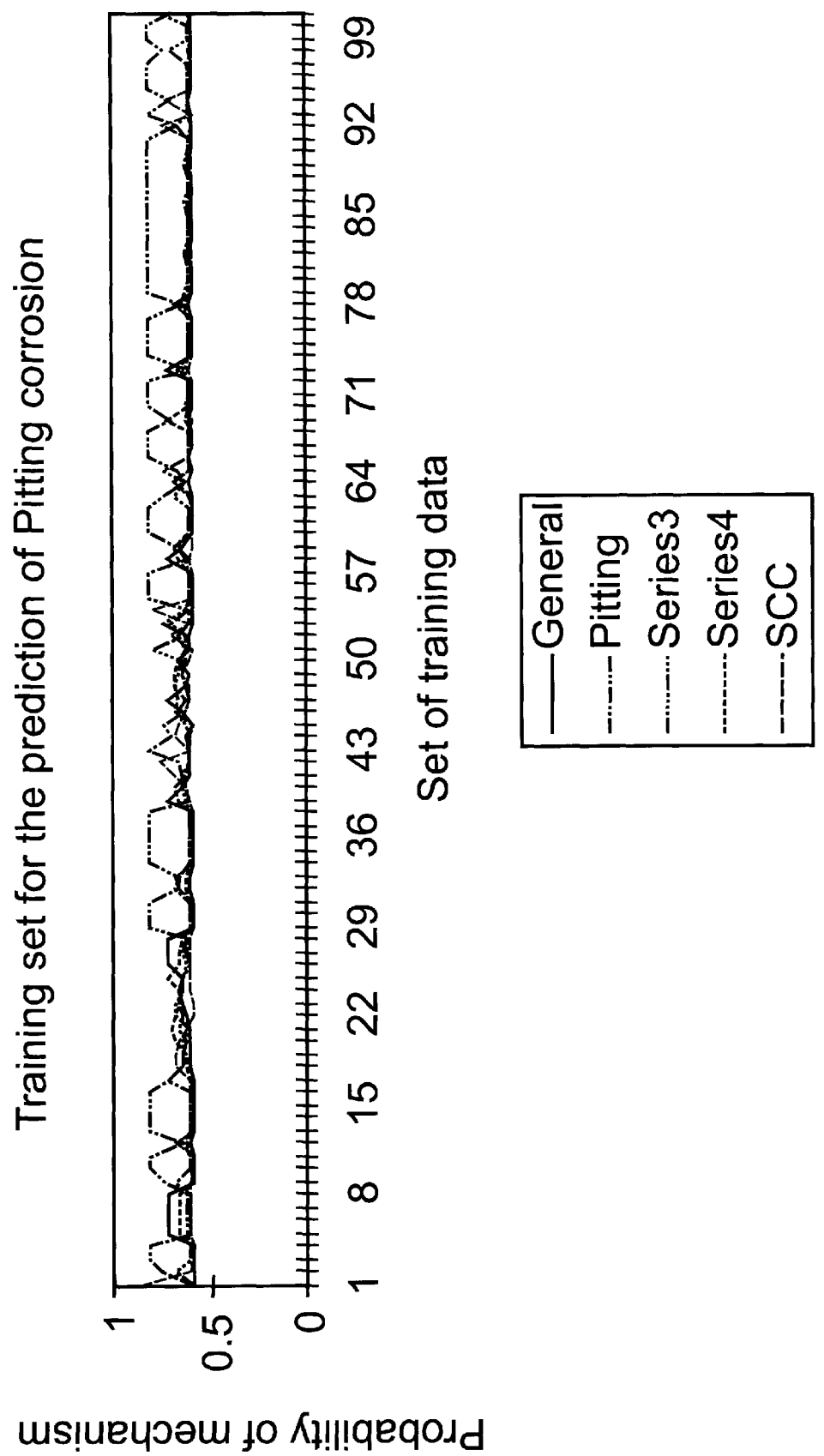
FIG. 40 is the pitting training results plot for the network of FIG. 30.

FIG. 38 is the SCC training file results plot; FIG. 39 is the pitting training file results plot; and FIG. 40 is the general training file results plot for the network shown in FIG. 30.

During initial training the RMS error of the network of FIG. 30 settled down rapidly (after approximately 20000 training cycles) to approximately 0.5, then dropped very slowly (after about 100000 training cycles) to a value between 0.12 and 0.4. It was discovered that stopping the network during training at arbitrary intervals and adjusting the hidden layer weights brought the RMS error down in a more linear fashion to a lower overall error value at the end of training. This led to the conclusion that during training the network was settling in a state of false minima. The implication of this is that the network was settling in a well state out of which the weights cannot jump with a temperature of zero. This was due to the fact that when the network was settling into a well, a change in the weights used in the network of FIG. 30 would take the network backwards in its training cycle to a worse state in relation to the required results than that in which it had settled. The introduction of a temperature value falling from 1 to approximately 0.2 during training would allow the network to reach a state false minima, but depending upon the temperature value and the stage of learning, allow the network to go back to a worse state and try to avoid the well by giving it the chance of taking another path on the next cycle. This would increase the probability that the false well be avoided in the settled state. This procedure is called "Simulated Annealing".

The network schedule was changed to reflect the incorporation of simulated annealing. The results, as expected, showed that the RMS Error graph settled down in a more linear fashion. The overall error at the end of training (approximately 100,000 cycles) showed that the RMS Error had settled down to a value of approximately 0.3.

The next step was to incorporate the initiation and propagation sub mechanisms into the output of the net whilst leaving the input and hidden layers with the same number of elements. The reason for not changing the number of hidden and input layer nodes with an increasing number of output nodes being that the current design of neural network seemed to be recognizing the bi-directional characteristics of the data set with a high degree of success. The incorporation of the extra outputs means that the net will have to isolate a further set of characteristics to categorize the extra outputs. The main characteristics that would be recognized were the changing width of the Anodic/Cathodic potential spikes with respect to their relative current spikes for propagation events. This will however be dependent upon the training data and the number of unique characteristics contained within each data set for each mechanism.

Five Output Network Using Statistical Inputs

The results of the network infrastructure change shown in FIG. 33 along with the change in the learning schedule resulted in a higher probability of determining the particular corrosion mechanism. The training set had classified the data with a high probability from a first test.

The plots displayed in FIGS. 41 to 45 are of the results of the Training set after the net shown in FIG. 33 was trained and tested on the training file. The Y axis is the probability of corrosion mechanism. There are five mechanisms in the present net, with a probability of one being distributed across the five possible outcomes. It appears from these files and others previously done that a probability of approximately 0.2 is relative to zero. This is because it is implausible to expect that a noisy file will not have at least some of the characteristics of the other four mechanisms even if one of the five is predominant. The X axis is the number of training sets provided for the file. The maximum is 101 because the data file of 1024 points is being split into 20 point batches for which a Skew and Kurtosis value is being calculated. This 20 point batch is then scrolled along the raw data file by 1 point for another statistics calculation. This is done 10 times for each training set.

The training file in the net contained 1024 point data files for each of the corrosion mechanisms.

Figure 41:
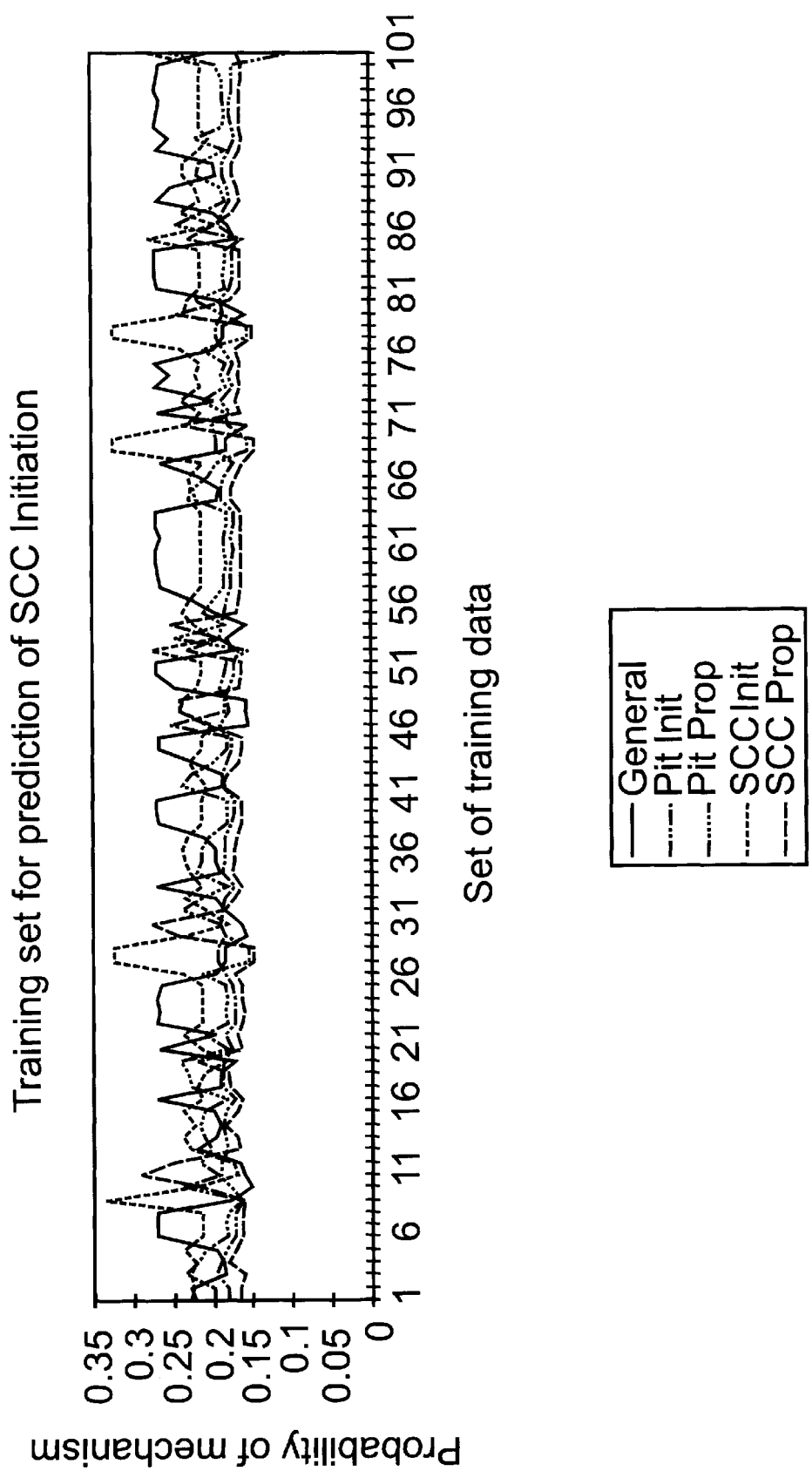
FIG. 41 is the SCC initiation training results plot for the network of FIG. 33.

The plot shown in FIG. 41 was the result of the 1024 point data file with a general corrosion mechanism with SCC Initiation transients present.

Figure 42:
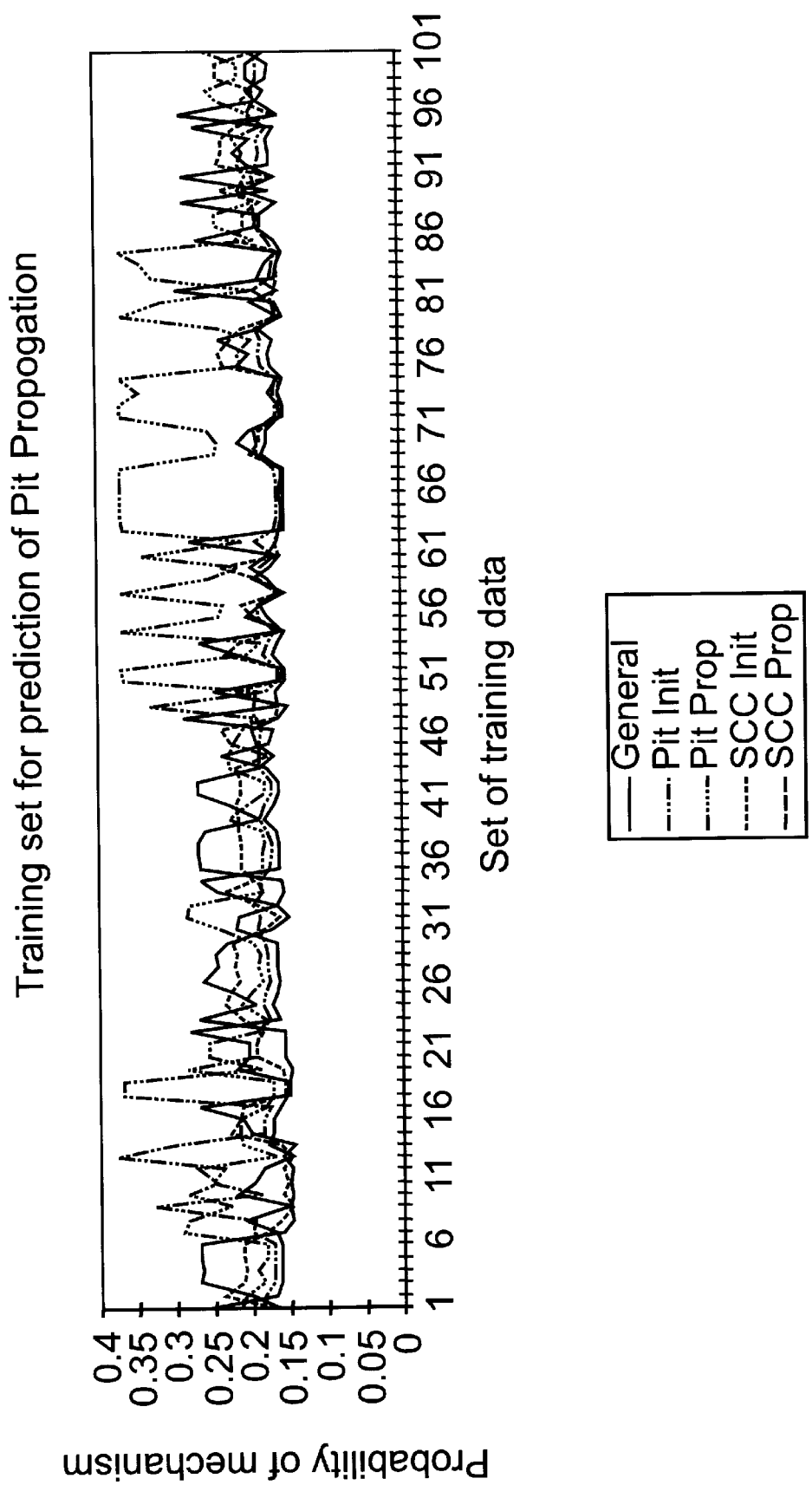
FIG. 42 is the pit propagation training results plot for the network of FIG. 33.

The plot shown in FIG. 42 was derived from a training data file with predominantly Pit Propagation corrosion. The net has also picked up the Pit initiation characteristics present at the start of the file.

Figure 43:
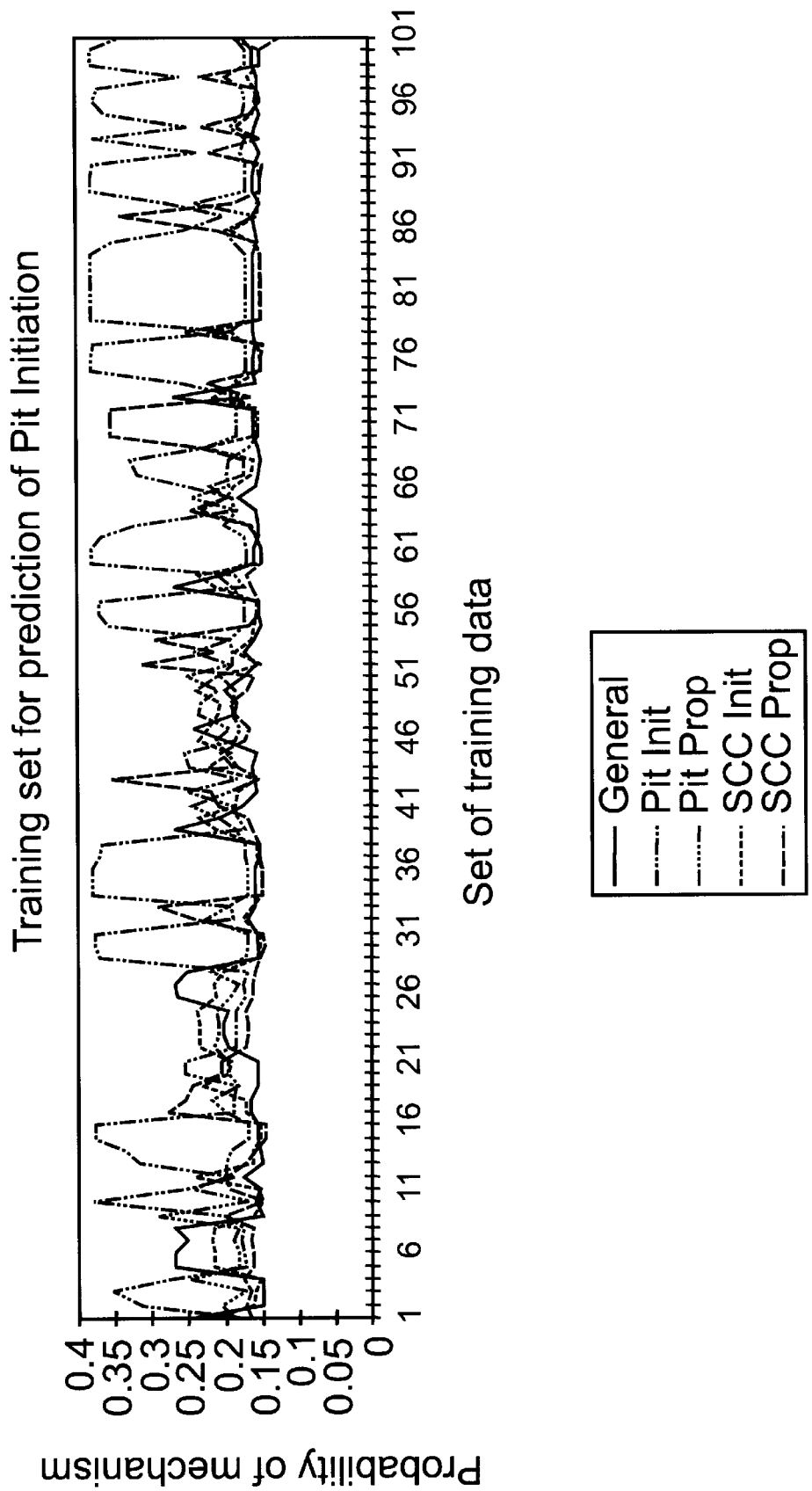
FIG. 43 is the pit initiation training results plot for the network of FIG. 33.

The plot shown in FIG. 43 was derived from a training data file with predominantly Pit Initiation corrosion with an underlying, relatively passive general corrosion rate.

Figure 44:
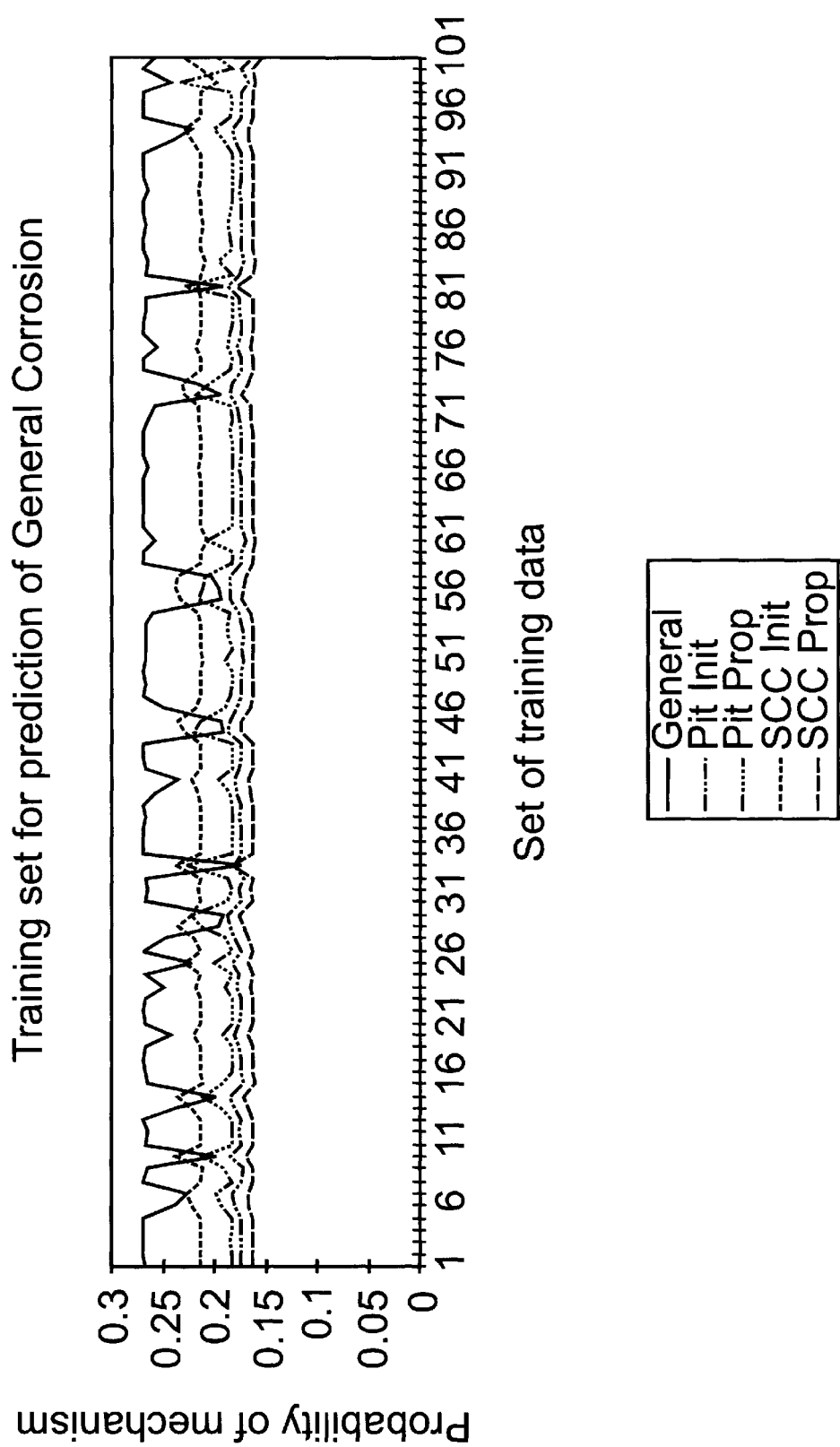
FIG. 44 is the general training results plot for the network of FIG. 33.

The plot shown in FIG. 44 was derived from a training data file with an substantial presence of a low level corrosion rate. This file did not contain any significant presence of another mechanism.

Figure 45:
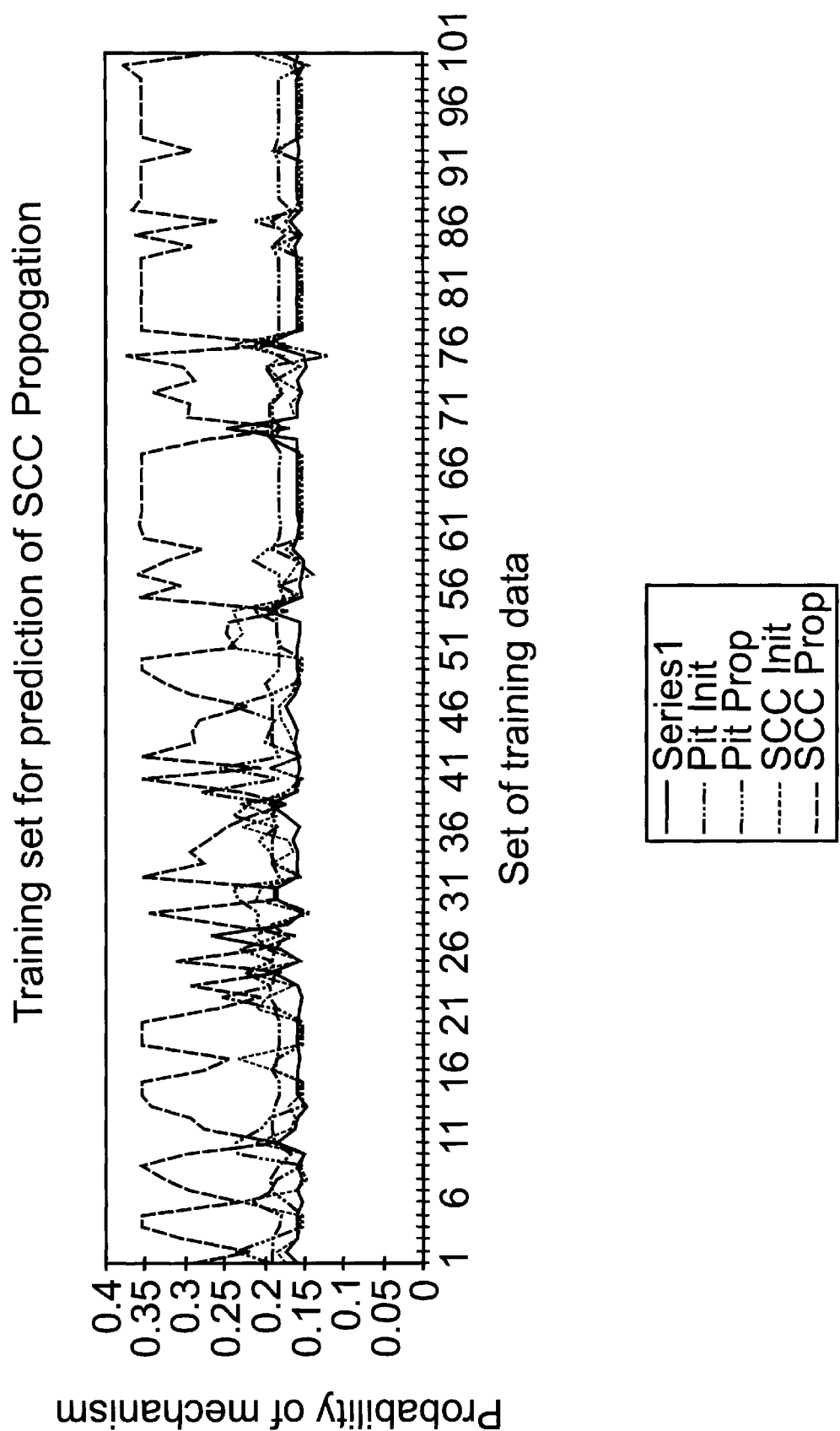
FIG. 45 is the SCC propagation training results plot for the network of FIG. 33.

The plot shown in FIG. 45 was derived from a training data file with predominantly SCC Propagation corrosion.

All of the plots in FIGS. 41 to 45 were derived from the training data and do not really give a clear indication of how well the net will work in real terms. The results give an indication of how well the net has learnt to categorize the training data given into particular corrosion mechanisms. To get a better indication of how well the net would work in real terms, real data file examples were required. A set of three data files containing SCC Propagation, Pit Initiation and Pit Propagation corrosion respectively were used. These files were run through the trained network with the following results.

Figure 46:
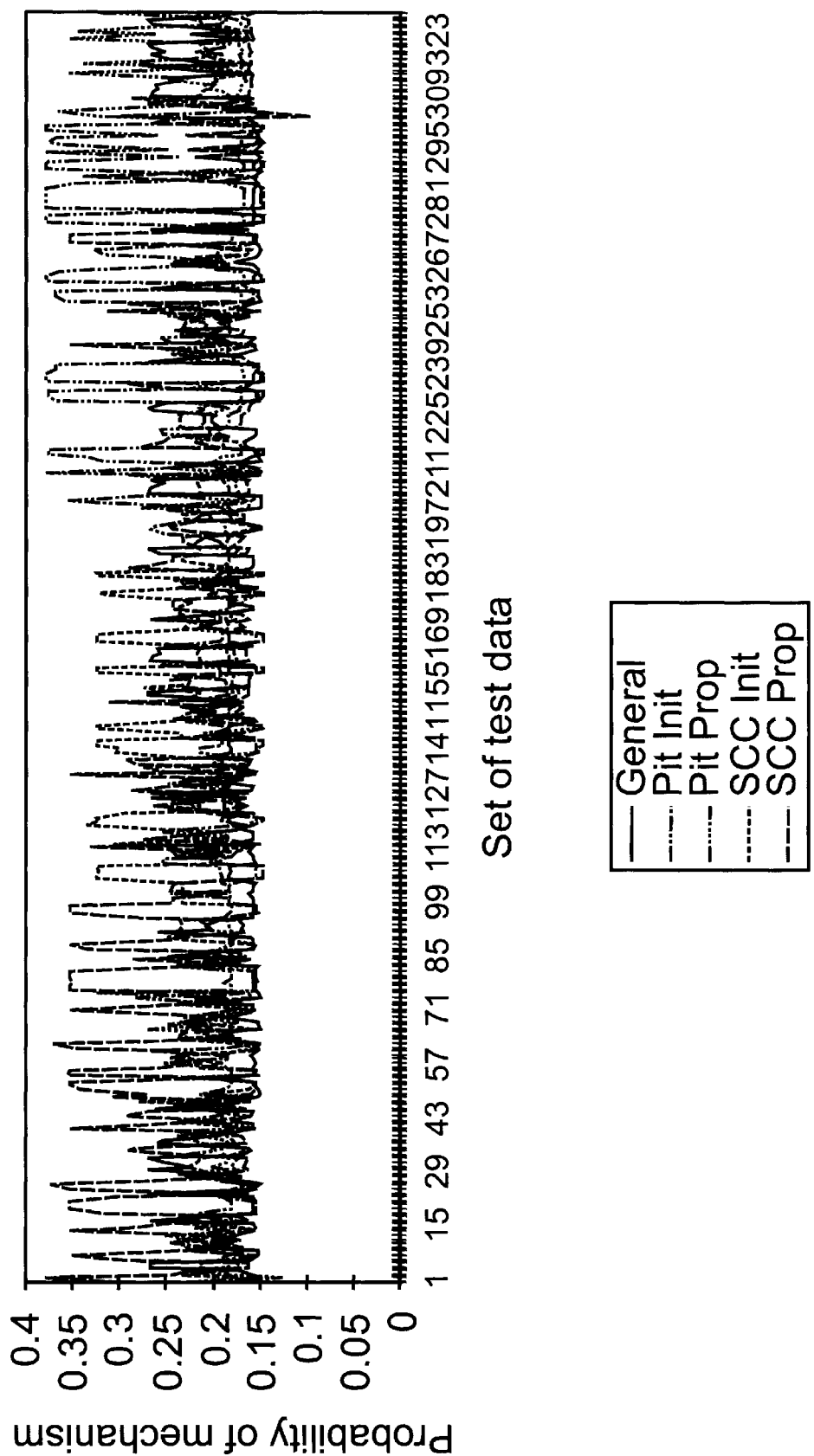
FIG. 46 is plot of a test using several mixed mode files linked together using the network of FIG. 33.

The first file was 2048 datapoints long with an SCC Propagation corrosion mechanism. The neural net of FIG. 33 catagorized this file into two types giving the results as shown in FIG. 46. The first half of the file was categorized as SCC Propagation corrosion whilst the second half was categorized as SCC Initiation corrosion.

The second file was 1024 datapoints long with a Pit Initiation corrosion mechanism. The neural net of FIG. 33 categorized this file as predominantly Pit Initiation corrosion.

The Third file was 300 datapoints long with a Pit Propagation corrosion mechanism. The neural net of FIG. 33 categorized this file as predominantly Pit Propagation corrosion.

The results of this test indicate that the network of FIG. 33 may not be able to distinguish between SCC Initiation and SCC Propagation corrosion. It does however seem highly probable that the data file contained characteristics of both modes as they are related. This could still be a problem however as the amplitude is removed from the signal using Skew and Kurtosis which could possibly remove some of the determining characteristics.

The results of the tests done on the trained network of FIG. 33 were not conclusive. It will be appreciated that the network needs optimizing and the training data set needs adjusted to remove dual mode data sets (data sets with more than one mechanism present). Consequently, the net needed testing on more real data to see if this type of net architecture could recognize the real determinant characteristics of the data.

Figure 47:
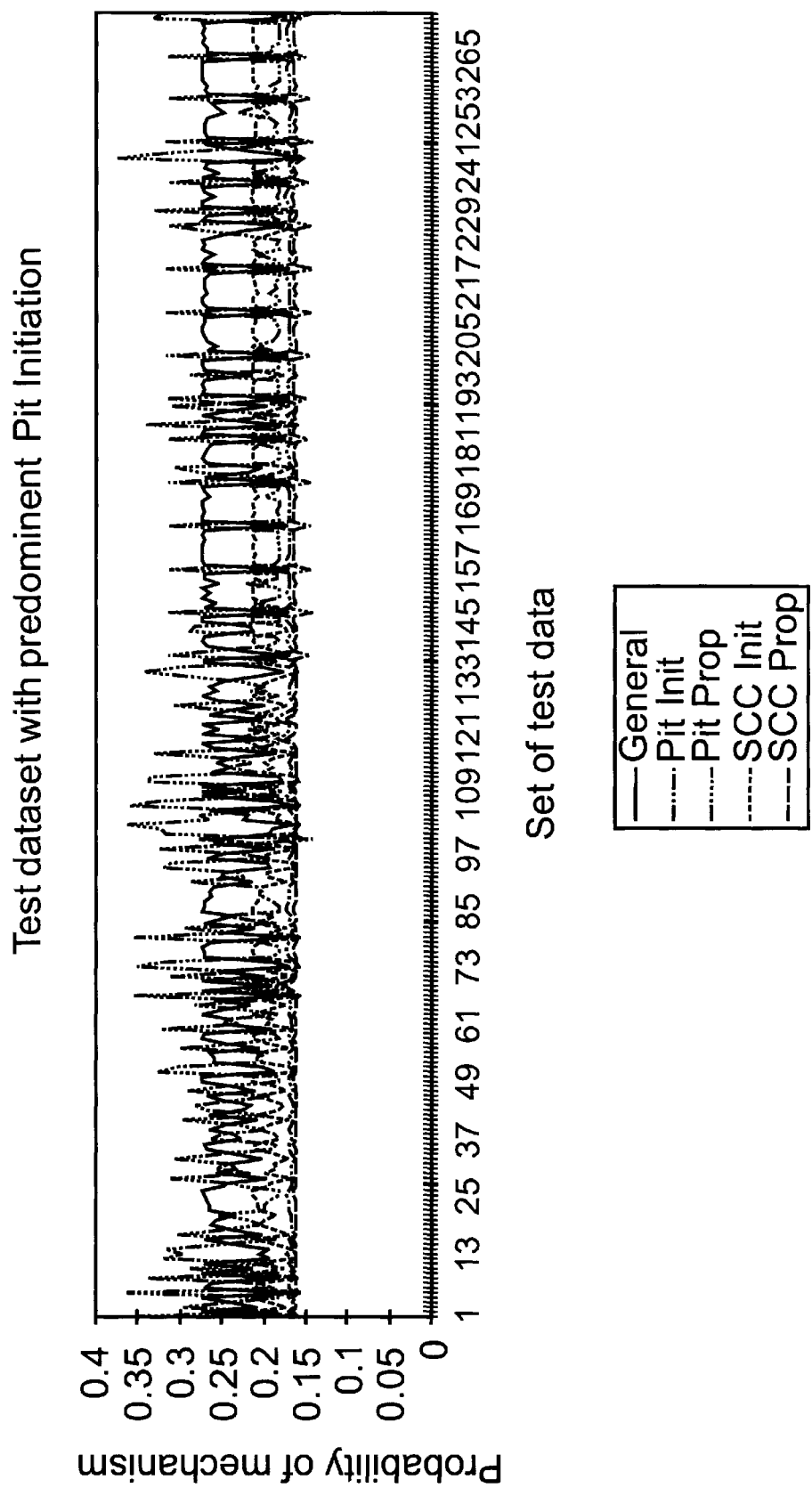
FIG. 47 is the pit initiation training results plot for the network of FIG. 33.

The net of FIG. 33 was run on a file which was predominantly pit initiation attack. The results of this test is shown in FIG. 47. The plot in FIG. 47 shows that there was pit propagation transients present in the data but the main characteristics of the raw data were indicating pit initiation corrosion. This led to the conclusion that the network could not distinguish between pit initiation and propagation corrosion.

Figure 48:
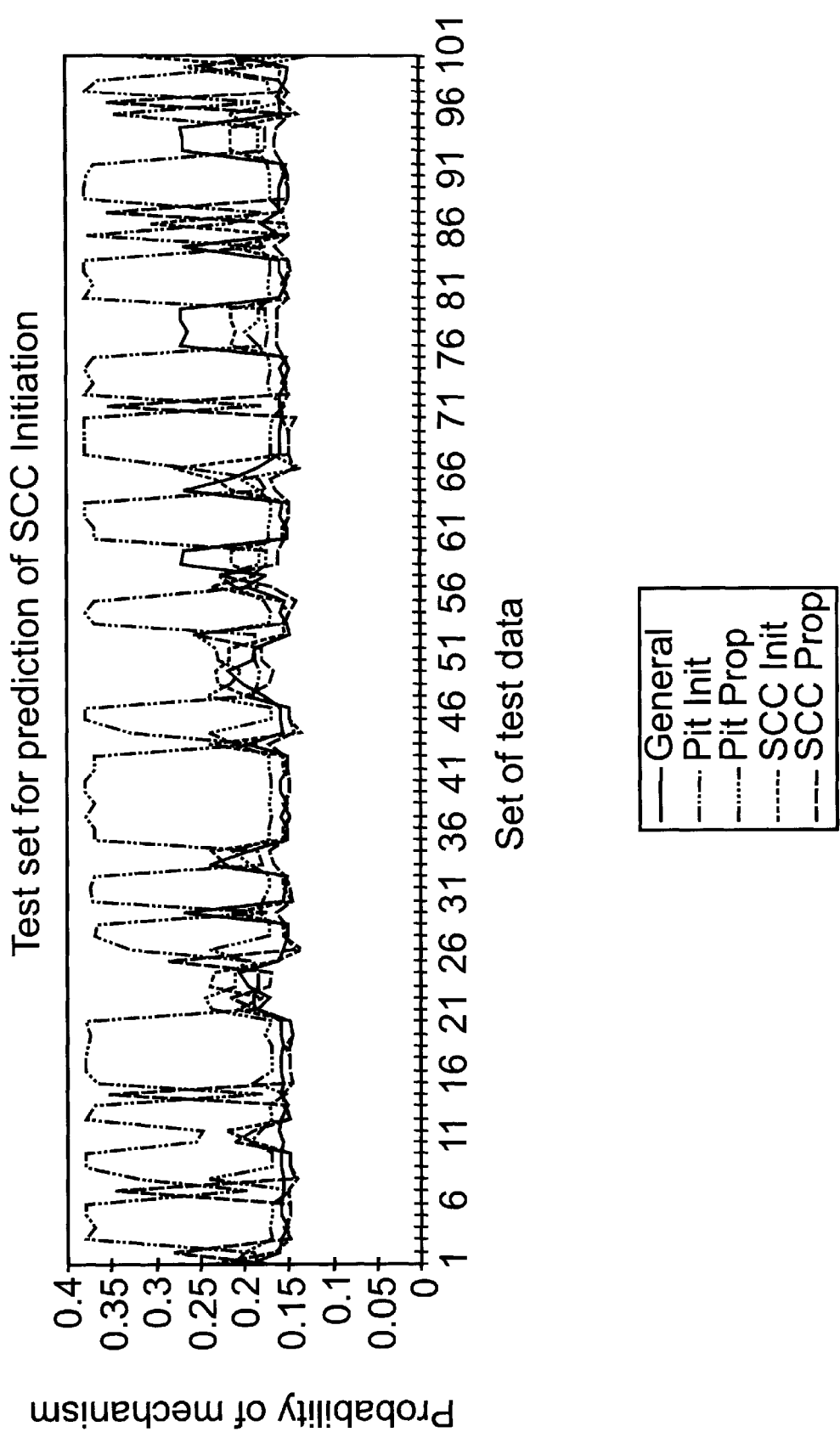
FIG. 48 is a plot of the results from testing the network of FIG. 33 with an SCC initiation training file.

The next step was to test the network on an SCC Initiation file. The results of this test is shown in FIG. 48. The net of FIG. 33 categorized the data file as Pit Initiation not SCC Initiation. It was determined through analysis of the raw potential and current data that the electrodes had been wired in a different way during collection of the data, forcing the current transients to be Cathodic instead of Anodic. This was something that had to be taken into consideration during training and testing, possibly by introducing an extra "Environment" input that will be a Boolean input reflecting the introduction of a stress element in the material under test.

The net of FIG. 33 was then trained using an extra general corrosion data file with a noisier fingerprint. The reason for this is to attempt to filter out the more discrete transients in the determination of the other mechanisms and to allow the net to concentrate on the more significant transients in the pitting and SCC data files. This was done with a general corrosion data file which was customized to produce a very noisy fingerprint that would not be uncommon in the field. The results of a test on the trained net showed that the initiation mechanisms were being categorized as general corrosion as can be seen in FIG. 49, when the trained network is tested on the previously tested SCC initiation data file with the electrodes transposed.

Figure 49:
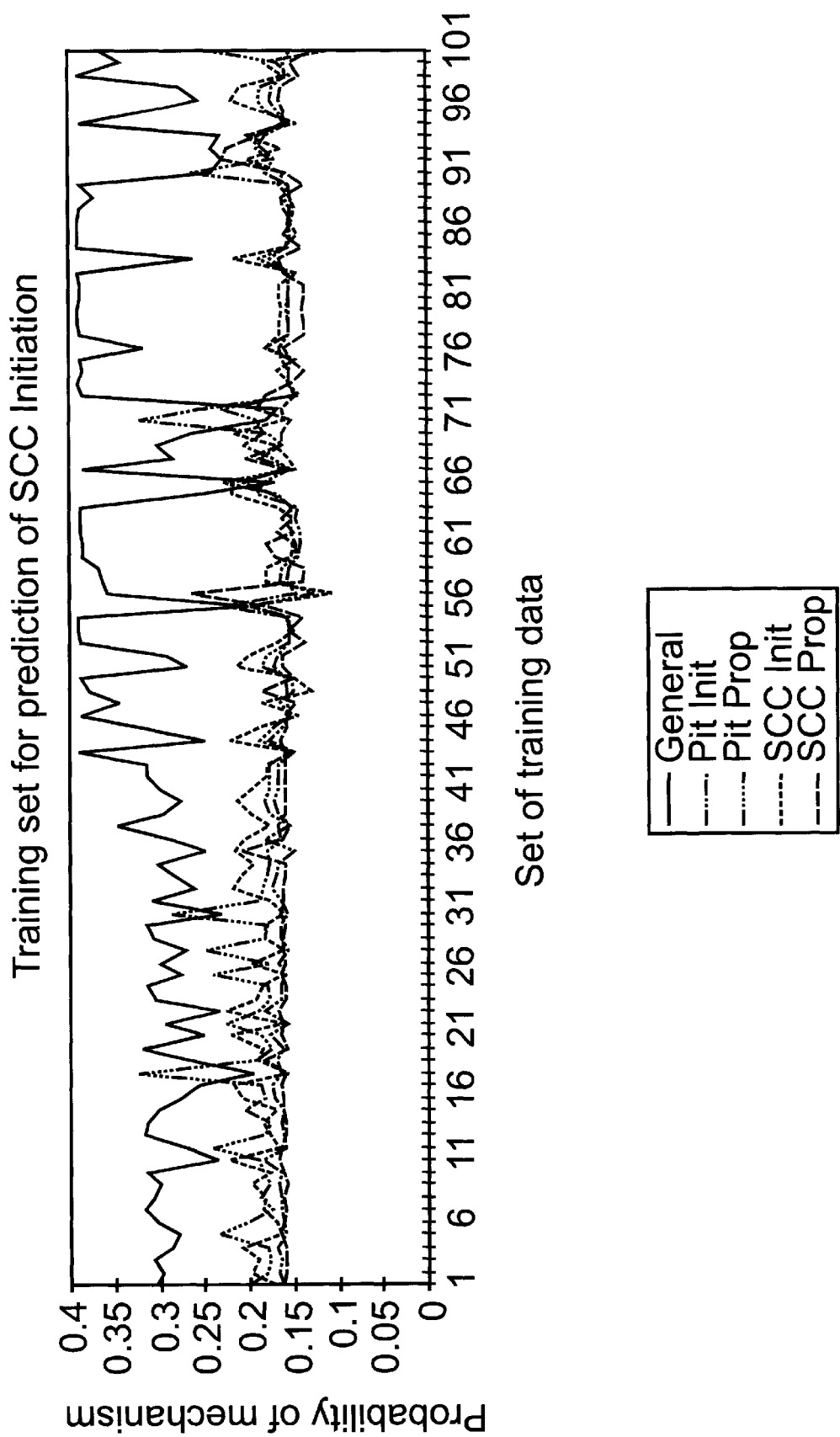
FIG. 49 is a plot of the results from testing the network of FIG. 33 with an SCC initiation training file.
Figure 50:
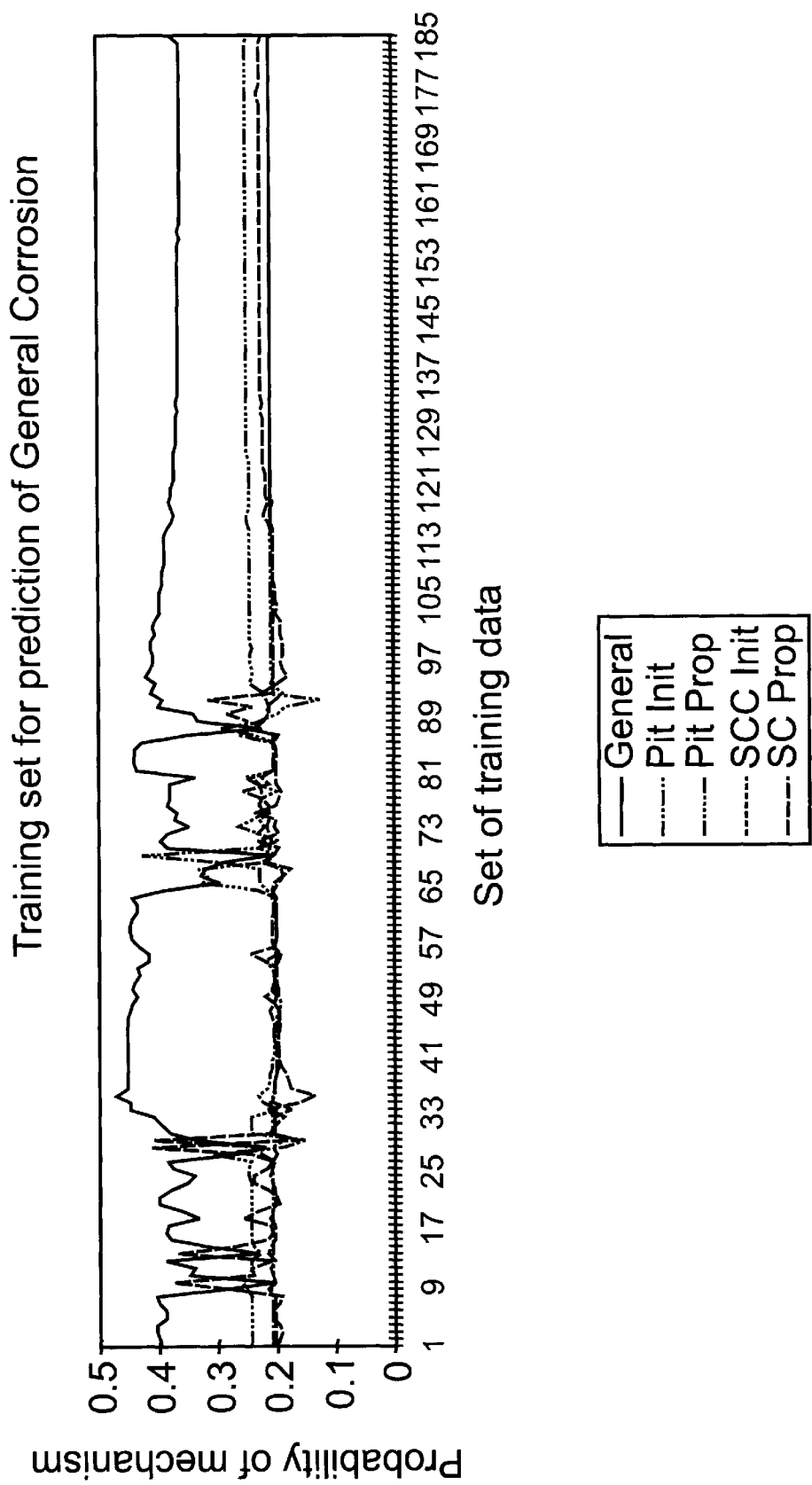
FIG. 50 is a plot of the results from testing the network of FIG. 33 with a general corrosion training file.

The results shown in FIG. 49 show that the net has classified the data as a high rate of general corrosion and therefore the net is having difficulty trying to classify all of the initiation mechanisms. It was not expected that the network would be able to categorize an SCC data file with the electrodes transposed; the test was initially done as to see if the net could find any other discreet differences between the characteristics of the two mechanisms that had been missed by the human eye when the data was being analyzed visually. This did not however prove to be the case.

At this point it became obvious that the network was having difficulty categorizing data with sharp transients such as the initiation mechanisms. The reason for the erroneous categorisation of the initiation mechanisms was due to the input window length that the statistical functions were taking into consideration.

The Skew and Kurtosis functions were taking a twenty point window of raw data and being batched into multiples of ten for input into the net. With the Kurtosis function looking at such a small window of data, it is recognizing very discreet transients in the raw data for noisy general corrosion and classing them as 'peaky', thus giving them high Kurtosis values. If the input window to these functions were to be lengthened to around 100 datapoints, the net result would be a flattening of the data thereby reducing the Kurtosis value for white noise fingerprints. This would not flatten the more important transients however as these are exponentially larger than those of white noise, thus allowing them to be recognized with the Kurtosis function.

The Skewness function would not be altered by the lengthening of the raw data input to the statistics as the datapoints would still have the same distribution around the zero point. This being the case, the Pro-Processing program was altered to change the inputs to the statistics calculations from, 1–10, 2–11 . . . to 1–100, 2–101 . . . see appendix A). This was first tested in MICROSOFT EXCEL™ and as expected the results showed that the general corrosion and flatter portions of the other mechanisms had a significantly smaller Kurtosis value due to their relative small scale in relation to the wider picture. The results of this test can be seen in Appendix C. After visual analysis of the line graph for the output end of the input layer during training, it appeared that the weights in this layer were getting saturated at the negative end. This could be determined by looking at the output for both the input layer 660 and the first hidden layer 662 (see FIG. 33); the plots showed that the values were going off the scale. The solution to this is to change the scale and offset of the link between the input layer 660 and the first hidden layer 662 to 0.5 and 0.5 respectively. This modification enabled the network to take more consideration of the negative trends in the potential, thus taking more consideration over the SCC initiation example that had caused problems earlier due to the transposed wiring of the electrodes. The error tolerances in the learning schedule for the output layer were modified from between 0 and 1 to between 0.0 and 0.8 to allow the network to satisfy the learning criteria at 80% probability of certainty as opposed to 100%.

The net result of this modification is a more distributed attack, with the back propagation technique resulting in a more balanced network. The net will be satisfied that a result is correct with an 80% probability.

The network of FIG. 33 was then trained on the data files with the new pre-processing algorithm (100 point statistics window). The results of this are shown in FIGS. 50 to 54, which are for General corrosion, Pit Initiation corrosion, Pit Propagation corrosion, SCC Initiation corrosion and SCC Propagation corrosion respectively.

As can be seen by the flattening of the traces for both the benign (no mechanism present) and malign (a corrosion mechanism present) mechanisms, the widening of the input window to the statistics functions has removed the problem of discreet transients being taken into consideration. The overall effect results in the trace of the attacking mechanism being more distributed.

Figure 51:
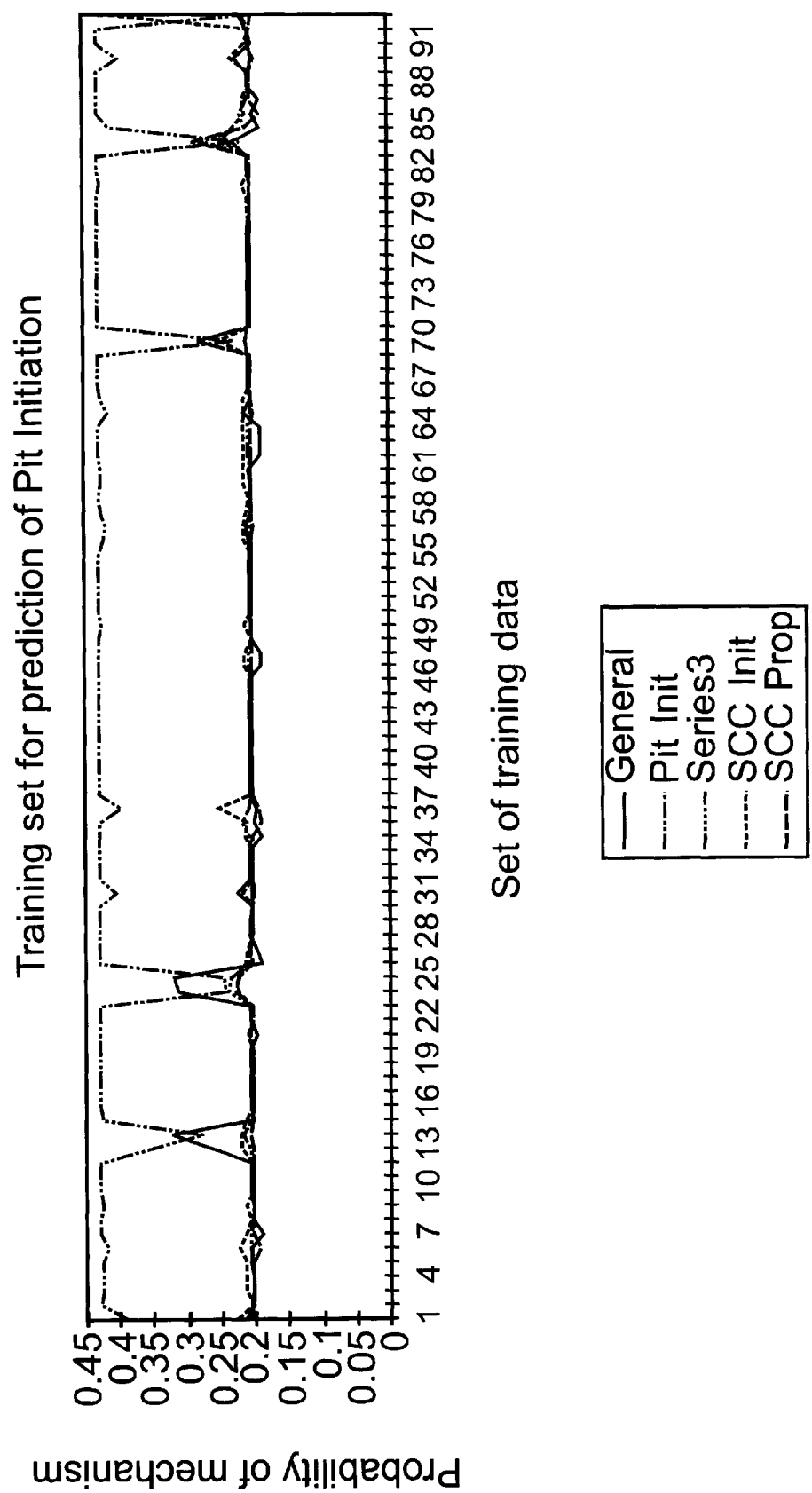
FIG. 51 is a plot of the results from testing the network of FIG. 33 with a pit initiation training file.
Figure 52:
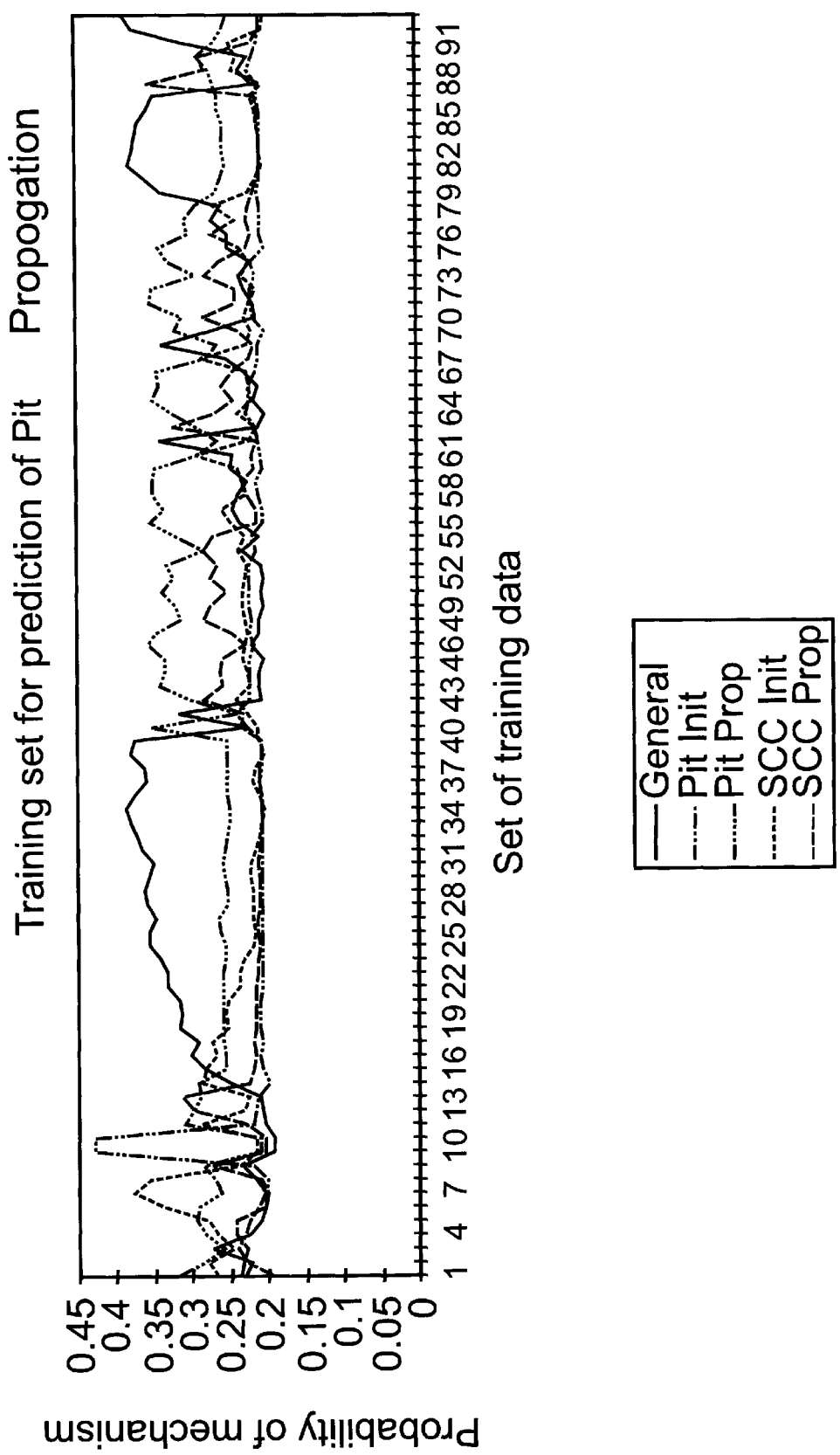
FIG. 52 is a plot of the results from testing the network of FIG. 33 with a pit propagation training file.
Figure 53:
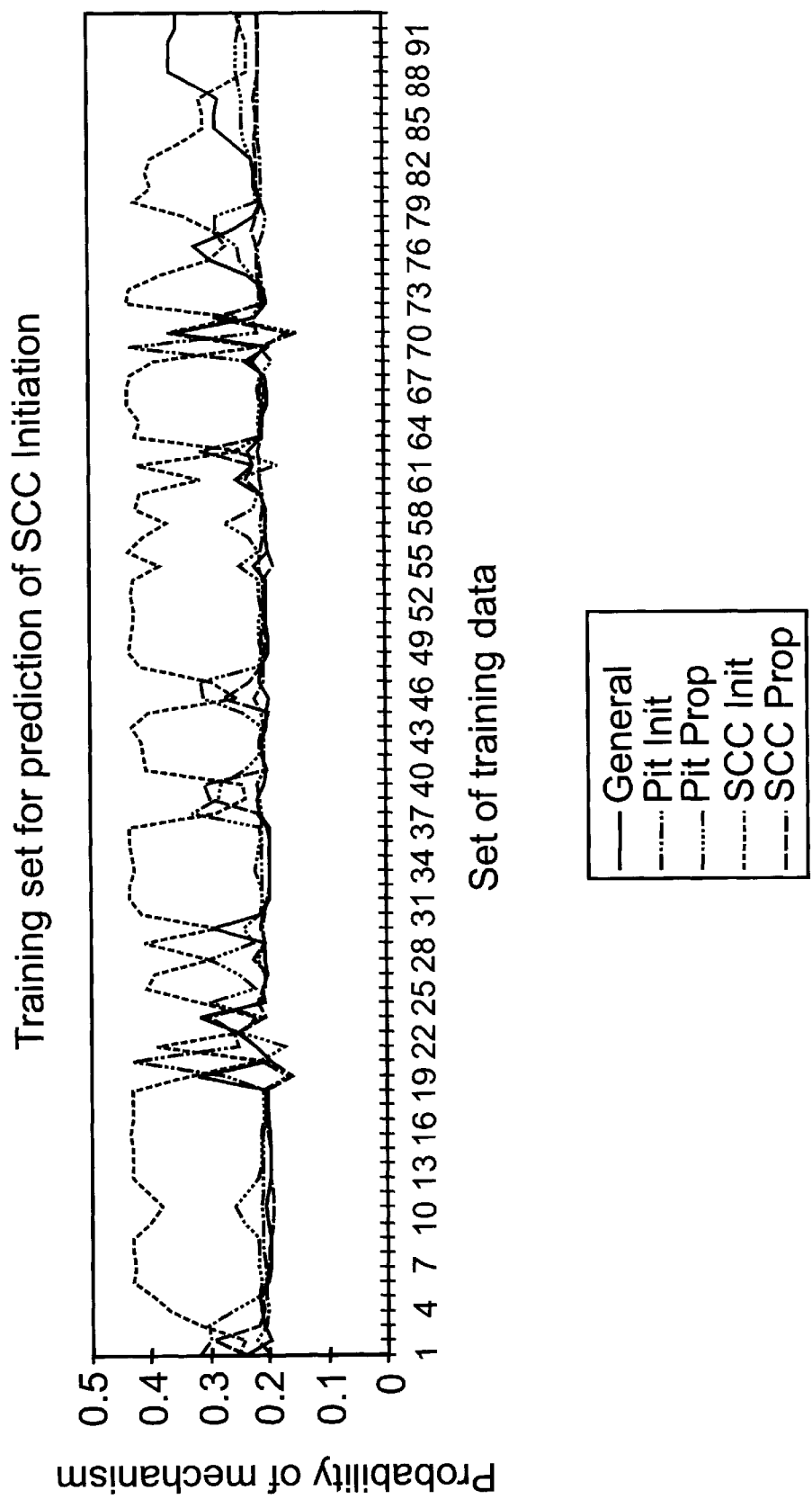
FIG. 53 is a plot of the results from testing the network of FIG. 33 with an SCC initiation training file.
Figure 54:
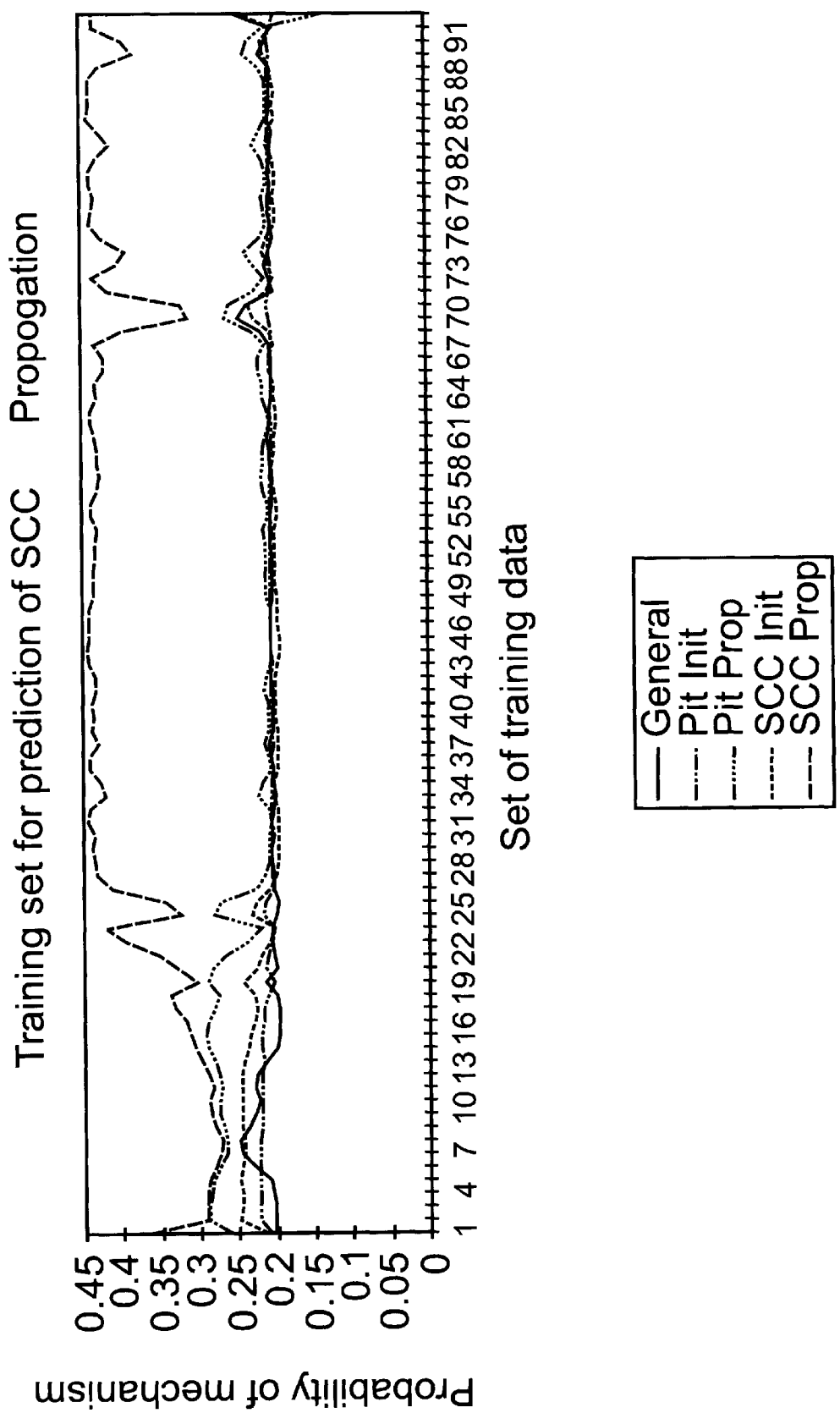
FIG. 54 is a plot of the results from testing the network of FIG. 33 with an SCC propagation training file.

The initial results after training for approximately 370000 cycles were very promising. The net of FIG. 33 had classified all mechanisms except for pit propagation corrosion with a very high degree of probability (FIG. 51). The reason for the exception of the pit propagation classification is that the net is getting confused between approximately 50% general corrosion and pit propagation. As can be seen by the raw data plot shown in FIGS. 55 and 56 (1024 point Pit Propagation training set), although the Pit Propagation would appear to be ambiguous, it is in fact extremely accurate and has a very high correlation to the actual mechanisms present in the raw datafiles, as can be seen from the plots in FIGS. 55 and 56. In these figures, FIG. 55 is a plot of the raw potential Pit Propagation datafile and FIG. 56 is a plot of the raw current Pit Propagation Training datafile.

Figure 55:
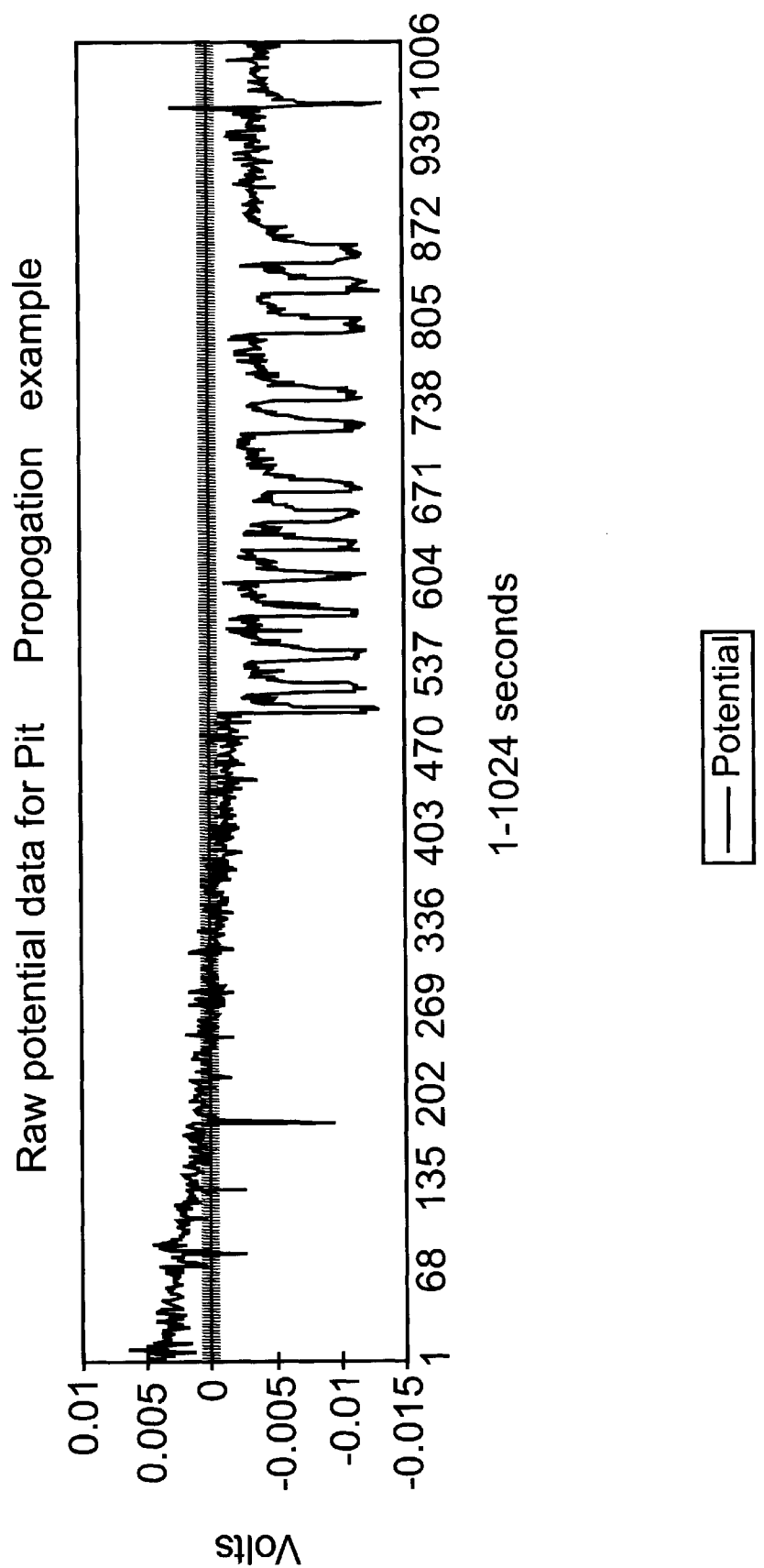
FIG. 55 is a plot of the raw potential data for the pit propagation training.
Figure 56:
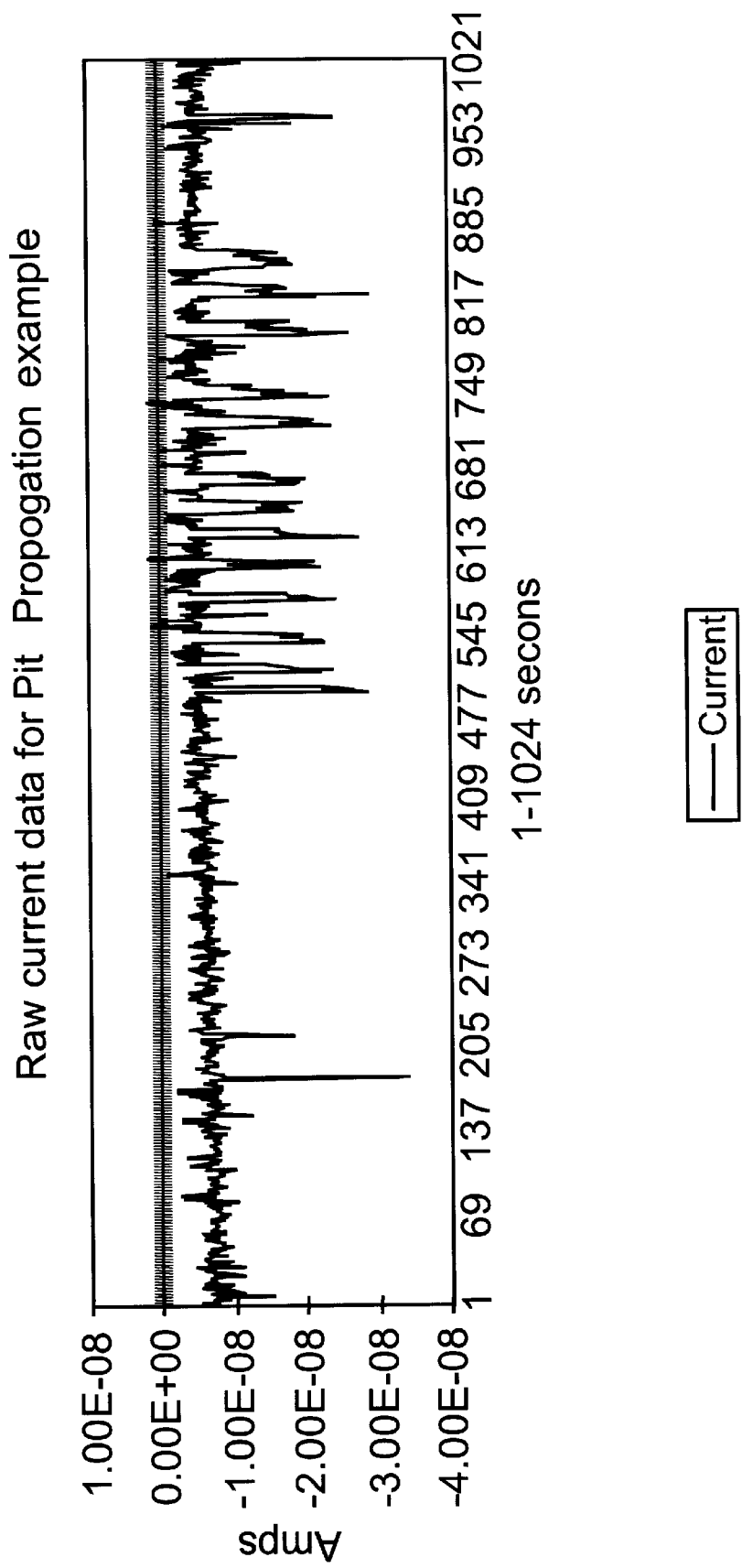
FIG. 56 is a plot of the raw current data for the pit propagation training.

Looking at the correlation between the potential and current plots in FIGS. 55 and 56, at the start of the file there is a single yet significant example of SCC initiation where the potential transient is Anodic whilst the correlating current transient is Cathodic. After this there is a small amount of general corrosion followed by a single large pit initiation fingerprint where both the potential and current transients are Cathodic, the potential transient settling back down to baseline almost immediately. This is typical of pit initiation. The next major portion of the plots show general corrosion. This is followed by a series of pit propagation/re-passivation events signified by the same characteristic as pit initiation, with the corresponding potential taking longer to settle. This signifies a longer period of re-passivation due to a larger amount of material loss. This mechanism is indicative of pit propagation corrosion. At the end of the pit propagation mechanism a small trace of SCC propagation is evident where the potential changes direction from Cathodic to Anodic, with the corresponding current taking a small but significant amount of time to settle back to baseline.

The data shown in FIGS. 55 and 56 indicates how well the net of FIG. 33 had learned using the training data. The net was then tested on some real data. The first test was done on the pit initiation data used earlier. The last net (that of FIG. 32) which attempted to classify this data categorized it as pit propagation instead of initiation. This was due to the problems that the net was encountering at the time when trying to separate initiation from propagation. The results of this test using real data are shown in FIG. 57.

Figure 57:
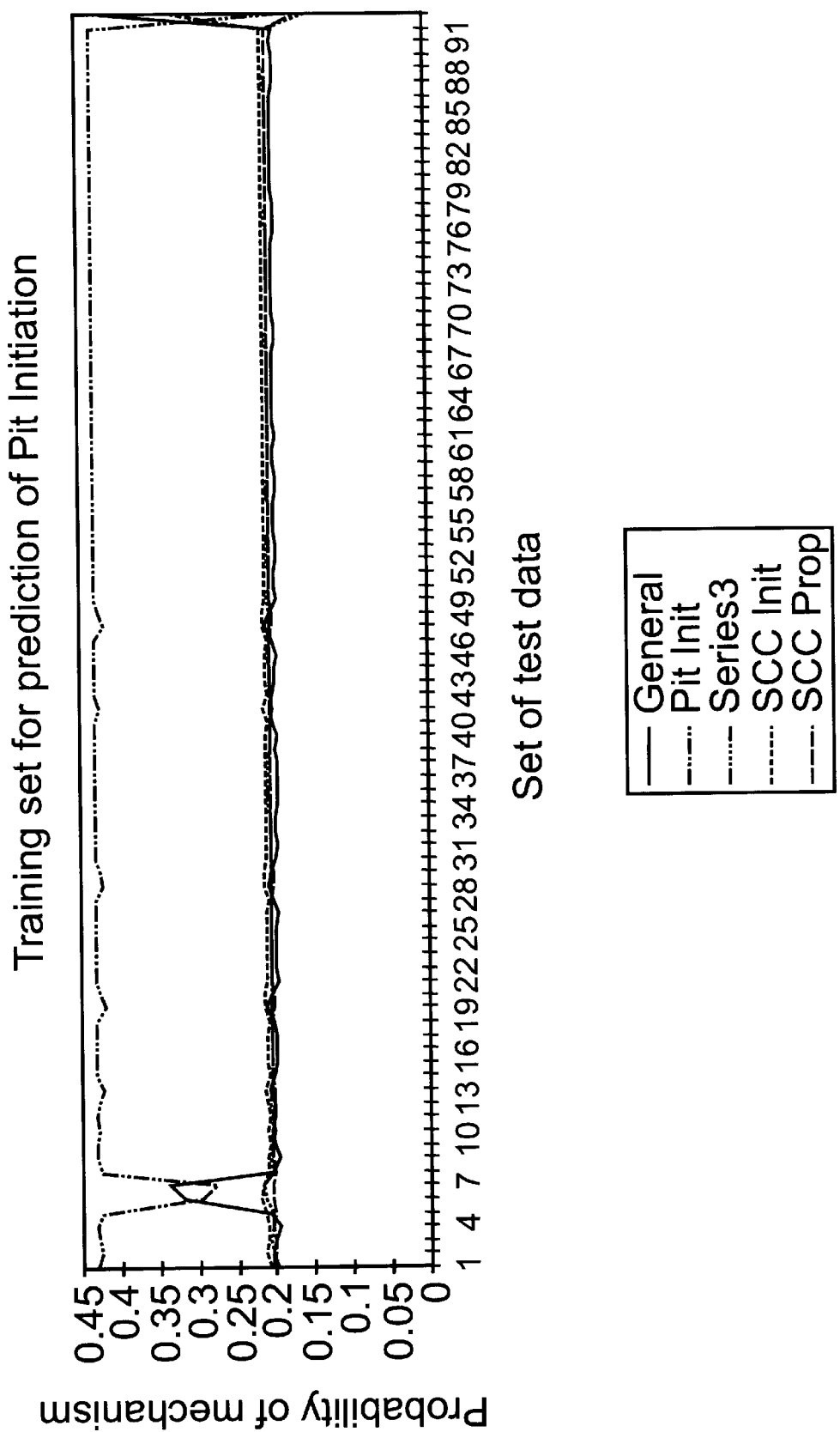
FIG. 57 is a plot of the results from testing the network of FIG. 33 with a pit initiation training file.

As can be seen from FIG. 57, the net has correctly categorized the mechanism as pit initiation. This is due to the changes made to the network after encountering the pit initiation classification problems, along with the widening of the statistics input window to remove the emphasis placed on smaller insignificant transients. These smaller insignificant transients are due to the fact that all metals corrode continuously. The general corrosion mechanism is in fact microscopic pitting on a non-local scale.

After finishing this test, the net was left to train for up to 570000 cycles. This was done to see if leaving the net to settle after it had finished an arbitrary settling period after the training schedule had finished (training schedule finishes at 310000 cycles) made any difference to the results.

This test showed that an elongation of the training period made no difference to the learning and weight settling values of the net. Therefore, once the net has been allowed to settle for an arbitrary period after the training schedule has finished, there would be no advantage in letting the net settle any further.

Altering the training schedule has a very direct effect on the net settling state and time to reach this. If the learning schedule is too fast, the net will settle down very rapidly but it has not been allowed to reach optimum state at each of the various levels in the learning schedule. This will therefore not produce the best results.

Five Output Network Using Statistical Inputs

The network of FIG. 34 was configured and left to train for approximately 2.00 hours before the training schedule had been completed. It was apparent during training that the environment variable was having an effect on the classification within the net. This was seen by observing the classification rates displayed during training. The net of FIG. 34 had split up the pitting and stressed examples in the input sets very early in the training schedule. As expected however, the general corrosion example was being spread over the whole range of outputs before it had been properly classified. This was due to the fact that the general corrosion example was used with the environmental variable set for both settings of stressed and unstressed for general corrosion.

Figure 58:
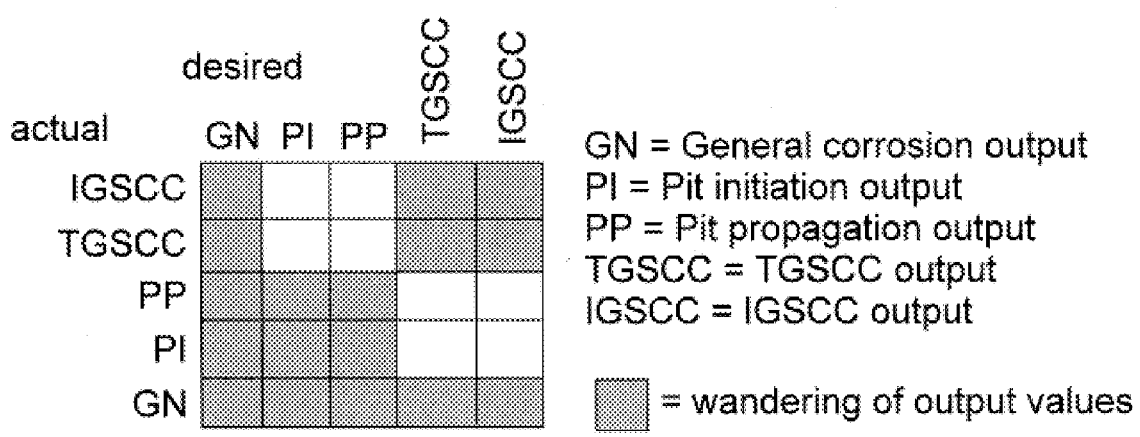
FIG. 58 shows the classification of the output layer of the network of FIG. 34.

FIG. 58 shows that the network was split during training due to the environment variable. The shaded grey areas are the classifications that the network was using during the later stages of the training after it had established the significance of the environment input for stress. FIG. 58 indicates that the network was now not erroneously cross classifying SCC and Pit propagation.

Figure 59:
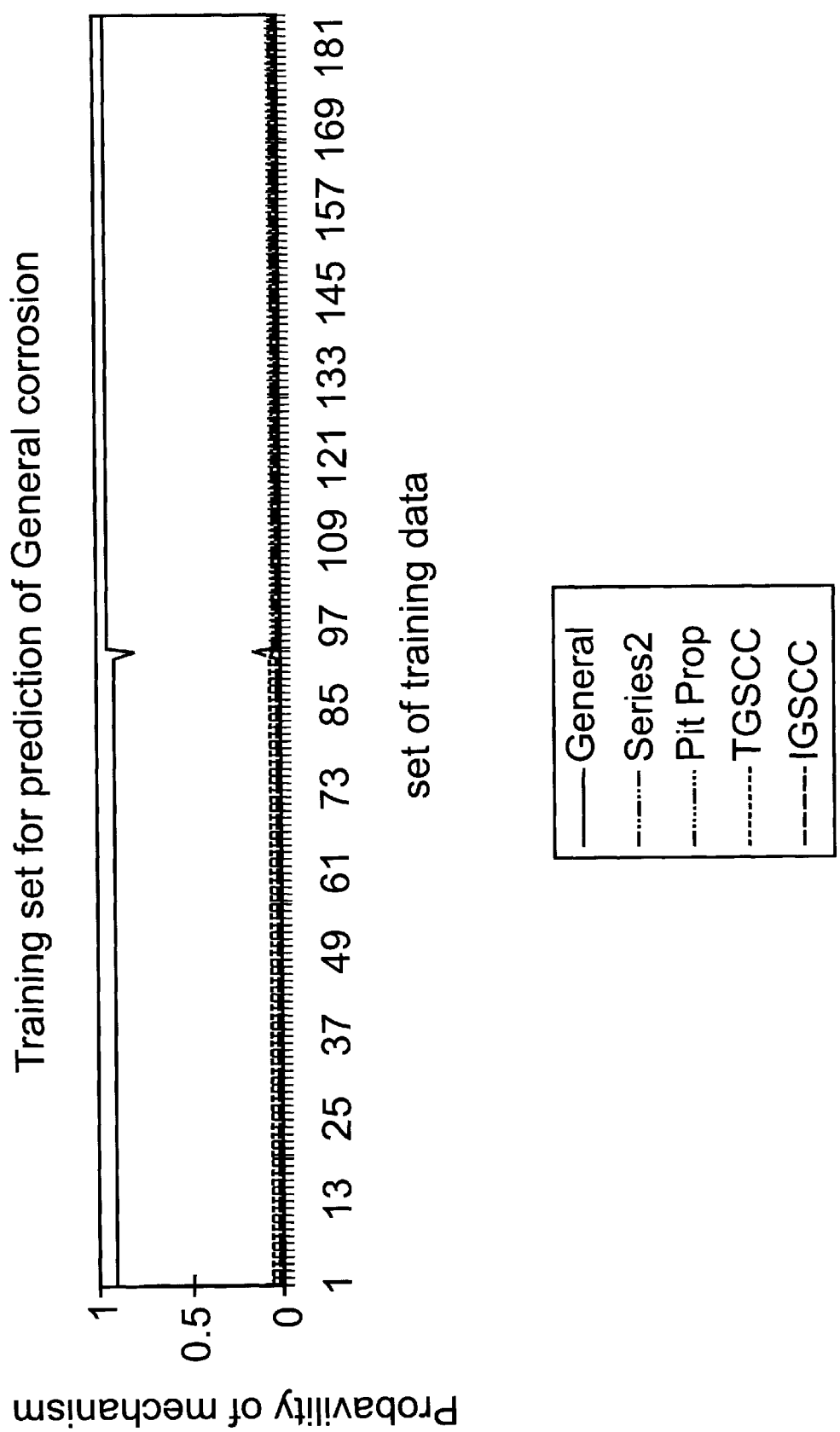
FIG. 59 is a plot of the results from testing the network of FIG. 34 with a general corrosion training file.
Figure 60:
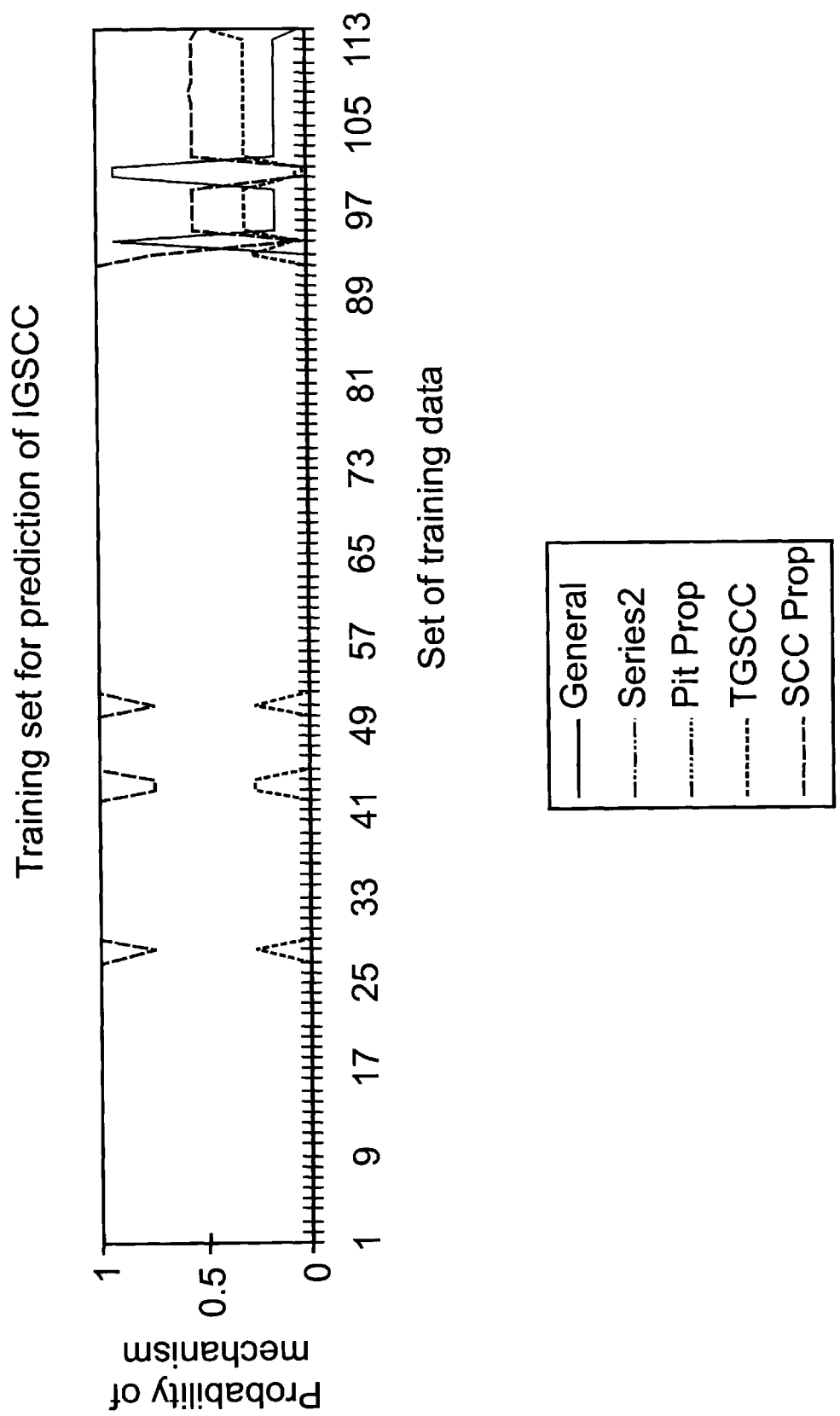
FIG. 60 is a plot of the results from testing the network of FIG. 34 with a intergranular SCC training file.
Figure 61:
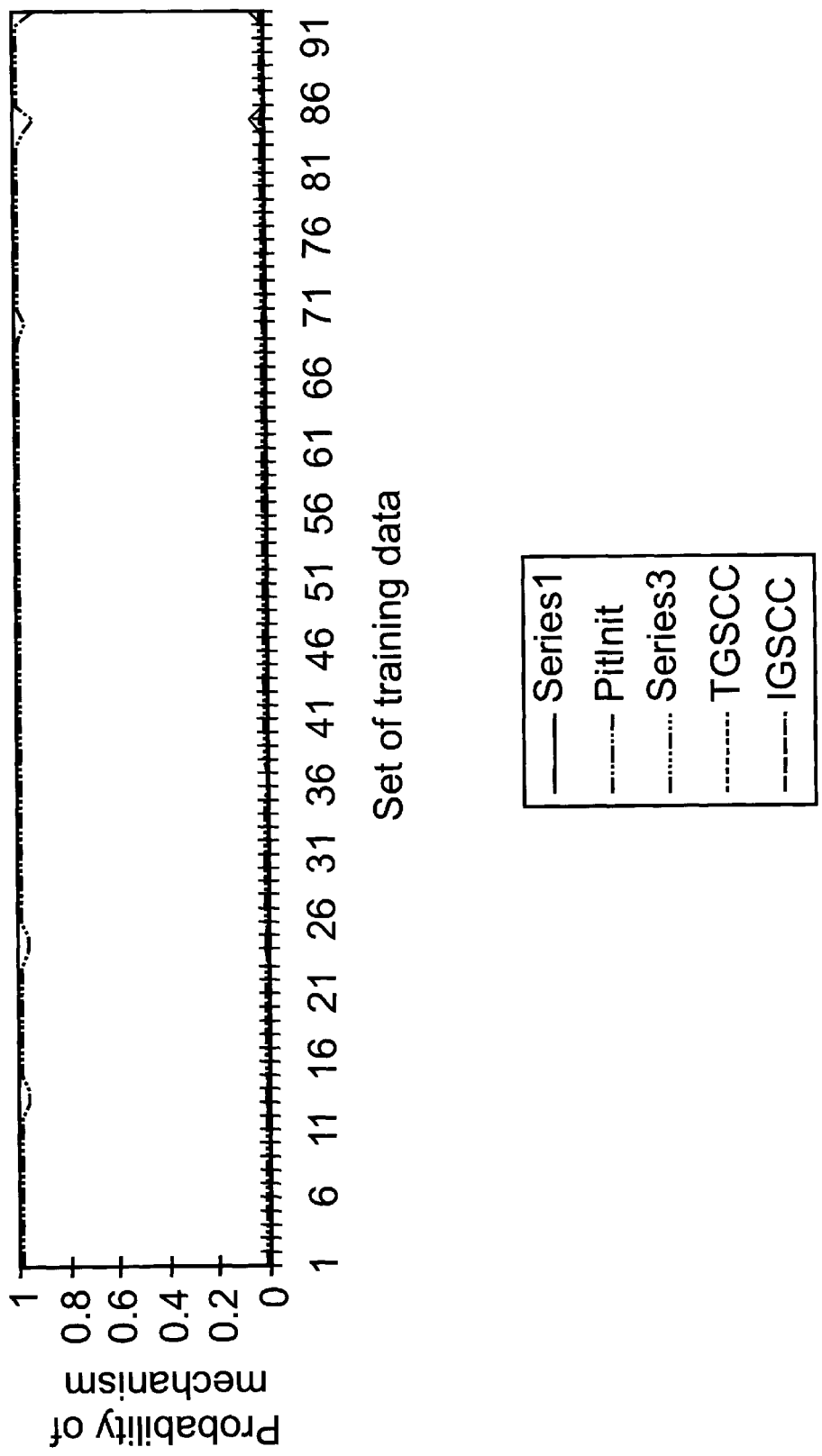
FIG. 61 is a plot of the results from testing the network of FIG. 34 with a pit initiation training file.
Figure 62:
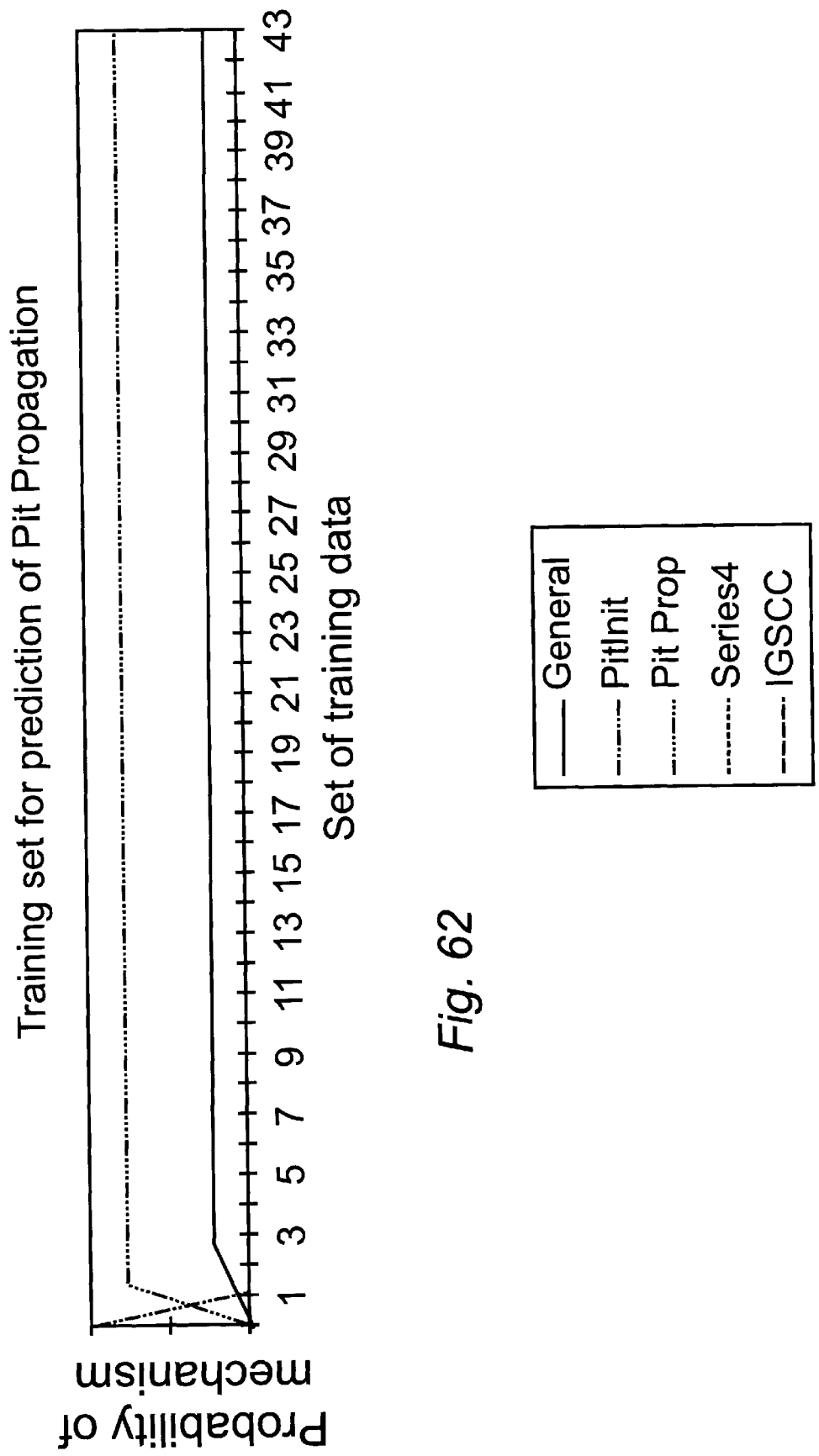
FIG. 62 is a plot of the results from testing the network of FIG. 34 with a pit propagation training file.
Figure 63:
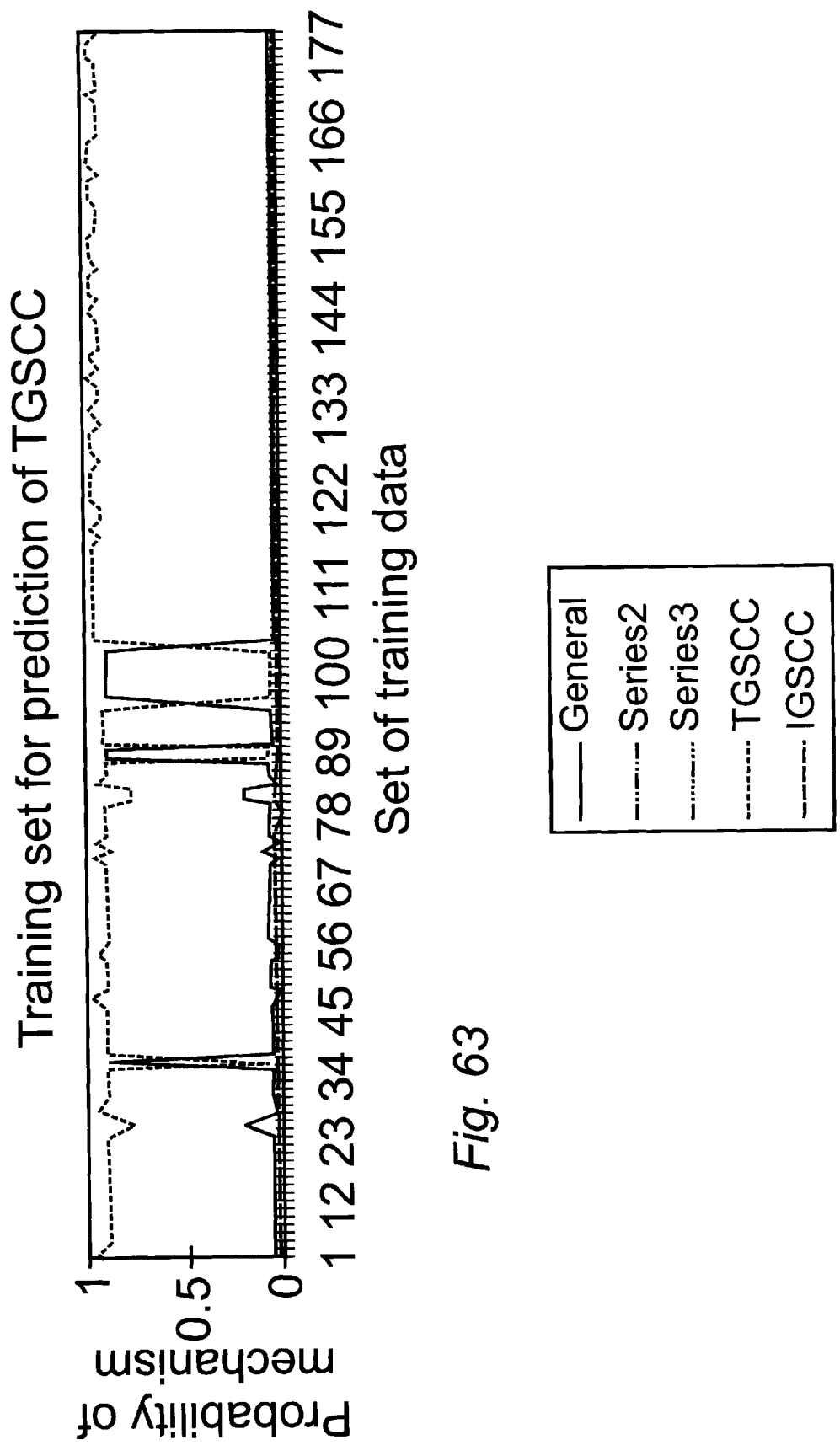
FIG. 63 is a plot of the results from testing the network of FIG. 34 with a transgranular SCC training file.

The network classified the training data with a high degree of probability as can be seen from the results shown in FIGS. 59 to 63. In these figures, FIG. 59 is training file results for general corrosion; FIG. 60 is the training file results for IGSCC corrosion; FIG. 61 is the training file results for Pit initiation corrosion; FIG. 62 is the training file results for Pit propagation corrosion; and FIG. 63 is the training file results for TGSCC corrosion.

The trained net of FIG. 34 was then tested on some datafiles that were not introduced in the training data. For this test, datafiles from real experiments for an IGSCC mechanism were used. The results showed that the net had classified the mechanism as TGSCC. Analysis of the Skew vs. Kurtosis of the IGSCC testing files showed that it did have a very similar fingerprint to those with which the network was trained. As a result of this test, the network of FIG. 34 required modification so that the schema incorporated a splitting of the first hidden layer 662 to allow the net to get a picture of the Skew/Kurtosis relationship before processing the data further.

Five Output Network Using Statistical Inputs

Figure 65:
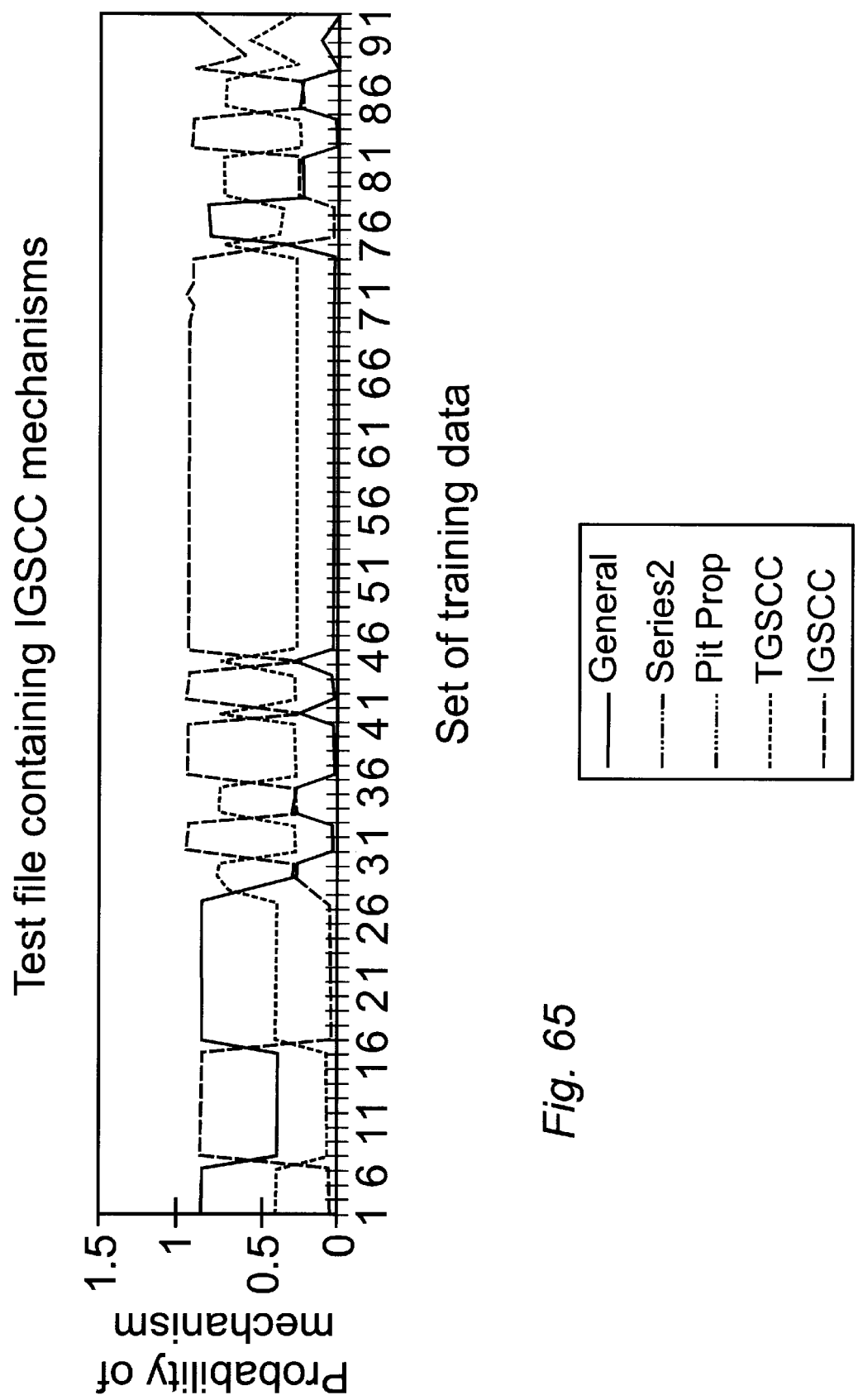
FIG. 65 is a plot of the results from testing the network of FIG. 35 with an intergranular SCC training file.

The testing on the trained net of FIG. 35 showed that although the network configuration changes appeared during training to have made no difference in result classification, the network had used different characteristics and associations in its internal representation to categorize the outputs. The forcing of the net to look at the Skew/Kurtosis relationships before processing further showed that the net was now looking at the correct features. The same testfile as interpreted erroneously in the previous example was now being correctly classified as IGSCC as shown in FIG. 65. All other files were, as in the previous example also being classified correctly.

Figure 64:
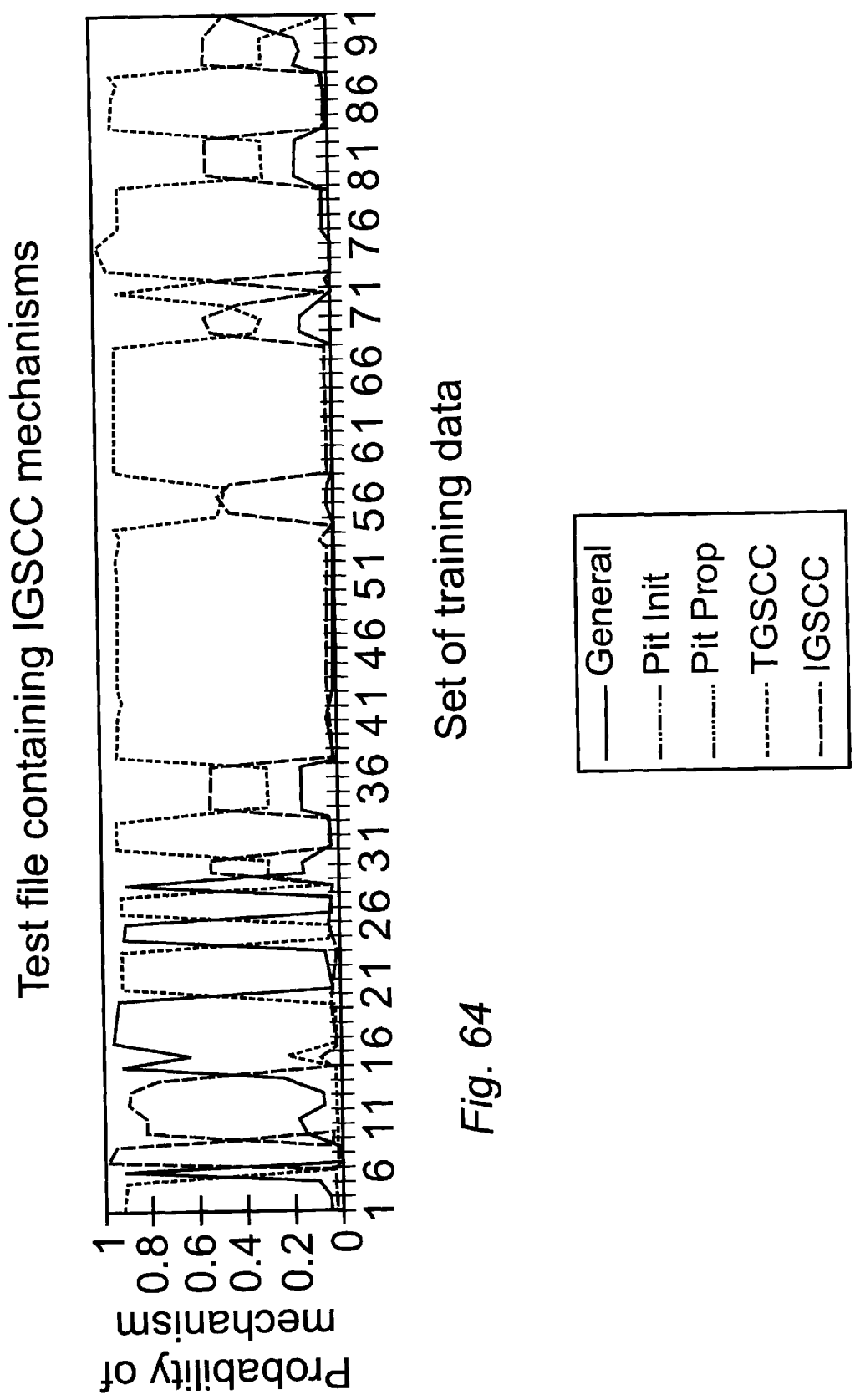
FIG. 64 is a plot of the results from testing the network of FIG. 34 with an intergranular SCC training file.

FIG. 64 shows the results from the previous classification of IGSCC mechanism, and FIG. 65 shows the results of the split hidden layer classification of IGSCC mechanism.

With the system shown in FIG. 35, the mechanism of attack will be diagnosed by correlation of transients of the data, not their respective amplitude. It would be advantageous to have another neural net or expert system that will use the output of the mechanism detection net shown in FIG. 35 as one of its inputs. It may also have as an input the standard deviation of the current and its minimum/maximum values along with the mean and possibly transient width to predict the severity of the corrosion attack. The role of this system would be to give either tailored corrosion rate information depending upon the mechanism, or to give an indication of how severe the localized attack is on the sample.

The testing on the trained net showed that it had used different characteristics and associations in its internal representation to categorize the outputs. The forcing of the net to look at the Skew/Kurtosis relationships before processing further showed that the net was looking at the correct features.

The final network designed uses the signature of the datafile to successfully determine corrosion mechanism; it does not however take into consideration the amplitude of the signal to determine the severity of the attack present in the sample. As a result of this limitation, the network will not distinguish between a severe attack of localized corrosion propagation and a mild attack. This could have been achieved by introducing examples of mild localized attack at input with an output of general corrosion. A separate method of distinguishing the severity of attack should be incorporated for example by using the outputs from the net of FIG. 35 as an input to a further neural net or expert system as previously described.

Thus there is provided a method and apparatus for identifying the corrosion mechanism which does not require the experience and visual ability of trained personnel.

Corrosion damage is monitored using electrochemical sensors in penetrations traversing the wall of a vessel containing an electrolyte, such as the penetrations of a process or pressure vessel, or pipeline. Corrosion damage to the vessel may comprise one or more mechanisms of attack, the characterization of the type or mode of attack may be accomplished by insertion of at least one, but preferably a plurality of electrodes that define electrochemical sensors. A series of electrodes may be used to detect susceptibility of the materials of construction to the various forms of corrosion damage, alternatively, the corrosion activity on the local surface of the vessel, or a specific component, may be monitored using a series of electrode sensors. The electrodes of each subset comprising two electrodes used for monitoring current, these may be for example two identical sections of material of construction, or alternatively one of the electrode pair may be the vessel wall, and in addition a third pseudo reference electrode preferably of the same material as the plant. These electrodes are exposed to the corrosive electrolyte, as is the corroding wall of the vessel. The electrodes and the corroding wall are otherwise electrically insulated, and are wired to a detector circuit developing signals as a function of electrochemical activity due to the effects of the corrosion processes. Electrochemical potential and current, and particularly noise levels and characteristics in the potential and current signals are detected for each electrode sensor subset, and each monitored area of the vessel. The signals are analyzed for assessment of the corrosion rate, mechanism and deterioration of the vessel or component. In this manner the condition of the vessel or corrosion sensors is assessed in a manner that enables identification of the active corrosion mechanisms, facilitating corrective action as may be required.

Modifications and improvements may be made to the foregoing without departing from the scope of the present invention.

```
Program DentoNoise:
{ This program will take a DENIS file of>100 pts. and convert it into }
{ a Neural Nets input file : }
{ n(1)...n(40) = data separated by space }
{ plus an environment variable (1 or 0) for stressed and unstressed
respectively
{ & n1 n2 n3 n4 n5 n. = result required }
{ n1 = General. n2 = Pit Init. n3 = Pit Prop, n4 = TGSCC.n5 = IGSCC }
{ 1 = True, 0 = False }
{}
{}
{ If the denis file is say 300 points, the prog will write the statistics for
the first 100 }
{ poinis to the NNet file as so :
{ 1..100 }
{then}
{ 2..101 }
{ 3..102}
{ up to 201..300 }
{}
{ This simulates a moving window along the datasct for input }
Uses Dos.Statistics:
const
    pointwindow = 100;
```

```
            statswindow = 10;
            IsCurrent = FALSE;IsPotential = TRUE:
        type
            pptarray = ptarray;
            ptarray = array[1..10] of real:
        var
            TheInFile,TheOutFile : Text;
            OutFileName : String;
            TheLine : string;
            TheVal : real;
            NoPoints.counter : Integer;
            ThePointBatch : array[1..pointwindow] of real;
            TheCurKurtBatch : array[1..1024] of pptarray;
            TheCurSkewBatch : array[1..1024] of pptarray;
            ThePotKurtBatch : array[1..1024] of pptarray;
            ThePotSkewBatch : array[1..1024] of pptarray;
            DirInfo : Searchrec:
            DotPos : byte:
            CurrentStatsIndex : integer;
            statindex : integer;
            understress : boolean:
        Procedure ShufflePoints(TheNewVal : real);
        var
            count : integer;
        begin
            for count := 1 to 19 do
            begin
            end:
            end:
            function raiseto(val.power : real) : real;
            { raise val to the power power}
            begin
            if power <= 1 then
                raiseto := val
            else
                raiseto := raiseto(val.power=1)*val;
        end:
        function mean : real:
        var
            count : integer:
            sum : real:
        begin
            sum := 0;
            for count := 1 to pointwindow do
            begin
                sum := sum + thepointbatch[count];
            end:
            sum := sum / pointwindow;
            mean := sum:
        end:
        function variance : real;
        var
            presumeval.sumval : real:
            count : integer;
            theman : real;
        begin
            presumval:=0:sumval :=0:
            themean := mean:
            presumval := 1/(pointwindow);
            for count := 1 to pointwindow do
            begin
                sumval := sumval + (raiseto((thepointbatch[count]-themean).2))
            end;
            variance := presumval * sumval:
        end:
        function thirdmoment : real:
        var
            presumval.sumval : real:
            count : integer:
            themcan : real:
        begin
            presumval:=0:sumval :=0:
            themean := mean:
            presumval :=1/(pointwindow):
            for count :=1 to pointwindow do
        begin
        end:
        thirdmoment := presumval * sumval;
        end:
            function fourthmoment : real:
            var
                presumval.sumval : real:
                count : integer;
                themean : real:
            begin
                presumval:=0:sumval :=0:
                themean := mean:
                presumval := 1/(pointwindow):
                for count :=1 to pointwindow do
                begin
                    sumval : =sumval + (raiseto((thepointbatch[count]-themean),4))
                end;
                fourthmoment := presumval * sumval;
            end:
            function Skew : real;
            var
                sumval : real:
            begin
                sumval :=thirdmoment/raiseto(variance,2/3);
                skew := sumval:
            end:
            function kurtosis : real;
            var
                sumval : real;
            begin
                sumval :=fourthmoment/raiseto(variance.2);
                kurtosis :=sumval;
            end:
            Procedure CalcPointBatch(Potential : boolean);
            begin
                ifPotential then
                begin
                    ThePotKurtBatch[statindex][CurrentStatsIndex] := kurtosis;
                    ThePotSkewBatch[statindex][CurrentStatsIndex] := Skew;
                end else
                begin
                    TheCurKurtBatch[statindex][CurrentStatsIndex] := kurtosis;
                    TheCurSkewBatch[statindex][CurrentStatsIndex] := Skew;
                end:
                inc(CurrentStatsIndex);
            end:
            Procedure WritePointBatch:
            var count : integer:
                value : real:
                tempstr : string;
            begin
                for counter := 1 to statindex do
                begin
            { write the current stats to the file in batches of 10 }
            { 10 Kurtosis, 10 Skew }
                for count := 1 to 8 do
                begin
                    write(TheOutFile,TheCurKurtBatch[counter][count]);
                    write(TheOutFile,");
                end:
                WriteIn(TheOutFile);
                Write(TheOutFile,'&');
                for count := 9 to 10 do
                begin
                    write(TheOutFile,TheCurKurtBatch[counter][count]);
                    write(TheOutFile,");
                end:
                writedIn(TheOutFile);
                Write(TheOutFile,'&');
                for count := 1 to 8 do
                begin - -.
                    write(TheOutFile,TheCurSkewBatch[counter][count]);
                    write(TheOutFile,");
                end:
                WriteIn(TheOutFile);
                Write(TheOutFile,'&');
                for count := 9 to 10 do
                begin
                    write(TheOutFile,TheCurSkewBatch[counter][count]);
                    write(TheOutFile,");
                end;
                write(TheOutFile);
                Write(TheOutFile,'&');
```

```
{ write the potential stats to the file in batches of 10 }
{ 10 Kurtosis . 10 Skew }
    for count := 1 to 8 do
    begin
        write(TheOutFile,ThePotKurtBatch[counter][count]);
        write(TheOutFile,'');
    end:
    WriteIn(TheOutFile):
    Write(TheOutFile,'&');
    for count :=9 to 10 do
    begin
        write(TheOutFile,ThePotKurtBatch[counter][count]);
        write(TheOutFile,'');
    end:
    writeIn(TheOutFile);
    Write(TheOutFile,'&');
    for count :=1 to 8 do
    begin
        write(TheOutFile,ThePotKurtBatch[counter][count]);
        write(TheOutFile,'');
    end:
    for couut := 9 to 10 do
    begin
        write(TheOutFile,ThePotKurtBatch[counter][count]);
        write(TheOutFile,'');
    end:
{ put a flag in at the end to say if the sample is under
stress or not. 1 = TRUE. 0 = FALSE }
    tempstr := copy(dirinfo.name.1,3);
    if (copy(tempstr.1,2) = 'TG') or (copy(tempstr,1,2) = 'IG')
        or (copy(tempstr,1,3) = 'GE2') then
    begin
        write(theoutfile,'1');
    end else
    begin
        write(theoutfile.'0');
    end:
{————————————}
    writeIn(TheOutFile);
{ write the expected results for the stats of the denis file for }
{ supervised learning on the net }
    if copy(dirinfo.name.1,3) = 'TGI'then
    begin
        WriteIn(TheOutFile,'& 0 0 0 1 0') { SCC (Trans Granular Init)
            Output }
    end
    else
    begin
        if copy(dirinfo.name,1,2) = 'PI'then
        begin
            WriteIn(TheOutFile,'& 0 1 0 0 0') { Pit Initiation Output }
        end else
        begin
            if copy(dirinfo.name,1,2) = 'PP'then
            begin
                WriteIn(TheOutFile,'& 0 0 1 0 0') { Pit Propogation Output }
            end else
            begin
                if copy(dirinfo.name,1,3) = 'TGP'then
                begin
                    WriteIn(TheOutFile,'& 0 0 0 1 0') { SCC (Trans Granular
                        Prop) Output }
                end else
                begin
                    if copy(dirinfo.name,1,3) = 'IGI'then
                    begin
                        WriteIn(TheOutFile,'& 0 0 0 0 1') { SCC (Trans Granular
                            Prop) Output }
                    end else
                    begin
                        if copy(dirinfo.name,1,3) = 'IGP' then
                        begin
                            WriteIn(TheOutFile,'& 0 0 0 0 1') { SCC (Trans Granular
                                Prop) Output }
                        end else
                            WriteIn(TheOutFile,'& 1 0 0 0 0'); { General Corrosion Output }
                        end;
                    end;
                end
            end
        end
    end
    dispose(ThePotKurtBatch[counter]);
    dispose(ThePotSkewBatch[counter]);
    dispose(TheCurKurtBatch[counter]);
    dispose(TheCurSkewBatch[counter]);
    end:
end;
begin
    CurrentStatsIndex := 1;
    if paramount = 1 then
    begin
{ Open the output file for noise data }
        OutFileName :=paramstr(1)+'\test.nna':
        Assign(TheOutFile,OutFileName):
        ReWrite(TheOutFile);
{ Find first input file }
        FindFirst(paramstr(1)+'\*.?? ,ArchiveDirInfo);
        While DosError = 0 do
        begin
            statindex := 1;
            new(ThePotKurtBatch[statindex]);
            new(ThePotSkewBatch[statindex]);
            Assign(TheInFile.paramstr(1)+'\'+DirInfo.name);
{ Get Rid Of Titles etc. }
            Reset(TheInFile);
            ReadIn(TheInFile);
            ReadIn(TheInFile);
{ Read in the number of points sampled }
            ReadLn(TheInFile,TheLine);
            DotPos := Pos('
            TheLine := copy(TheLine,I,DotPost-1);
            val(TheLine.NoPoints.counter);
            if NoPoints > pointwindow then
            begin
{ Read in the potential values and calc stats of a 20 point window }
{ do this in batches of 100 putting into a 2 dim array; then inc the }
{ second index to put into batches of 10 }
                for counter := 1 to pointwindow do
                begin
                    ReadIn(TheInFile,ThePointBatch[counter]);
                end;
                CalcPointBatch(IsPotential):
                for counter :=pointwindow+1 to NoPoints do
                begin
                    ReadIn(TheInFil.,TheVal);
                    ShufflePoints(TheVal);
                    CalcPointBatch(IsPotential);
{ inc statindex to set to next batch of 10 stats in array }
                    if CurrentStatsIndex > 10 then
                    begin
                        currentstatsindex :='1;
                        new(ThePotSkewBatch[statindex]);
                    end:
{————————————}
                end:
{ re initialise counter varaibles }
                statindex := 1:
                currentstatsindex := 1:
                new(TheCurKurtBatch[statindex]);
                new(TheCurSkewBatch[statindex]);
{————————————}
{get rid of the pre-defined stats in the DENIS file }
                readIn(TheInFile);
{————————————}
{ Read in the current values and calc stats of a 20 point window }
{do this in batches of 10 putting into a 2 dim array; then inc the }
{second index to put into batches of 10 }
                for counter := 1 to pointwindow do
                begin
                    ReadIn(TheInFile,ThePointBatch[counter]);
                end
                CalcPointBatch(IsCurrent);
                for counter := pointwindow+1 to NoPoints do
                begin
                    ReadIn(TheInFile.TheVal);
                    ShufflePoints(TheVal);
                    CalcPointBatch(IsCurrent);
{ inc statindex to set to next series of stats in array }
```

-continued

```
    if CurrentStatsIndex> 10 then
    begin
        currentstatsindex := 1:
        inc(statindex);
        new(TheCurKurtBatch[statindex]);
        new(TheCurSkewBatch[statindex]);
    end:
{————————————}
        end
    end
{ write the stats (both pot and curr) to .nna trainding file for }
{ the fill DENIS file}
    WritePointBatch;
{————————————}
    Close(TheInFile);
    FindNext(Dirinfo);
    end:
    Close(TheOutFile);
  end:
end:
```

What is claimed is:

1. A method for identification of corrosion of a metal object, comprising the steps of providing electrode means capable of generating electrochemical noise signals, and analyzing the statistical distribution of said noise signals to provide an indication of parameters of the corrosion, said parameters being selected from the group consisting of the extent and the nature of the corrosion, wherein said analysis includes the step of calculating the kurtosis of the noise signals.

2. A method as claimed in claim 1, wherein the electrode means comprises at least two electrodes.

3. A method as claimed in claim 1, wherein the electrode means are exposed to the same corrosion conditions as the metal object.

4. A method as claimed in claim 1, wherein the electrode means comprise at least a portion which is fabricated from the same material as the metal object.

5. A method as claimed in claim 1, wherein the signals analyzed from the electrode means are selected from the group consisting of current noise and voltage noise.

6. A method as claimed in claim 1, wherein the electrode means comprises two electrodes and the signals analyzed comprises the current therebetween.

7. A method as claimed in claim 6, wherein the signals analyzed further include the potential between one of the electrodes and at least one other electrode.

8. A method as claimed in claim 1, wherein the analyzing includes removing a mean value of the electrochemical noise signals followed by normalization of the electrochemical noise signals.

9. A method as claimed in claim 8, wherein the analyzing includes the step of normalizing the electrochemical noise signals to one standard deviation.

10. A method as claimed in claim 1, wherein the analyzing includes the step of calculating the skewness of the noise signals.

11. A method according to claim 10, wherein the skewness of the noise values gives an indication of parameters of corrosion, said parameters being selected from the group consisting of the extent and the nature of the corrosion.

12. A method as claimed in claim 1, wherein the analyzing includes the step of removing the trend of the electrochemical noise signals.

13. A method as claimed in claim 1, wherein the analyzing includes the use of a neural network or expert systems approach.

14. A method according to claim 1, wherein the kurtosis of the noise values gives an indication of parameters of corrosion, said parameters being selected from the group consisting of the extent and the nature of the corrosion.

15. Apparatus for assessing corrosion of a metal object, comprising electrode means capable of generating electrochemical noise signals, and means for calculating the statistical distribution of said noise signals to indicate parameters selected from the group consisting of the extent and the nature of the corrosion, the apparatus including means for calculating the kurtosis of the noise signals.

16. Apparatus as claimed in claim 15, wherein the electrode means comprises at least two electrodes.

17. Apparatus as claimed in claim 15, wherein the electrode means are exposed to the same corrosion conditions as the metal object.

18. Apparatus as claimed in claim 15, wherein the electrode means comprises at least a portion which is fabricated from the same material as the metal object.

19. Apparatus as claimed in claim 15, including a current measuring means electrically connected across the electrode means.

20. Apparatus as claimed in claim 15, wherein the electrode means comprises at least two electrodes, and including a potential measuring means electrically connected between one of the electrodes of the electrode means and at least one other electrode.

21. Apparatus as claimed in claim 15, wherein the means for calculating is a computer.

22. Apparatus as claimed in claim 15, wherein the means for calculating includes a neural network.

23. Apparatus as claimed in claim 15, wherein the means for calculating the kurtosis of the noise signals is a computer.

24. Apparatus as claimed in claim 15, wherein the means for calculating the kurtosis of the noise signals includes a neural network.

25. Apparatus as claimed in claim 15, wherein the apparatus includes means for calculating the skewness of the noise signals.

26. Apparatus as claimed in claim 25, wherein the means for calculating the kurtosis of the noise signals is a computer.

27. Apparatus as claimed in claim 25, wherein the means for calculating the skewness of the noise signals includes a neural network.

* * * * *